（12） United States Patent
Achmüller et al.

(10) Patent No.: US 11,203,620 B2
(45) Date of Patent: Dec. 21, 2021

(54) CONSTITUTIVE YEAST LLP PROMOTOR-BASED EXPRESSION SYSTEMS

(71) Applicant: Sandoz AG, Basel (CH)

(72) Inventors: Clemens Achmüller, Kundl (AT); Ferdinand Zepeck, Kundl (AT); Franz Hartner, Kundl (AT); Thomas Specht, Kundl (AT)

(73) Assignee: Novartis AG, Basel (CH)

( * ) Notice: Subject to any disclaimer, the term of this patent is extended or adjusted under 35 U.S.C. 154(b) by 292 days.

(21) Appl. No.: 15/554,552

(22) PCT Filed: Mar. 2, 2016

(86) PCT No.: PCT/EP2016/054478
§ 371 (c)(1),
(2) Date: Aug. 30, 2017

(87) PCT Pub. No.: WO2016/139279
PCT Pub. Date: Sep. 9, 2016

(65) Prior Publication Data
US 2018/0079788 A1    Mar. 22, 2018

(51) Int. Cl.
*C07K 14/39*  (2006.01)
*C12N 15/81*  (2006.01)
*C07K 14/395* (2006.01)

(52) U.S. Cl.
CPC ............ *C07K 14/39* (2013.01); *C07K 14/395* (2013.01); *C12N 15/81* (2013.01)

(58) Field of Classification Search
CPC ..................................................... C07K 14/39
See application file for complete search history.

(56) References Cited

U.S. PATENT DOCUMENTS

2002/0155513 A1* 10/2002 Hsu .................. C12Q 1/6886
                                                          435/7.23
2014/0302557 A1* 10/2014 Jiang ................... C07K 14/39
                                                           435/69.1

FOREIGN PATENT DOCUMENTS

EP    2184294 A1 *  5/2010   ........... C07K 14/395
EP    2184294 A1    5/2010

OTHER PUBLICATIONS

Schultz et al., Mol. Cell. Biol., 7, 10. 3637-3645 (Year: 1987).*
Tzamarias et al. Distinct TPR motifs of Cyc8 are involved in recruiting the Cyc8-Tup1 corepressor complex to differentially regulated promoters. 1995 Genes & Development 9:821-831 (Year: 1995).*

Genbank Accession FR839628. 2011. Pichia pastoris CBS 7435 chromosome 1, complete replicon sequence (Year: 2011).*
Kebaara et al. Candida albicans Tup1 Is Involved in Farnesol-Mediated Inhibition of Filamentous-Growth Induction. 2008. Eukaryotic Cell, vol. 7, No. 6, p. 980-987 (Year: 2008).*
Shen et al. The mechanism by which overexpression of Gts1p induces flocculation in a FLO8-inactive strain of the yeast *Saccharomyces cerevisiae*. 2006. FEMS Yeast Res 6. 914-923 (Year: 2006).*
Aloys, Teunissen, et al., Transcriptional regulation of flocculation genes in *Saccharomyces cerevisiae*, Yeast, vol. 11, No. 5, pp. 435-446.
Altschul, et al., Nucleic Acids Res. (1997) 25:3389-3402.
Barrales, Ramon R., et al., et al., Indentification of novel activation mechanisms for FL011 regulation in *Saccharomyces cerevisiae*, Genetics, vol. 178, No. 1.
Braus, Gerhard, et al., Amino acid starvation and Gcn4p regulate adhesive growth and FL011 gene expression in *Saccharomyces cerevisiae*, Molecular Biology of the Cell, vol. 14, No. 10.
Database Geneseq NCBI, Pichia pastoris GS115 chromosome 1, Database accession No. FN392319.
Fleming, Alastair B., et al., The yeast Cyc8-Tup1 complex cooperates with Hdalp and Rpd3p histone deacetylases to robustly repress transcription of the subtelomeric FI01 gene, BBA—Gene Regulatory Mechanisms, vol. 1839, No. 11.
Fleming, Alastair, B., et al., Antagonistic remodeling by Swi-Snf and Tup1-Ssn6 of an extensive chromatin region forms the background for FL01 gene regulation, EMBO Journal, vol. 20, No. 18.
Hua, Shen, et al., The mechanism by which overexpression of Gtslp induces flocculation in a FL08-inactive strain of the yeast *Saccharomyces cerevisiae*, Fems Yeast Research, vol. 6, No. 6.
Kuberl, A., et al., High-quality genome sequence of Pichia pastoris CBS7435, J Biotechnol, vol. 154, issue 4, pp. 312-320 year 2011.
Lo, W-S, et al., FL011, A yeast gene related to the STA genes, encodes a novel cell surface flocculin, Journal of Bacteriology, vol. 178, No. 24.

(Continued)

*Primary Examiner* — Neil P Hammell
*Assistant Examiner* — Tiffany Nicole Grooms
(74) *Attorney, Agent, or Firm* — Luedeka Neely Group, P.C.

(57) ABSTRACT

The present invention provides a modified eukaryotic cell wherein the modified eukaryotic cell is not able to provide an SSN6-like protein that exerts its wildtype function and/or wildtype activity, the amount of SSN6-like protein being present in the modified eukaryotic cell differs from the amount of SSN6-like protein being present in its wildtype form, and/or essentially no SSN6-like protein is present in the modified cell. Additionally, the present invention provides a polynucleotide sequence comprising a modified ssn6-like gene, and a vector comprising said polynucleoptide. Additionally provided is an expression vector comprising a promoter that is repressed in the presence of SSN6-like protein, and a host cell comprising said vectors. The present invention further refers to a method for determining the purity of a composition by using the modified eukaryotic cell, to a method of expressing gene(s) of interest, and eukaryotic cells comprising modified ssn6-like gene.

16 Claims, 28 Drawing Sheets
Specification includes a Sequence Listing.

(56) References Cited

OTHER PUBLICATIONS

Rubintz, Jeffrey, et al., The Minimum Amount of Homology Required for Homologous Recombination in Mammalian Cells, 1984, Mol Cell Biol. 4: 2253-2258.

Search Report and Written Opinion for Singapore App. No. 11201707056U, dated Jul. 2, 2018, 12 pages.

Trumbly, et al., Cloning and characterization of the CYC8 gene mediating glucoserepression in yeast, Gene, vol. 73, No. 1.

Tzamarias, D. et al., Distinct TPR Motifs of CYC8 involved in recruiting the cyc8-tup1 corepressor complex to differentially regulated promoters, Genes and Development, vol. 9, No. 7.

Wasserman, Wyeth, et al., al., Applied bioinformatics for the identification of regulatory elements, Nature Reviews Genetics, vol. 5, No. 4.

Williams, Frederick E., et al., Characterization of TUP1, a mediator of glucose repression in *Saccharomyces cerevisiae*, Mol. Cel. Biol. 10(12), 1990, pp. 6500-6511.

Search Report and Written Opinion for PCT/EP2016/054478, dated Sep. 9, 2016, 24 pages.

\* cited by examiner

Fig. 1: Polynucleotide sequences

Fig. 1 A shows the nucleotide sequence of the coding region of the ssn6-like gene of P. Pastoris (SEQ ID. NO: 1).

```
ATGAACGAACCTTCACAGCCTCCGCCAGTGACACTGGAAGTGAGGCATGATCCCGTACCAACGTCTCAAGCTGACTCCCAGCAACGGAAAG
TGGTATATGATAAACAACTCGAGTTTCGCAAGATAGCTGTCTCCACTTGGCTAGCGCTCGGATCCATGGCTCACGAAGTCCACTTGTACCA
GCTGGCAATTGATTCGTTCGATTTTGCCCTCCAAAATGATCCATTCAACGAGAAGGCTCTTTGTGGACTCGCAGCTGCATTGAGGGCTATG
GATCTGGTCAAGGACCAAACAGACGGTACCGCAGCGGCCCTGGATGTTATCAACGACCTTTTATCACGCTCATCAGAGCTTTACAAAGATC
CATCTATCTGGAGAGAAGCTGCCGAATGCTATCTACTCTTAAACAACACAACGAATGCCATGGAGGCCCTACAAAGATGTATTCAATTAAC
TCCCAACAACTCTGCATTATGGTTACTTAAAGGACAAACATTGATGGCCGCAGGTTCCAAACATGAGGCCGTCGATGCACTGAACACAGCC
TTGGTGAAACTCCCCAATGACGTTGCAGACTATACAAAAGAAGAGATTGACGTGGCCCGTTCCACCCACTCAGAATTTGCCTCCGTTCTTG
CTGCGGAGGGCAACATCGAAGCTGCCAGGGATGAGTTGGAGGCCACTTTGGCTCTTCCGCCTCCCTCTTCTTCCCGCTTCACAGAGTATTC
CTCTCTTTGGTGCGCCCTCATTAGTGCTAATGAGCGCCTTGGAGATATGGCCAAGGCAGTGCGCGTCTGTGAGGAGGCATCTGGACTGTTA
GGATTCGAGCCATGCATATATATATGCCACGCATACTTGTTGCTACTACCGAACAGTCACGTATTTAACCCACAGTCTGCTTGTGTCCTGC
TTCGGCAAGTTGTTAATTCGGAAAGCAACGACTTTCTACCATGGTTTTTACTTGGTGAGGCTTATCAAATGCTGCGCCAACCAAGCGAGGC
CTACGAAGCATTCCAGTTGGCCTTGAAAAGGGCTCCAAACCACACAATTGTATGGCTTGCAGTGGGAAACCTTTATGCCGAACTGGGCCAG
CTGGCTGATGCCCTTAGCGCGTATATGTTTGTCATCAAACGTGAAACAGAACAAGAACAAGAGAGCAAGATTTTGCTCTCATTTGCTTGGG
AGGGTCTTTCATCGGTGTACGAAAAGTGTCATGGTCAGTTGGCTGACTCTATAGAGGCCTGTATGAAGTCAAGCAGCTATGCAAGCCAAGC
GGGTGATAGCTCTCGGGCAAATTTCTTGAACTCGCGATTGGAAACTTTACGAAGAGTGGTATCTGGAGAGATTCCGCTTTCTGATTACAGA
CCAAGCACATGTTGTCAATCTCCGTTATATTTACTGCGAGATCTTACTTCACTGAGTATATCTGAAAGAGAAAATTTGGCCAATGCTTCGT
TAGATGACATCGCATCCGCTCCAGAAATCAAGAGTAGCAGCAAGAAGCGAACTGACACTTCGAGACCAATGCCTCCCTACCCGTCTCACTC
CGCAAATAACTATAACCTACCATCCGAAGATTCACAGCCACAGCGACAGAACTTACCAGTTCACTCACTCCCTAACGTTCCATTAGCACAG
CAACAGCGTGTGCATGCTCCGGCAAACAAGAACTTGTCCCCAAGCGCCGATCAGAGATTCTCAATTGCAACCCATCCTCCTGTTGCCCCCC
CCACAAATTTCCCCTCGTCCTGCTTCACCACAGTTACAACAACAACAGCAACAACAGCAGCAACAGTTTCAACCACAAAACTATCAGCACT
ATGCGCCTTCACCAATGTACCCACCTTCCCAACAATCCCCATTCCCTGA
```

Fig. 1 B shows the nucleotide sequence of the LLP promoter of P. Pastoris, 605 bp 3' from the ATG start codon of LLP (SEQ ID NO: 2)

```
ACAAAATGGCCAAGCTGGGAAACGGGATTTGGTGGAACTTTATTATTCTTTCTACGATCCAAGCATTATGTTGTGGAACAAAGCGAATACT
CTTATTAGCTGGTAATTGAGCGAGTTGAAAAAATCAAGTCTATTGGAGGGTATGGTCAGAGTACTGATAGAGATCCCTGTTAAGATAATCG
ATCTTTTTCAAATATCCAATTTCATTCCATCTTGCCATCGGGTCTTGGCTTCTTACATCAATAATTAAAACTACTTACTCTATTAGTGCCA
AAAATGGTAAACCGTATTCAAATTGCTGCAAGCATATGCTTAAAAGGATCGCGTTGCGAGCTTCTTTTGAGATTCGCAAGCTTGATTTTAT
GCTCTTGTGGGAAGAAAAGCAACCCACTGAATTCCAGATTTGTTGTGTTTTCATGCATGGACGACATACTTTGAGTAATACCGTTACTGAG
ATTTTACCGAATTCGCATTGCGTTGAGGCGTGAAGTTTCTTAATGCTGTGCCATATGGTTAAGTTGCGTTTCAAGATGGTCCACAAGTATT
TTTGTATTTAAGCAGTGTCAATTCAAGCCTAACTGCTCATAAAAACTACACGGTTTGCT
```

Fig. 1 C shows the nucleotide sequence of the signal sequence of the LLP protein of P. Pastoris (SEQ ID NO: 3). Nucleotide at position 45, is underlined.

```
ATGTTTGAGAAGAGTAAATTTGTGGTTTCGTTTCTGCTTTTACTGCAGCTATTTTGTGTCCTTGGTGTACATGGA
```

Fig. 1 D shows the nucleotide sequence of the terminator sequence of llp gene of P. Pastoris (SEQ ID NO: 4).

```
ACGGTCTTGGAGTCATCAGGCTCTGACTGGGCAGCTGCTGCAACTGGAACTTCCCAAGCCTCCCACCAAACAGCAGGTGTAGCCGAAAGTA
TTCACGTGTCCCAGAATGAGGCCCACAGTACATCTGTCACCGTTTCTCAACCCCCTTCAACGGTTTCTTTGCAAATTGGAGAAGCAAATAC
CCTGAAATGGTCAGCTTTCTTTGGAGTAGTAGTTCCGCTGCTCAACGTACTCTTCGTTTAAAAGCCCT
```

Fig. 1 E shows the nucleotide sequence of the SSN6-like promoter of P. Pastoris, 1000 bp 3' from the ATG start codon of SSN6-like (SEQ ID NO: 5).

```
GGAATGGAAGGGTGCAGCCTCTCATTTCTGTTGTGCCCTTTCAAGGCGTGTTTACCATTTTCGGCTGATGGGAGTGGACTAAAAGGAAATT
ACCCTATTGACACAATCCGACTTTCGTGGATCTTGTTTTAGTAAACCCATTTTTGGGTTGCTTTTGAACAAAAAAAAAGCACAAGTCTGCA
TATTACTAAGAATTACCATGGTAACATATTGCACTTGCATGCGCAGAATGCATTAACAACAAGCAGCTCAGAAAGGCTGAAATTGAGGATA
CGCGCTTCATTAAAAAATGCTGCGTTTGAAAATGTGTGCAACAACTTTGCATCAGCACAGAAAACACGACGCAGTAGTCCTAGTAGGGTGA
TATTTGGCCGCCATCTTGCTCTGGAGTGTCGAGTTAATTATTTTGCCCCTTGATTTCAAAACGTTACTTTGTTTCCTTTTTTTCTAGTTCA
CCTTTTGTACGGGTTAGTAACTTTGCATATCTGATTGTTACAAAAGTGGATGGCAATGCAAGCTGGATGCGCATGAACAGTGTTCCAGGCA
CTAATTTTAACGTGATGTGTCTCTTCTCGAAGATGCATTATTTTATACACAGCATCTTGGTTGCATTACATTATGTATGCACCTATCATGT
ATATATGTACGCCCGTAAGTAATCGTAGGTCTAATAAGCAAACGTATGCAGAGGTTGTAAATTTTTGAAACGCTCAGTCGGAGCATCATTT
CCAAGGCTAAGTTGTGTTCTTCTTCTTCTTTCCTCCCTACACTCCCAAAAATTCCTTGCCACTTCAGATTTCTTTTGTGAAAACTTTCAAT
ACTCAGAACACTCCCCTCCAGACTATAGAGTTCCACTCTCCCCCTCCTCTATTCAATTTCAACTCTCTTGTTGTCAAGAGATCCAGTGTTA
GATTGTTGCCACAAGGAAAGAGAAACAAGGAAACATTCCATTTCATCCATTCTCGTATCAACTGGCACCCCACGATATTTACCACTACTT
```

Fig. 1 F shows the nucleotide sequence of the terminator sequence of ssn6-like gene of P. Pastoris (SEQ ID NO: 6).

```
ACACCAGAAAAGTTTGACTTCTTTCAATCAAATGCCGCCTATTCCTCCACCACCTCCTCCTCCTCAACATCAGCAACACCCTCAGCAGATG
CACATTGTACAGCAACAACATGAACAGCAGCATCATCAGCAGCAGCATCTGCACCCGCAACATTTGATGCCTCTCCCTCCGTTACATCAAG
GCCCACCTATTCCTAAGATAGAGTCTCCTTCATATCGGAATCAACAGTCATTCATGGTTGGGGTGCCCTATTCGGGGGTCGGTCCTGATGG
AAGACCAATATACGAACCGTCTCAATTCTATGGGTCACATCCTCCGGCACGCTTTGTGGTTAACGAATAGATATTATAATATGCTTATTTA
GTGATCATAGCAACGAATATATAATCATAACAGCCCAACTAAACGTTCAACGAGCGTTTCCACATCCTGTGCAGCCTCTTGGGCGTGCAAC
AGCACTTCTTCATGGCTGGCATGGCCTTTGCTGTCAGGTGTTTGA
```

Fig. 1 G shows the nucleotide sequence of the ssn6-like modified DNA of P. Pastoris (SEQ ID NO: 7).

```
ATGAACGAACCTTCACAGCCTCCGCCAGTGACACTGGAAGTGAGGCATGATCCCGTACCAACGTCTCAAGCTGACTCCCAGCAACGGAAAG
TGGTATATGATAAACAACTCGAGTTTCGCAAGATAGCTGTCTCCACTTGGCTAGCGCTCGGATCCATGGCTCACGAAGTCCACTTGTACCA
GCTGGCAATTGATTCGTTCGATTTTGCCCTCCAAAATGATCCATTCAACGAGAAGGCTCTTTGTGGACTCGCAGCTGCATTGAGGGCTATG
GATCTGGTCAAGGACCAAACAGACGGTACCGCAGCGGCCCTGGATGTTATCAACGACCTTTTATCACGCTCATCAGAGCTTTACAAAGATC
CATCTATCTGGAGAGAAGCTGCCGAATGCTATCTACTCTTAAACAACACAACGAATGCCATGGAGGCCCTACAAAGATGTATTCAATTAAC
TCCCAACAACTCTGCATTATGGTTACTTAAAGGACAAACATTGATGGCCGCAGGTTCCAAACATGAGGCCGTCGATGCACTGAACACAGCC
TTGGTGAAACTCCCCAATGACGTTGCAGACTATACAAAAGAAGAGATTGACGTGGCCCGTTCCACCCACTCAGAATTTGCCTCCGTTCTTG
CTGCGGAGGGCAACATCGAAGCTGCCAGGGATGAGTTGGAGGCCACTTTGGCTCTTCCGCCTCCCTCTTCTTCCCGCTTCACAGAGTATTC
CTCTCTTTGGTGCGCCCTCATTAGTGCTAATGAGCGCCTTGGAGATATGGCCAAGGCAGTGCGCGTCTGTGAGGAGGCATCTGGACTGTTA
GGATTCGAGCCATGCATATATATGCCACGCATACTTGTTGCTACTACCGAACAGTCACGTATTTAACCCACAGTCTGCTTGTGTCCTGC
TTCGGCAAGTTGTTAATTCGGAAAGCAACGACTTTCTACCATGGTTTTTACTTGGTGAGGCTTATCAAATGCTGCGCCAACCAAGCGAGGC
CTACGAAGCATTCCAGTTGGCCTTGAAAAGGGCTCCAAACCACACAATTGTATGGCTTGCAGTGGGAAACCTTTATGCCGAACTGGGCCAG
CTGGCTGATGAGTGGTACCTGCAGCTAAGGTAA
```

Fig. 1 H shows the nucleotide sequence of the Kozak start sequence (SEQ ID NO: 11).

```
GATATCAAAACGATG
```

Fig. 1 I shows the nucleotide sequence of the LLP promoter of P. Pastoris, 1000 bp 3' from the ATG start codon of LLP (SEQ ID NO: 12). The underlined sequence part is identical to SEQ ID NO: 2, Fig. 1 B.

```
AGATAGATAACTACAATTTATGAGGCCCTATCGTGAAATAGCAACGTAGAATAATTTCCTGGCAGAGTAGGGTGTGGGGTCAGTAGAAGTA
ATATCCAGAAGCTGATGCAGGTTATTGATATTACCACAAGATTCTAGCTTCAAATGCACAGTTCGGATTGGTGATCCGAAGATGCTAAAAA
AAAGACATCAAACTCCAAACCGTATCGCTTTTTACGGCGTATATTGTTGCACGAAAGCGAACTATAATCATGCAGAAAACATGCGGACATG
ACGTAATGTATGCGTTTAGGGAAAGGTACTGCGTATTTCAAACGCATACTTAGATCGTGCCCAGCAACCCACATAATTTTTTCTTCAAGGT
CTGGACATACTGGTTGTGTCAAAATAGGGCAACAAAATGGCCAAGCTGGGAAACGGGATTTGGTGGAACTTTATTATTCTTTCTACGATCC
AAGCATTATGTTGTGGAACAAAGCGAATACTCTTATTAGCTGGTAATTGAGCGAGTTGAAAAAATCAAGTCTATTGGAGGGTATGGTCAGA
GTACTGATAGAGATCCCTGTTAAGATAATCGATCTTTTTCAAATATCCAATTTCATTCCATCTTGCCATCGGGTCTTGGCTTCTTACATCA
ATAATTAAAACTACTTACTCTATTAGTGCCAAAAATGGTAAACCGTATTCAAATTGCTGCAAGCATATGCTTAAAAGGATCGCGTTGCGAG
CTTCTTTTGAGATTCGCAAGCTTGATTTTATGCTCTTGTGGGAAGAAAAGCAACCCACTGAATTCCAGATTTGTTGTGTTTTCATGCATGG
ACGACATACTTTGAGTAATACCGTTACTGAGATTTTACCGAATTCGCATTGCGTTGAGGCGTGAAGTTTCTTAATGCTGTGCCATATGGTT
AAGTTGCGTTTCAAGATGGTCCACAAGTATTTTTGTATTTAAGCAGTGTCAATTCAAGCCTAACTGCTCATAAAAACTACACGGTTTGCT
```

Fig. 1 J shows the amino acid sequence of the SSN6-like protein of P. Pastoris (SEQ ID NO: 13).

```
MNEPSQPPPVTLEVRHDPVPTSQADSQQRKVVYDKQLEFRKIAVSTWLALGSMAHEVHLYQLAIDSFDFALQNDPFNEKALCGLAAALRAM
DLVKDQTDGTAAALDVINDLLSRSSELYKDPSIWREAAECYLLLNNTTNAMEALQRCIQLTPNNSALWLLKGQTLMAAGSKHEAVDALNTA
LVKLPNDVADYTKEEIDVARSTHSEFASVLAAEGNIEAARDELEATLALPPPSSSRFTEYSSLWCALISANERLGDMAKAVRVCEEASGLL
GFEPCIYICHAYLLLLPNSHVFNPQSACVLLRQVVNSESNDFLPWFLLGEAYQMLRQPSEAYEAFQLALKRAPNHTIVWLAVGNLYAELGQ
LADALSAYMFVIKRETEQEQESKILLSFAWEGLSSVYEKCHGQLADSIEACMKSSSYASQAGDSSRANFLNSRLETLRRVVSGEIPLSDYR
PSTCCQSPLYLLRDLTSLSISERENLANASLDDIASAPEIKSSSKKRTDTSRPMPPYPSHSANNYNLPSEDSQPQRQNLPVHSLPNVPLAQ
QQRVHAPANKNLSPSADQRFSIATHPPVAPPTNFPSSCFTTVTTTTATTAATVSTTKLSALCAFTNVPTFPTIPIP
```

Fig. 1 K shows the nucleotide sequence of the MFalpha pre-pro signal sequence without (A) and with the EAEA repeat (B) as used in the examples of this application.

(A): SEQ ID NO: 14

```
ATGCGTTTCCCATCGATTTTCACAGCTGTTCTGTTTGCAGCTTCATCTGCTTTAGCTGCACCTGTTAACACAACTACAGAGGACGAAACGG
CCCAGATCCCAGCTGAGGCAGTCATTGGTTATTCCGATTTGGAAGGTGATTTCGATGTCGCTGTGTTACCATTCAGTAATTCCACAAATAA
CGGTTTGCTGTTCATTAACACCACTATAGCAAGCATCGCTGCAAAAGAGGAAGGTGTTTCCCTAGAAAAGAGG
```

(B): SEQ ID NO: 21

```
ATGAGATTCCCATCTATTTTCACCGCTGTCTTGTTCGCTGCCTCCTCTGCATTGGCTGCCCCTGTTAACACTACCACTGAAGACGAGACTG
CTCAAATTCCAGCTGAAGCAGTTATCGGTTACTCTGACCTTGAGGGTGATTCGACGTCGCTGTTTTGCCTTTCTCTAACTCCACTAACAA
CGGTTTGTTGTTCATTAACACCACTATCGCTTCCATTGCTGCTAAGGAAGAGGGTGTCTCTCTCGAGAAGAGAGAGGCCGAAGCT
```

Fig. 1 L shows the codon optimized DNA sequence of encoding a single chain antibody fragment DLX521 (SEQ ID NO: 15).

```
GCCCAGTCCGTTTTGACTCAACCCCCTTCCGTATCCGCAGCTCCAGGCCAAAAAGTAACGATCTCTTGTTCAGGTTCCACTAGTAACATAG
GTGACAATTATGTGTCATGGTACCAACAGTTGCCCGGAACTGCCCCTCAACTGCTGATCTACGACAATACCAAGAGGCCGTCAGGTATCCC
AGACAGATTTTCCGGTTCTAAGAGCGGCACATCGGCTACACTAGGTATCACGGGACTTCAAACCGGCGACGAGGCAGATTACTACTGCGCA
ACTTGGGATAATGATAAGTGGGGAGTTGTTTTTGGAGGTGGTACTAAACTCGAAGTCTTGGGTGGTGGAGGAGGATCAGGAGGAGGAGGTT
CTGGAGGAGGTGGTTCATCTGGCGGTGGATCTGAAGTGCAGCTTGTGGAGAGTGGTGGTGGTTTGGTTCAACCAGGAGGTAGCTTGAGACT
GTCATGTGCCGCCAGCGGTTTTACTTTCTCCTCCTATGCAATGTCTTGGGTCAGACAAGCACCTGGTAAGGGTTTGGAATGGGTATCAGCT
ATTTCGGGTAGTGGTGGTTCGACATATTATGCTGACTCCGTTAAAGGTCGTTTTACTATTTCTAGAGACAATTCCAAAAATACCTTATATC
TTCAAATGAACTCCCTTAGAGCTGAGGATACTGCTGTTTACTACTGTGCTCGTGATGCTTGGTTGGATGTGTTGTCTGACGGCTTTGACTA
CTGGGGACAAGGTACTTTGGTCACAGTGAGCAGCTGA
```

Fig. 1 M shows the coding region of the Ilp-gene including the signal sequence of P. Pastoris (SEQ ID NO: 16)

```
ATGTTTGAGAAGAGTAAATTTGTGGTTTCGTTTCTGCTTTTACTGCAGCTATTTTGTGTCCTTGGTGTACATGGACAAGAAAGTGGTAACG
GTACCACTAGTGACACTGCCTACGCATGCGACATCGGTGCAACACCTTTTGACGGATTCAATGCTACTATTTATCAGTACCAGGCAAGTGA
TGACAATTCAATACAGGACCCGGTTTTTATGAGCACTGGGTACTTGCAACGTAACCAGTTGCATAGTACAACTGGAGTGACTAATCCGGGG
TTCAACATCTTCACTGCAGGCGTTGCCACCACAACACTTTATGGGATACCAAACGTCAACTACCAAAATATGCTTTTAGAATTGAAAGGCT
ATTTCAGAGCTGACGCCTCTGGAAATTATGGACTATCACTAAGGAACATCGATGATAGTGCGATTCTTTTCTTTGGGAGGGAGACTGCGTT
TGAATGTTGCAATGAAAATTTGATTCCCTTGGACGAAGCCCCAACTGATTACTCACTTTTTACCATTAAAGAAGGGGAAGCTTCAACAAAC
CCCGACTCTTATACGTACACTCAATACTTGGAGGCTGGGAGATACTATCCCGTAAGAACTTTCTTTGCCAACATAAGAACGCGTGCCGTGT
TCAACTTTACGATGACACTGCCAGACGGGAGTGAACTAACAGATTTTCAAAACTACATTTTTCAATTTGGAGCTCTTAACCAACAACAATG
CCAAGCAGAAATAGTTACCAGGGAAAATTACACAACCACCACCGAACCATGGACTGGTACCTTTGAAGCCACGACCACGGTGATTCCAAGT
GGCACTGAGCCAGGTACCGTGATTGTCCAGACTCCTTATTCTACTATCGACTCCACATCTACTTGGACCGGTACTTTCACCACTTTCACCA
CCGATGCTGATGGAAGCACCATCGCCGTTGTGCCATCGTCGACTATTGATGATCACTTTGCGTCGACTGAAACTGTTTTGACAGACACTGC
TATTTCAACTACTGTTATTACCGTGACCAGTTGTGGTACCAGTAAGTGTACCAAGACTACAGCACTAACAGGGGTGACTCAGCGAACTCTC
ACAATCGATGATAGAACTACTGTCGTGACGACTTACTGTCCTTTGCCAACTGACGTTGCCACTATAAAAACAGCAAGTGTTAGCGGAAGTG
AGGTTGTGCAAACAATCTACACTGCGAAACACAGCCAGGCCGTTTCTTATGTTCATCCATCAACTGTTACAATCACAAGAGAGGTATGTGA
TGCCCAAACTTGCACGCAGGCTACTATTGTGACTGGAGAAATTCTGCAAACTACTGTTGTGGACTCTGGTTCTACAACTGTTGTTCCAAAG
TATGTTCCGGTGGAGACGCATGAACCAACATTTGAATTGAGTACTCTTTAA
```

Fig. 1 N shows the codon-optimized nucleotide sequence of the human Growth Hormone (hGH) as used in the examples of this application (SEQ ID NO: 17).

```
TTTCCAACCATCCCGCTGTCCAGATTGTTTGACAATGCCATGTTGAGAGCCCATCGTTTGCATCAGCTCGCATTTGATACGTACCAGGAAT
TTGAGGAGGCTTACATTCCAAAAGAGCAAAAGTATAGCTTTCTACAGAATCCTCAGACTTCGCTGTGTTTCTCTGAATCTATCCCTACACC
CAGTAATAGAGAAGAGACTCAACAAAAGTCTAACTTGGAATTGTTGAGAATATCACTGCTGTTGATTCAATCTTGGCTTGAACCTGTGCAA
TTCTTGAGATCTGTCTTTGCTAATTCACTTGTGTATGGAGCTTCCGACTCAAATGTATACGACCTCTTAAAAGACCTTGAAGAGGGCATCC
AAACTTTGATGGGACGACTTGAAGATGGATCCCCCAGGACCGGTCAAATCTTCAAGCAAACTTACAGCAAGTTCGACACAAACTCCCACAA
TGATGATGCCTTATTGAAAAACTACGGATTGCTATATTGTTTTCGTAAAGATATGGACAAAGTAGAGACTTTTCTGAGAATTGTTCAATGT
AGAAGTGTTGAGGGTTCATGCGGTTTCTAA
```

Fig. 1 O shows the codon optimized nucleotide sequence of the human serum albumin (HSA) incl. the HSA signal sequence as used in the examples of this application (SEQ ID NO: 18).

```
ATGAAATGGGTGACTTTTATCTCCCTACTGTTCCTTTTCTCCTCCGCATACTCAAGAGGTGTTTTTAGAAGAGATGCCCATAAGAGTGAGG
TTGCACACAGATTTAAGGATTTGGGAGAAGAGAATTTCAAGGCTCTGGTGTTGATAGCTTTCGCTCAATACTTACAACAGTGTCCATTTGA
AGATCATGTCAAATTGGTCAATGAAGTAACGGAGTTCGCTAAAACATGCGTCGCTGACGAATCAGCTGAAAATTGTGATAAGTCGTTACAT
ACCTTGTTCGGTGACAAATTGTGCACGGTTGCAACATTGCGAGAAACATATGGCGAAATGGCAGATTGTTGCGCTAAGCAAGAGCCTGAAA
GGAACGAGTGTTTCTTACAGCATAAGGATGATAATCCAAACCTACCTAGATTGGTCAGACCAGAAGTTGACGTTATGTGTACCGCTTTTCA
CGATAACGAAGAGACATTCTTGAAAAAGTACCTGTACGAAATCGCAAGACGTCATCCATACTTCTATGCCCCAGAGCTGTTGTTTTTCGCA
```

Fig. 1 O (continued)

```
AAAAGATATAAGGCCGCATTTACTGAATGCTGTCAAGCTGCTGATAAGGCTGCTTGCCTTCTCCCTAAACTGGATGAGTTGCGTGATGAAG
GAAAAGCAAGTTCGGCCAAGCAAAGACTGAAGTGTGCTAGCTTACAAAAGTTTGGTGAACGTGCGTTCAAGGCTTGGGCTGTGGCAAGATT
ATCTCAAAGATTTCCTAAGGCAGAATTCGCCGAAGTGTCGAAACTTGTAACCGACCTTACTAAAGTGCACACCGAGTGCTGTCATGGAGAT
CTACTCGAATGCGCAGACGACAGAGCTGACCTGGCTAAGTACATTTGTGAGAACCAAGATAGCATTTCTTCCAAATTGAAGGAATGTTGTG
AAAAACCCTTGCTTGAGAAATCTCACTGTATCGCTGAAGTTGAAAATGACGAGATGCCCGCCGACCTTCCAAGTTTAGCAGCTGACTTTGT
TGAATCTAAAGACGTGTGTAAAAACTATGCAGAGGCTAAGGACGTCTTTTTGGGTATGTTTCTGTACGAGTATGCTCGTAGACATCCAGAT
TACTCCGTTGTTCTGCTGTTGAGGCTTGCCAAGACTTACGAGACAACTTTGGAGAAATGTTGTGCCGCAGCAGACCCTCACGAGTGTTATG
CAAAAGTGTTTGATGAATTCAAGCCATTGGTTGAGGAACCACAGAATCTGATTAAACAAAACTGTGAATTGTTTGAACAACTAGGTGAGTA
TAAGTTCCAGAACGCTCTGCTGGTTCGTTATACTAAAAAGGTTCCTCAGGTTTCAACTCCTACATTGGTAGAGGTCAGCAGAAATTTGGGA
AAGGTTGGTTCAAAATGTTGTAAACATCCCGAGGCTAAAAGGATGCCGTGTGCTGAGGATTACTTGTCTGTCGTATTGAATCAGTTATGTG
TGTTACACGAAAAGACACCAGTCTCTGATCGTGTGACGAAATGCTGCACAGAGTCACTCGTTAATCGTAGACCTTGTTTCTCCGCTTTGGA
GGTGGACGAGACTTACGTACCTAAAGAGTTCAATGCTGAAACTTTTACTTTTCACGCTGACATTTGTACTCTTTCCGAAAAAGAGAGGCAA
ATCAAAAAGCAAACTGCTTTGGTTGAATTAGTTAAGCATAAGCCAAAAGCTACTAAGGAGCAACTTAAAGCAGTAATGGACGATTTCGCTG
CATTCGTTGAAAAGTGCTGTAAAGCCGACGATAAAGAGACATGTTTTGCAGAGGAAGGTAAAAAGTTGGTCGCTGCCTCCCAGGCCGCACT
AGGTTTGTAA
```

Fig. 1 P shows the codon-optimized nucleotide sequence of the penicillin V amidase (PVA) as used in the examples of this application (SEQ ID NO: 19).

```
GCTAGAACTACCGAGCCAATCATTGACTTAGGATACGCTAGATACAGAGGTTCAATCAACGACACTACCTCTGTCACTTCATACCTGGGTA
TCAGATTTGCTGAACCTCCAGTTGAGGACTTGAGATGGAGAGCCCCACAACCTGCTAAGAGACTTCCTGGTGTTCAAAACGCCACTATTGT
TCCTCCATTGTGTCCACAAGGTTTCATCAACATCTTGATTCCAGGAGGTATTCCACCTCCAGACTTGACCAACGTTTCTGAAGACTGCTTG
TTCTTGTCCGTTTTTGCACCTAGAAAGTTGCCACCTAAGCGTAAGGAATTGCCAGTGATTGTTTGGATTCATGGTGGAGGATACATCGTCT
CCTCTGCAGCTACTTTCGACGGAACTAACTTGGTTAGAGAGTCTAACGACTCTGTCATTGTGGTGACTATCCAGTACAGACTGGGAATTTT
CGGATTCATGGCTGGTAAGAAGTTGAAGGATAACGGAGACTTGAATGCTGGATTGCTTGACCAAGAGTTGGCTTTGAAGTGGGTTCAACAG
CACATTAACAAGTTCGGTGGTGACCCTAAGCAAGTGACCATTTGGGGTCAATCAGCTGGAGGTGGTTCTGTGTTGCAACAGGTCATTGCTC
ACAACGGACAAACTAACCCACCATTGTTCAGAGCTGCTATGTCTTCCTCTACCTACCTTCCTTCTCAACACCATTTCGACGATCCTGTTCC
AGAAGGTATCTACTCTACCGTTGTCTCAACTGCTGGTTGTGCTGATGCTACTGATCCTCTTACTTGCTTGAGAGCTTCTAACACCTCCATC
TTACAAGCTGCTAACGACAAGGCATGTAGATCCGCATTCTACGGTACTTCCGTTGTTGTTCCTGTTGTTGATGGTGAGTTCATCACCCAAA
GACCATCTGAAGCTCTTAGACAAAGACGTGTCAACGGTAACGCTTTGTTGGCTATCTCTAATACCAACGAAGGTGACATCTTCGTTGACCA
ATCTAAGGCTGACACTGTTACTGCTGCTCAGTTCGTTAGAGACTTGTACCCTAGATTGAACGGTGCTCAAGTTGCTGAGGTTGTTCGTCTG
TACTCTGGTTTAGGTGCTCCAATCCAACAGGCTGACTCTATCATGGGAGATACTCTGTTCCAATGTCCAACCATTTGGTTCTCTCAAGCCT
TCAGACAATCTTTCAAGGGTGAATACGCTGTTCTTCCTGCATTCCACGGTTCTGACATTTCCCAGTACTTCCCATCTTTTGCTCCTAGATT
CTTCGACGATCCTGCTTTCACTTCCTCTTTCACTCAGTCCTTCTTGGACTTCGCTTTGTCTCGTAACTCTGATCCTAACGCAAAGTTTGAC
GACGGTAACTTGACTCCTAGATGGAACAGATACACCTCTTGCTCAAAGTTCGAGATGGTGTTCAACCGTACTGATGGTGAAGAGTTGGACA
TTAGACCAGCTTCTACTGGTGCTGGTTTGTTGGAGAGATGTGCATTCTGGGAATCTGTCTCCGAATTGACTGCTCAATAA
```

Fig. 1 Q shows the nucleotide sequence (SEQ ID NO: 20) of the vector pGAPk used for generating the SSS1 yeast cell line (plasmid without a GOI and with a Geneticin resistance marker). The hybridization site of the primer oligo2398 is labeled in grey and underlined, and of oligo2395 is labeled in grey and double-underlined (reverse-complement sequence)

```
AGATCCAATTCCCGCTTTGACTGCCTGAAATCTCCATCGCCTACAATGATGACATTTGGATTTGGTTGACTCATGTTGGTATTGTGAAATA
GACGCAGATCGGGAACACTGAAAAATACACAGTTATTATTCAGATCTTTTTTGTAGAAATGTCTTGGTGTCCTCGTCCAATCAGGTAGCCA
TCTCTGAAATATCTGGCTCCGTTGCAACTCCGAACGACCTGCTGGCAACGTAAAATTCTCCGGGGTAAAACTTAAATGTGGAGTAATGAA
CCAGAAACGTCTCTTCCCTTCTCTCTCCTTCCACCGCCCGTTACCGTCCCTAGGAAATTTTACTCTGCTGGAGAGCTTCTTCTACGGCCCC
CTTGCAGCAATGCTCTTCCCAGCATTACGTTGCGGGTAAAACGGAGGTCGTGTACCCGACCTAGCAGCCCAGGGATGGAAAAGTCCCGGCC
GTCGCTGGCAATAATAGCGGGCGGACGCATGTCATGAGATTATTGGAAACCACCAGAATCGAATATAAAAGGCGAACACCTTTCCCAATTT
TGGTTTCTCCTGACCCAAAGACTTTAAATTTAATTTATTTGTCCCTATTTCAATCAATTGAACAACTATCAAAACACAGAATTCACTAGTG
GCGCGCCGCGGCCGCTCAAGAGGATGTCAGAATGCCATTTGCCTGAGAGATGCAGGCTTCATTTTTGATACTTTTTATTTGTAACCTATA
TAGTATAGGATTTTTTTTGTCATTTTGTTTCTTCTCGTACGAGCTTGCTCCTGATCAGCCTATCTCGCAGCAGATGAATATCTTGTGGTAG
GGGTTTGGGAAAATCATTCGAGTTTGATGTTTTTCTTGGTATTTCCCACTCCTCTTCAGAGTACAGAAGATTAAGTGAGACCTTCGTTTGT
GCGGATCCTTCAGTAATGTCTTGTTTCTTTTGTTGCAGTGGTGAGCCATTTTGACTTCGTGAAAGTTTCTTTAGAATAGTTGTTTCCAGAG
GCCAAACATTCCACCCGTAGTAAAGTGCAAGCGTAGGAAGACCAAGACTGGCATAAATCAGGTATAAGTGTCGAGCACTGGCAGGTGATCT
TCTGAAAGTTTCTACTAGCAGATAAGATCCAGTAGTCATGCATATGGCAACAATGTACCGTGTGGATCTAAGAACGCGTCCTACTAACCTT
CGCATTCGTTGGTCCAGTTTGTTGTTATCGATCAACGTGACAAGGTTGTCGATTCCGCGTAAGCATGCATACCCAAGGACGCCTGTTGCAA
TTCCAAGTGAGCCAGTTCCAACAATCTTTGTAATATTAGAGCACTTCATTGTGTTGCGCTTGAAAGTAAAATGCGAACAAATTAAGAGATA
ATCTCGAAACCGCGACTTCAAACGCCAATATGATGTGCGGCACACAATAAGCGTTCATATCCGCTGGGTGACTTTCTCGCTTTAAAAAATT
```

Fig. 1Q (continued)

```
ATCCGAAAAAATTTTCTAGAGTGTTGACACTTTATACTTCCGGCTCGTATAATACGACAAGGTGTAAGGAGGACTAAACCATGGGTAAGGA
AAAGACTCACGTTTCGAGGCCGCGATTAAATTCCAACATGGATGCTGATTTATATGGGTATAAATGGGCTCGCGATAATGTCGGGCAATCA
GGTGCGACAATCTATCGATTGTATGGGAAGCCCGATGCGCCAGAGTTGTTTCTGAAACATGGCAAAGGTAGCGTTGCCAATGATGTTACAG
ATGAGATGGTCAGACTAAACTGGCTGACGGAATTTATGCCTCTTCCGACCATCAAGCATTTTATCCGTACTCCTGATGATGCATGGTTACT
CACCACTGCGATCCCCGGCAAAACAGCATTCCAGGTATTAGAAGAATATCCTGATTCAGGTGAAAATATTGTTGATGCGCTGGCAGTGTTC
CTGCGCCGGTTGCATTCGATTCCTGTTTGTAATTGTCCTTTTAACAGCGATCGCGTATTTCGTCTCGCTCAGGCGCAATCACGAATGAATA
ACGGTTTGGTTGATGCGAGTGATTTTGATGACGAGCGTAATGGCTGGCCTGTTGAACAAGTCTGGAAAGAAATGCATAAGCTTTTGCCATT
CTCACCGGATTCAGTCGTCACTCATGGTGATTTCTCACTTGATAACCTTATTTTTGACGAGGGGAAATTAATAGGTTGTATTGATGTTGGA
CGAGTCGGAATCGCAGACCGATACCAGGATCTTGCCATCCTATGGAACTGCCTCGGTGAGTTTTCTCCTTCATTACAGAAACGGCTTTTTC
AAAAATATGGTATTGATAATCCTGATATGAATAAATTGCAGTTTCATTTGATGCTCGATGAGTTTTTCTAACCTCTAGGACACCTTACGAT
TATTTAGAGAGTATTTATTAGTTTTATTGTATGTATACGGATGTTTTATTATCTATTTATGCCCTTATATTCTGTAACTATCCAAAAGTCC
TATCTTATCAAGCCAGCAATCTATGTCCGCGAACGTCAACTAAAAATAAGCTTTTTATGCTCTTCTCTCTTTTTTTCCCTTCGGTATAATT
ATACCTTGCATCCACAGATTCTCCTGCCAAATTTTGCATAATCCTTTACAACATGGCTATATGGGAGCACTTAGCGCCCTCCAAAACCCAT
ATTGCCTACGCATGTATAGGTGTTTTTTCCACAATATTTTCTCTGTGCTCTCTTTTTATTAAAGAGAAGCTCTATATCGGAGAAGCTTCTG
TGGCCGTTATATTCGGCCTTATCGTGGGACCACATTGCCTGAATTGGTTTGCCCCGGAAGATTGGGGAAACTTGGATCTGATTACCTTAGC
TGCAGGTACCACTGAGCGTCAGACCCCGTAGAAAAGATCAAAGGATCTTCTTGAGATCCTTTTTTTCTGCGCGTAATCTGCTGCTTGCAAA
CAAAAAAACCACCGCTACCAGCGGTGGTTTGTTTGCCGGATCAAGAGCTACCAACTCTTTTTCCGAAGGTAACTGGCTTCAGCAGAGCGCA
GATACCAAATACTGTTCTTCTAGTGTAGCCGTAGTTAGGCCACCACTTCAAGAACTCTGTAGCACCGCCTACATACCTCGCTCTGCTAATC
CTGTTACCAGTGGCTGCTGCCAGTGGCGATAAGTCGTGTCTTACCGGGTTGGACTCAAGACGATAGTTACCGGATAAGGCGCAGCGGTCGG
GCTGAACGGGGGGTTCGTGCACACAGCCCAGCTTGGAGCGAACGACCTACACCGAACTGAGATACCTACAGCGTGAGCTATGAGAAAGCGC
CACGCTTCCCGAAGGGAGAAAGGCGGACAGGTATCCGGTAAGCGGCAGGGTCGGAACAGGAGAGCGCACGAGGGAGCTTCCAGGGGGAAAC
GCCTGGTATCTTTATAGTCCTGTCGGGTTTCGCCACCTCTGACTTGAGCGTCGATTTTTGTGATGCTCGTCAGGGGGGCGGAGCCTATGGA
AAAACGCCAGCAACGCGGCCTTTTTACGGTTCCTGGCCTTTTGCTGGCCTTTTGCTCACATGTTCTTTCCTGCGGTACCC
```

Fig. 1 R shows the sequence of a pLLP vector containing a Geneticin resistance marker (pLLPk) corresponding to SEQ ID NO: 22.

```
AAATTTTGCATAATCCTTTACAACATGGCTATATGGGAGCACTTAGCGCCCTCCAAAACCCATATTGCCTACGCATGTATAGGTGTTTTTT
CCACAATATTTTCTCTGTGCTCTCTTTTTATTAAAGAGAAGCTCTATATCGGAGAAGCTTCTGTGGCCGTTATATTCGGCCTTATCGTGGG
ACCACATTGCCTGAATTGGTTTGCCCCGGAAGATTGGGGAAACTTGGATCTGATTACCTTAGCTGCAGGTACCACTGAGCGTCAGACCCCG
TAGAAAAGATCAAAGGATCTTCTTGAGATCCTTTTTTTCTGCGCGTAATCTGCTGCTTGCAAACAAAAAAACCACCGCTACCAGCGGTGGT
TTGTTTGCCGGATCAAGAGCTACCAACTCTTTTTCCGAAGGTAACTGGCTTCAGCAGAGCGCAGATACCAAATACTGTTCTTCTAGTGTAG
CCGTAGTTAGGCCACCACTTCAAGAACTCTGTAGCACCGCCTACATACCTCGCTCTGCTAATCCTGTTACCAGTGGCTGCTGCCAGTGGCG
ATAAGTCGTGTCTTACCGGGTTGGACTCAAGACGATAGTTACCGGATAAGGCGCAGCGGTCGGGCTGAACGGGGGGTTCGTGCACACAGCC
CAGCTTGGAGCGAACGACCTACACCGAACTGAGATACCTACAGCGTGAGCTATGAGAAAGCGCCACGCTTCCCGAAGGGAGAAAGGCGGAC
AGGTATCCGGTAAGCGGCAGGGTCGGAACAGGAGAGCGCACGAGGGAGCTTCCAGGGGGAAACGCCTGGTATCTTTATAGTCCTGTCGGGT
TTCGCCACCTCTGACTTGAGCGTCGATTTTTGTGATGCTCGTCAGGGGGCGGAGCCTATGGAAAAACGCCAGCAACGCGGCCTTTTTACG
GTTCCTGGCCTTTTGCTGGCCTTTTGCTCACATGTTCTTTCCTGCGGTACCCAGATCCAATTCCCGCTTTGACTGCCTGAAATCTCCATCG
CCTACAATGATGACATTTGGATTTGGTTGACTCATGTTGGTATTGTGAAATAGACGCAGATCGGGAACACTGAAAAATACACAGTTATTAT
TCATTTAAATCACGGTCTTGGAGTCATCAGGCTCTGACTGGGCAGCTGCTGCAACTGGAACTTCCCAAGCCTCCCACCAAACAGCAGGTGT
AGCCGAAAGTATTCACGTGTCCCAGAATGAGGCCCACAGTACATCTGTCACCGTTTCTCAACCCCCTTCAACGGTTTCTTTGCAAATTGGA
GAAGCAAATACCCTGAAATGGTCAGCTTTCTTTGGAGTAGTAGTTCCGCTGCTCAACGTACTCTTCGTTTAAAAGCCCTCCTAGGACAAAA
TGGCCAAGCTGGGAACGGGATTTGGTGGAACTTTATTATTCTTTCTACGATCCAAGCATTATGTTGTGGAACAAAGCGAATACTCTTATT
AGCTGGTAATTGAGCGAGTTGAAAAAATCAAGTCTATTGGAGGGTATGGTCAGAGTACTGATAGAGATCCCTGTTAAGATAATCGATCTTT
TTCAAATATCCAATTTCATTCCATCTTGCCCATCGGGTCTTGGCTTCTTACATCAATAATTAAAACTACTTACTCTATTAGTGCCAAAAATG
GTAAACCGTATTCAAATTGCTGCAAGCATATGCTTAAAAGGATCGCGTTGCGAGCTTCTTTTGAGATTCGCAAGCTTGATTTTATGCTCTT
GTGGGAAGAAAAGCAACCCACTGAATTCCAGATTTGTTGTGTTTTCATGCATGGACGACATACTTTGAGTAATACCGTTACTGAGATTTTA
CCGAATTCGCATTGCGTTGAGGCGTGAAGTTTCTTAATGCTGTGCCATATGGTTAAGTTGCGTTTCAAGATGGTCCACAAGTATTTTTGTA
TTTAAGCAGTGTCAATTCAAGCCTAACTGCTCATAAAAACTACACGGTTTGCTGATATCAAAACGATGCGTTTCCCATCGATTTTCACAGC
TGTTCTGTTTGCAGCTTCATCTGCTTTAGCTGCACCTGTTAACACAACTACAGAGGACGAAACGGCCCAGATCCCAGCTGAGGCAGTCATT
GGTTATTCCGATTTGGAAGGTGATTTCGATGTCGCTGTGTTACCATTCAGTAATTCCACAAATAACGGTTTGCTGTTCATTAACACCACTA
TAGCAAGCATCGCTGCAAAAGAGGAAGGTGTTTCCCTAGAAAAGAGGGCCCAGTCCGTTTGACTCAACCCCCTTCCGTATCCGCAGCTCC
AGGCCAAAAAGTAACGATCTCTTGTTCAGGTTCCACTAGTAACATAGGTGACAATTATGTGTCATGGTACCAACAGTTGCCCGGAACTGCC
CCTCAACTGCTGATCTACGACAATACCAAGAGGCCGTCAGGTATCCCAGACAGATTTTCCGGTTCTAAGAGCGGCACATCGGCTACACTAG
GTATCACGGGACTTCAAACCGGCGACGAGGCAGATTACTACTGCGCAACTTGGGATAATGATAAGTGGGGAGTTGTTTTTGGAGGTGGTAC
TAAACTCGAAGTCTTGGGTGGTGGAGGAGGATCAGGAGGAGGAGGTTCTGGAGGAGGTGGTTCATCTGGCGGTGGATCTGAAGTGCAGCTT
GTGGAGAGTGGTGGTGGTTTGGTTCAACCAGGAGGTAGCTTGAGACTGTCATGTGCCGCCAGCGGTTTTACTTTCTCTCCTATGCAATGT
CTTGGGTCAGACAAGCACCTGGTAAGGGTTTGGAATGGGTATCAGCTATTTCGGGTAGTGGTGGTTTCGACATATTATGCTGACTCCGTTAA
AGGTCGTTTTACTATTTCTAGAGACAATTCCAAAAATACCTTATATCTTCAAATGAACTCCCTTAGAGCTGAGGATACTGCTGTTTACTAC
TGTGCTCGTGATGCTTGGTTGGATGTGTTGTCTGACGGCTTTGACTACTGGGGACAAGGTACTTTGGTCACAGTGAGCAGCTGATAAGGGC
GGCCGCAGCGAATTTCTTATGATTTATGATTTTTATTATTAAATAAGTTATAAAAAAAATAAGTGTATACAAATTTTAAAGTGACTCTTAG
GTTTTAAAACGAAAATTCTTATTCTTGAGTAACTCTTTCCTGTAGGTCAGGTTGCTTTCTCAGGTATAGCATGAGGTCGCTCTTATTGACC
ACACCTCTACCGGCATGCCGAGCAAATGCCTGCAAATCGCTCCCCATTTCACCCAATTGTAGATATGCTAACTCCAGCAATGAGTTGATGA
ATCTCGGTGTGTATTTTATGTCCTCAGAGGACAAGGATCCTTCAGTAATGTCTTGTTTCTTTTGTTGCAGTGGTGAGCCATTTTGACTTCG
```

Fig. 1R (continued)

```
TGAAAGTTTCTTTAGAATAGTTGTTTCCAGAGGCCAAACATTCCACCCGTAGTAAAGTGCAAGCGTAGGAAGACCAAGACTGGCATAAATC
AGGTATAAGTGTCGAGCACTGGCAGGTGATCTTCTGAAAGTTTCTACTAGCAGATAAGATCCAGTAGTCATGCATATGGCAACAATGTACC
GTGTGGATCTAAGAACGCGTCCTACTAACCTTCGCATTCGTTGGTCCAGTTTGTTGTTATCGATCAACGTGACAAGGTTGTCGATTCCGCG
TAAGCATGCATACCCAAGGACGCCTGTTGCAATTCCAAGTGAGCCAGTTCCAACAATCTTTGTAATATTAGAGCACTTCATTGTGTTGCGC
TTGAAAGTAAAATGCGAACAAATTAAGAGATAATCTCGAAACCGCGACTTCAAACGCCAATATGATGTGCGGCACACAATAAGCGTTCATA
TCCGCTGGGTGACTTTCTCGCTTTAAAAAATTATCCGAAAAAATTTTCTAGAGTGTTGACACTTTATACTTCCGGCTCGTATAATACGACA
AGGTGTAAGGAGGACTAAACCATGGGTAAGGAAAAGACTCACGTTTCGAGGCCGCGATTAAATTCCAACATGGATGCTGATTTATATGGGT
ATAAATGGGCTCGCGATAATGTCGGGCAATCAGGTGCGACAATCTATCGATTGTATGGGAAGCCCGATGCGCCAGAGTTGTTTCTGAAACA
TGGCAAAGGTAGCGTTGCCAATGATGTTACAGATGAGATGGTCAGACTAAACTGGCTGACGGAATTTATGCCTCTTCCGACCATCAAGCAT
TTTATCCGTACTCCTGATGATGCATGGTTACTCACCACTGCGATCCCCGGCAAAACAGCATTCCAGGTATTAGAAGAATATCCTGATTCAG
GTGAAAATATTGTTGATGCGCTGGCAGTGTTCCTGCGCCGGTTGCATTCGATTCCTGTTTGTAATTGTCCTTTTAACAGCGATCGCGTATT
TCGTCTCGCTCAGGCGCAATCACGAATGAATAACGGTTTGGTTGATGCGAGTGATTTTGATGACGAGCGTAATGGCTGGCCTGTTGAACAA
GTCTGGAAAGAAATGCATAAGCTTTTGCCATTCTCACCGGATTCAGTCGTCACTCATGGTGATTTCTCACTTGATAACCTTATTTTTGACG
AGGGGAAATTAATAGGTTGTATTGATGTTGGACGAGTCGGAATCGCAGACCGATACCAGGATCTTGCCATCCTATGGAACTGCCTCGGTGA
GTTTTCTCCTTCATTACAGAAACGGCTTTTTCAAAAATATGGTATTGATAATCCTGATATGAATAAATTGCAGTTTCATTTGATGCTCGAT
GAGTTTTTCTAACCTCTAGGACACCTTACGATTATTTAGAGAGTATTTATTAGTTTTATTGTATGTATACGGATGTTTTATTATCTATTTA
TGCCCTTATATTCTGTAACTATCCAAAAGTCCTATCTTATCAAGCCAGCAATCTATGTCCGCGAACGTCAACTAAAAATAAGCTTTTTATG
CTCTTCTCTCTTTTTTTCCCTTCGGTATAATTATACCTTGCATCCACAGATTCTCCTGCC
```

Fig. 1 S shows SEQ ID NO: 23, which is part of the nuceleotide sequence of chromosome 1 of the genomic sequence of yeast strain YJK_PVA_021 after random integration of a PVA- and a Zeocin-expression cassette into the coding region of ssn6-like (reverse-complement sequence of ssn6-like) at position 807,480 of chromosome 1 of the reference strain Pichia pastoris CBS 7435. The ssn6-like sequence is underlined, the start codon is shown in bold and double-underlined (ATG → reverse-complement → CAT). Shown is the interrupted ssn6-like coding sequence including 10 nucleotide bases flanking 5' and 3' to the ssn6-like coding sequence. The sequence shown is part of the Illumina-sequenced genome of strain YJK_PVA_021 (SEQ ID NOs: 67-115) and the sequence of SEQ ID NO: 23 is part of the genomic sequence SEQ ID NO: 103 obtained by Illumina Inc. Sequences of oligo2395 (reverse-complement sequence) and oligo2398 are labeled in grey.

```
TTTCTGGTGTTCAGGGAATGGGGATTGTTGGGAAGGTGGGTACATTGGTGAAGGCGCATAGTGCTGATAGTTTTGTGGTTGAAACTGTTGC
TGCTGTTGTTGCTGTTGTTGTTGTAACTGTGGTGAAGCAGGACGAGGGGAAATTTGTGGGGGGGCAACAGGAGGATGGGTTGCAATTGAGA
ATCTCTGATCGGCGCTTGGGGACAAGTTCTTGTTTGCCGGAGCATGCACACGCTGTTGCTGTGCTAATGGAACGTTAGGGAGTGAGTGAAC
TGGTAAGTTCTGTCGCTGTGGCTGTGAATCTTCGGATGGTAGGTTATAGTTATTTGCGGAGTGAGACGGGTAGGGAGGCATTGGTCTCGAA
GTGTCAGTTCGCTTCTTGCTGCTACTCTTGATTTCTGGAGCGGATGCGATGTCATCTAACGAAGCATTGGCCAAATTTTCTCTTTCAGATA
TACTCAGTGAAGTAAGATCTCGCAGTAAATATAACGGAGATTGACAACATGTGCTTGGTCTGTAATCAGAAAGCGGAATCTCTCCAGATAC
CACTCTTCGTAAAGTTTCCAATCGCGAGTTCAAGAAATTTGCCCGAGAGCTATCACCCGCTTGGCTTGCATAGCTGCTTGACTTCATACAG
GCCTCTATAGAGTCAGCCAACTGACCATGACACTTTTCGTACACCGATGAAAGACCCTCCCAAGCAAATGAGAGCAAAATCTTGCTCTCTT
GTTCTTGTTCTGTTTCACGTTTGATGACAAACATATACGCGCTAAGGTCCTCGTCCAATCAGGTAGCCATCTCTGAAATATCTGGCTCCGT
TGCAACTCCGAACGACCTGCTGGCAACGTAAAATTCTCCGGGGTAAAACTTAAATGTGGAGTAATGGAACCAGAAACGTCTCTTCCCTTCT
CTCTCCTTCCACCGCCCGTTACCGTCCCTAGGAAATTTTACTCTGCTGGAGAGCTTCTTCTACGGCCCCCTTGCAGCAATGCTCTTCCCAG
CATTACGTTGCGGGTAAAACGGAGGTCGTGTACCCGACCTAGCAGCCCAGGGATGGAAAAGTCCCGGCCGTCGCTGGCAATAATAGCGGGC
GGACGCATGTCATGAGATTATTGGAAACCACCAGAATCGAATATAAAAGGCGAACACCTTTCCCAATTTTGGTTTCTCCTGACCCAAAGAC
TTTAAATTTAATTTATTTGTCCCTATTTCAATCAATTGAACAACTATCAAAACACAGAATTCCGAAACGATGAGATTCCCATCTATTTTCA
CCGCTGTCTTGTTCGCTGCCTCCTCTGCATTGGCTGCCCCTGTTAACACTACCACTGAAGACGAGACTGCTCAAATTCCAGCTGAAGCAGT
TATCGGTTACTCTGACCTTGAGGGTGATTTCGACGTCGCTGTTTTGCCTTTCTCTAACTCCACTAACAACGGTTTGTTGTTCATTAACACC
ACTATCGCTTCCATTGCTGCTAAGGAAGAGGGTGTCTCTCTCGAGAAGAGAGAGGCCGAAGCTGCTAGAACTACCGAGCCAATCATTGACT
TAGGATACGCTAGATACAGAGGTTCAATCAACGACACTACCTCTGTCACTTCATACCTGGGTATCAGATTTGCTGAACCTCCAGTTGAGGA
CTTGAGATGGAGAGCCCCACAACCTGCTAAGAGACTTCCTGGTGTTCAAAACGCCACTATTGTTCCTCCATTGTGTCCACAAGGTTTCATC
AACATCTTGATTCCAGGAGGTATTCCACCTCCAGATTCGACCAACGTTTCTGAAGACTGCTTGTTCTTGTCCGTTTTTGCACCTAGAAAGT
TGCCACCTAAGCGTAAGGAATTGCCAGTGATTGTTTGGATTCATGGTGGAGGATACATCGTCTCCTCTGCAGCTACTTTCGACGGAACTAA
CTTGGTTAGAGAGTCTAACGACTCTGTCATTGTGGTGACTATCCAGTACAGACTGGGAATTTTCGGATTCATGGCTGGTAAGAAGTTGAAG
GATAACGGAGACTTGAATGCTGGATTGCTTGACCAAGAGTTGGCTTTGAAGTGGGTTCAACAGCACATTAACAAGTTCGGTGGTGACCCTA
AGCAAGTGACCATTTGGGGTCAATCAGCTGGAGGTGGTTCTGTGTTGCAACAGGTCATTGCTCACAACGGACAAACTAACCCACCATTGTT
CAGAGCTGCTATGTCTTCCTCTACCTACCTTCCTTCTCAACACCATTTCGACGATCCTGTTCCAGAAGGTATCTACTCTACCGTTGTCTCA
ACTGCTGGTTGTGCTGATGCTACTGATCCTCTTACTTGCTTGAGAGCTTCTAACACCTCCATCTTACAAGCTGCTAACGACAAGGCATGTA
```

Fig. 1S (continued)

```
GATCCGCATTCTACGGTACTTCCGTTGTTGTTCCTGTTGTTGATGGTGAGTTCATCACCCAAAGACCATCTGAAGCTCTTAGACAAAGACG
TGTCAACGGTAACGCTTTGTTGGCTATCTCTAATACCAACGAAGGTGACATCTTCGTTGACCAATCTAAGGCTGACACTGTTACTGCTGCT
CAGTTCGTTAGAGACTTGTACCCTAGATTGAACGGTGCTCAAGTTGCTGAGGTTGTTCGTCTGTACTCTGGTTTAGGTGCTCCAATCCAAC
AGGCTGACTCTATCATGGGAGATACTCTGTTCCAATGTCCAACCATTTGGTTCTCTCAAGCCTTCAGACAATCTTTCAAGGGTGAATACGC
TGTTCTTCCTGCATTCCACGGTTCTGACATTTCCCAGTACTTCCCATCTTTTGCTCCTAGATTCTTCGACGATCCTGCTTTCACTTCCTCT
TTCACTCAGTCCTTCTTGGACTTCGCTTTGTCTCGTAACTCTGATCCTAACGCAAAGTTTGACGACGGTAACTTGACTCCTAGATGGAACA
GATACACCTCTTGCTCAAAGTTCGAGATGGTGTTCAACCGTACTGATGGTGAAGAGTTGGACATTAGACCAGCTTCTACTGGTGCTGGTTT
GTTGGAGAGATGTGCATTCTGGGAATCTGTCTCCGAATTGACTGCTCAATAAGCGGCCGCTCAAGAGGATGTCAGAATGCCATTTGCCTGA
GAGATGCAGGCTTCATTTTTGATACTTTTTTATTTGTAACCTATATAGTATAGGATTTTTTTTGTCATTTTGTTTCTTCTCGTACGAGCTT
GCTCCTGATCAGCCTATCTCGCAGCAGATGAATATCTTGTGGTAGGGGTTTGGGAAAATCATTCGAGTTTGATGTTTTTCTTGGTATTTCC
CACTCCTCTTCAGAGTACAGAAGATTAAGTGAGACCTTCGTTTGTGCGGATCCTTCAGTAATGTCTTGTTTCTTTTGTTGCAGTGGTGAGC
CATTTTGACTTCGTGAAAGTTTCTTTAGAATAGTTGTTTCCAGAGGCCAAACATTCCACCCGTAGTAAAGTGCAAGCGTAGGAAGACCAAG
ACTGGCATAAATCAGGTATAAGTGTCGAGCACTGGCAGGTGATCTTCTGAAAGTTTCTACTAGCAGATAAGATCCAGTAGTCATGCATATG
GCAACAATGTACCGTGTGGATCTAAGAACGCGTCCTACTAACCTTCGCATTCGTTGGTCCAGTTTGTTGTTATCGATCAACGTGACAAGGT
TGTCGATTCCGCGTAAGCATGCATACCCAAGGACGCCTGTTGCAATTCCAAGTGAGCCAGTTCCAACAATCTTTGTAATATTAGAGCACTT
CATTGTGTTGCGCTTGAAAGTAAAATGCGAACAAATTAAGAGATAATCTCGAAACCGCGACTTCAAACGCCAATATGATGTGCGGCACACA
ATAAGCGTTCATATCCGCTGGGTGACTTTCTCGCTTTAAAAAATTATCCGAAAAAATTTTCTAGAGTGTTGTTACTTTATACTTCCGGCTC
GTATAATACGACAAGGTGTAAGGAGGACTAAACCATGGCTAAACTCACCTCTGCTGTTCCAGTCCTGACTGCTCGTGATGTTGCTGGTGCT
GTTGAGTTCTGGACTGATAGACTCGGTTTCTCCCGTGACTTCGTAGAGGACGACTTTGCCGGTGTTGTACGTGACGACGTTACCCTGTTCA
TCTCCGCAGTTCAGGACCAGGTTGTGCCAGACAACACTCTGGCATGGGTATGGGTTCGTGGTCTGGACGAACTGTACGCTGAGTGGTCTGA
GGTCGTGTCTACCAACTTCCGTGATGCATCTGGTCCAGCTATGACCGAGATCGGTGAACAGCCCTGGGGTCGTGAGTTTGCACTGCGTGAT
CCAGCTGGTAACTGCGTGCATTTCGTCGCAGAAGAGCAGGACTAACAATTGACACCTTACGATTATTTAGAGAGTATTTATTAGTTTTATT
GTATGTATACGGATGTTTTATTATCTATTTATGCCCTTATATTCTGTAACTATCCAAAAGTCCTATCTTATCAAGCCAGCAATCTATGTCC
GCGAACGTCAACTAAAAATAAGCTTTTTATGCTCTTCTCTCTTTTTTTCCCTTCGGTATAATTATACCTTGCATCCACAGATTCTCCTGCC
AAATTTTGCATAATCCTTTACAACATGGCTATATGGGAGCACTTAGCGCCCTCCAAAACCCATATTGCCTACGCATGTATAGGTGTTTTTT
CCACAATATTTTCTCTGTGCTCTCTTTTTATTAAAGAGAAGCTCTATATCGGAGAAGCTTCTGTGGCCGTTATATTCGGCCTTATCGTGGG
ACCACATTGCCTGAATTGGTTTGCCCCGGAAGATTGGGGAAACTTGGATCTGATTACCTTAGCTGCAGGTACCACTCATCAGCCAGCTGGC
CCAGTTCGGCATAAAGGTTTCCCACTGCAAGCCATACAATTGTGTGGTTTGGAGCCCTTTTCAAGGCCAACTGGAATGCTTCGTAGGCCTC
GCTTGGTTGGCGCAGCATTTGATAAGCCTCACCAAGTAAAAACCATGGTAGAAAGTCGTTGCTTTCCGAATTAACAACTTGCCGAAGCAGG
ACACAAGCAGACTGTGGGTTAAATACGTGACTGTTCGGTAGTAGCAACAAGTATGCGTGGCATATATATATGCATGGCTCGAATCCTAACA
GTCCAGATGCCTCCTCACAGACGCGCACTGCCTTGGCCATATCTCCAAGGCGCTCATTAGCACTAATGAGGGCGCACCAAAGAGAGGAATA
CTCTGTGAAGCGGGAAGAAGAGGGAGGCGGAAGAGCCAAAGTGGCCTCCAACTCATCCCTGGCAGCTTCGATGTTGCCCTCCGCAGCAAGA
ACGGAGGCAAATTCTGAGTGGGTGGAACGGGCCACGTCAATCTCTTCTTTTGTATAGTCTGCAAGTCGATTTGGGGAGTTTCACCAAGGCTG
TGTTCAGTGCATCGACGGCCTCATGTTTGGAACCTGCGGCCATCAATGTTTGTCCTTTAAGTAACCATAATGCAGAGTTGTTGGGAGTTAA
TTGAATACATCTTTGTAGGGCCTCCATGGCATTCGTTGTGTTGTTTAAGAGTAGATAGCATTCGGCAGCTTCTCTCCAGATAGATGGATCT
TTGTAAAGCTCTGATGAGCGTGATAAAAGGTCGTTGATAACATCCAGGGCCGCTGCGGTACCGTCTGTTTGGTCCTTGACCAGATCCATAG
CCCTCAATGCAGCTGCGAGTCCACAAAGAGCCTTCTCGTTGAATGGATCATTTTGGAGGGCAAAATCGAACGAATCAATTGCCAGCTGGTA
CAAGTGGACTTCGTGAGCCATGGATCCGAGCGCTAGCCAAGTGGAGACAGCTATCTTGCGAAACTCGAGTTGTTTATCATATACCACTTTC
CGTTGCTGGGAGTCAGCTTGAGACGTTGGTACGGGATCATGCCTCACTTCCAGTGTCACTGGCGGAGGCTGTGAAGGTTCGTTCATAAGTA
GTGGT
```

Fig. 1 T shows SEQ ID NO: 121, which is the codon-optimized human serum albumin (HSA) sequence with its natural signal sequence exchanged by the LLP-signal sequence. The LLP-signal sequence is underlined. Position 45 (labeled in bold and with grey background color) contains a silent mutation from G to C.

```
ATGTTTGAAGAAGAGTAAATTTGTGGTTTCGTTTCTGCTTTTACTCCAGCTATTTTGTGTCCTTGGTGTACATGGAGACGCACACAAGAGCG
AAGTGGCTCATCGTTTCAAAGATCTGGGTGAAGAGAATTTCAAAGCATTGGTGTTGATTGCATTTGCACAATACCTTCAACAATGTCCATT
TGAGGACCACGTCAAACTTGTGAATGAAGTGACAGAGTTTGCTAAAACTTGCGTTGCTGACGAGTCCGCAGAGAATTGCGACAAGTCTTTA
CATACTCTGTTCGGAGATAAGCTGTGTACAGTTGCCACCTTGAGAGAGACTTACGGCGAAATGGCTGACTGTTGCGCTAAACAGGAACCCG
AGAGAAACGAATGTTTTCTGCAACATAAGGATGATAACCCTAATTTGCCAAGGTTAGTACGTCCTGAGGTTGATGTCATGTGTACAGCTTT
TCATGACAATGAGGAAACTTTCTTGAAAAAGTACCTGTACGAGATCGCAAGACGTCACCCATACTTCTACGCTCCAGAACTCCTGTTTTTC
GCTAAGAGATATAAGGCAGCATTCACGGAGTGTTGTCAGGCCGCTGACAAAGCTGCTTGCTTGTTACCTAAGCTTGACGAGTTGAGAGATG
AAGGAAAAGCCTCATCAGCTAAGCAAAGACTAAAATGCGCATCTCTTCAAAAGTTTGGTGAAAGAGCTTTCAAAGCTTGGGCCGTTGCTAG
GCTCTCTCAAAGATTCCCCAAGGCTGAATTTGCTGAAGTCTCTAAGCTTGTAACAGATCTAACTAAAGTCCACACTGAATGCTGTCATGGA
GATCTGCTAGAATGCGCGGACGACAGAGCTGACTTGGCTAAATACATTTGTGAAAATCAGGATTCGATCAGTTCGAAACTCAAAGAGTGTT
GTGAGAAGCCACTATTGGAGAAATCCCATTGCATCGCTGAAGTCGAAAATGACGAAATGCCGGCTGACTTGCCTAGTCTTGCAGCAGATTT
CGTAGAATCAAAGGATGTATGTAAAAACTACGACCGAAGCAAAAGACGTGTTTTTGGGCATGTTTCTGTATGAATATGCCAGGAGACACCCA
GATTATTCCGTAGTTTTGTTGCTGCGTTTGGCTAAGACTTATGAGACAACGTTAGAAAAGTGCTGTGCTGCCGCCGACCCACATGAATGTT
ATGCCAAAGTTTTTGATGAGTTCAAGCCATTGGTTGAGGAACCTCAAAACTTGATAAAACAAAATTGTGAATTGTTTGAACAATTGGGTGA
GTACAAATTTCAAAATGCATTGCTGGTAAGATACACCAAAAAGGTTCCTCAGGTTTCCACCCCTACTCTAGTCGAGGTTTCCAGAAACTTG
GGAAAGGTGGGTTCTAAGTGTTGTAAACACCCCGAGGCCAAACGTATGCCCTGTGCTGAAGATTACTTGAGCGTCGTTCTCAACCAATTAT
GTGTGCTGCATGAAAGACGCCAGTTTCCGATCGAGTCACCAAGTGCTGTACTGAGTCTTTGGTAAATCGTAGACCTTGTTTCTCAGCATT
AGAAGTGGACGAGACTTATGTGCCGAAGGAATTCAATGCTGAAACATTTACTTTTCATGCTGATATTTGTACATTGTCAGAAAAAGAGAGA
CAAATCAAAAAGCAGACTGCCTTGGTGGAGCTTGTTAAACACAAGCCAAAGGCTACTAAAGAGCAATTGAAAGCAGTTATGGATGATTTTG
```

Fig. 1T (continued)

```
CAGCATTCGTTGAGAAATGTTGCAAGGCAGACGACAAGGAGACATGTTTTGCCGAGGAGGGTAAAAAGCTTGTTGCAGCTAGCCAGGCTGC
TTTGGGACTTTAA
```

Fig. 1 U shows SEQ ID NO: 129, which is the shortened LLP-promoter sequence delta29 corresponding to a 576 bases length of the shortened LLP-promoter

```
TGGTGGAACTTTATTATTCTTTCTACGATCCAAGCATTATGTTGTGGAACAAAGCGAATACTCTTATTAGCTGGTAATTGAGCGAGTTGAA
AAAATCAAGTCTATTGGAGGGTATGGTCAGAGTACTGATAGAGATCCCTGTTAAGATAATCGATCTTTTTCAAATATCCAATTTCATTCCA
TCTTGCCATCGGGTCTTGGCTTCTTACATCAATAATTAAAACTACTTACTCTATTAGTGCCAAAAATGGTAAACCGTATTCAAATTGCTGC
AAGCATATGCTTAAAAGGATCGCGTTGCGAGCTTCTTTTGAGATTCGCAAGCTTGATTTTATGCTCTTGTGGGAAGAAAAGCAACCCACTG
AATTCCAGATTTGTTGTGTTTTCATGCATGGACGACATACTTTGAGTAATACCGTTACTGAGATTTTACCGAATTCGCATTGCGTTGAGGC
GTGAAGTTTCTTAATGCTGTGCCATATGGTTAAGTTGCGTTTCAAGATGGTCCACAAGTATTTTTGTATTTAAGCAGTGTCAATTCAAGCC
TAACTGCTCATAAAAACTACACGGTTTGCT
```

Fig. 1 V shows SEQ ID NO: 130, which is the shortened LLP-promoter sequence delta93 corresponding to a 512 bases length of the shortened LLP-promoter

```
TATTAGCTGGTAATTGAGCGAGTTGAAAAAATCAAGTCTATTGGAGGGTATGGTCAGAGTACTGATAGAGATCCCTGTTAAGATAATCGAT
CTTTTTCAAATATCCAATTTCATTCCATCTTGCCATCGGGTCTTGGCTTCTTACATCAATAATTAAAACTACTTACTCTATTAGTGCCAAA
AATGGTAAACCGTATTCAAATTGCTGCAAGCATATGCTTAAAAGGATCGCGTTGCGAGCTTCTTTTGAGATTCGCAAGCTTGATTTTATGC
TCTTGTGGGAAGAAAAGCAACCCACTGAATTCCAGATTTGTTGTTTTCATGCATGGACGACATACTTTGAGTAATACCGTTACTGAGAT
TTTACCGAATTCGCATTGCGTTGAGGCGTGAAGTTTCTTAATGCTGTGCCATATGGTTAAGTTGCGTTTCAAGATGGTCCACAAGTATTTT
TGTATTTAAGCAGTGTCAATTCAAGCCTAACTGCTCATAAAAACTACACGGTTTGCT
```

Fig. 1 W shows SEQ ID NO: 131, which is the shortened LLP-promoter sequence delta133 corresponding to a 472 bases length of the shortened LLP-promoter

```
TTGGAGGGTATGGTCAGAGTACTGATAGAGATCCCTGTTAAGATAATCGATCTTTTTCAAATATCCAATTTCATTCCATCTTGCCATCGGG
TCTTGGCTTCTTACATCAATAATTAAAACTACTTACTCTATTAGTGCCAAAAATGGTAAACCGTATTCAAATTGCTGCAAGCATATGCTTA
AAAGGATCGCGTTGCGAGCTTCTTTTGAGATTCGCAAGCTTGATTTTATGCTCTTGTGGGAAGAAAAGCAACCCACTGAATTCCAGATTTG
TTGTGTTTTCATGCATGGACGACATACTTTGAGTAATACCGTTACTGAGATTTTACCGAATTCGCATTGCGTTGAGGCGTGAAGTTTCTTA
ATGCTGTGCCATATGGTTAAGTTGCGTTTCAAGATGGTCCACAAGTATTTTTGTATTTAAGCAGTGTCAATTCAAGCCTAACTGCTCATAA
AAACTACACGGTTTGCT
```

Fig. 1 X shows SEQ ID NO: 132, which is the shortened LLP-promoter sequence delta201 corresponding to a 404 bases length of the shortened LLP-promoter

```
TTTCATTCCATCTTGCCATCGGGTCTTGGCTTCTTACATCAATAATTAAAACTACTTACTCTATTAGTGCCAAAAATGGTAAACCGTATTC
AAATTGCTGCAAGCATATGCTTAAAAGGATCGCGTTGCGAGCTTCTTTTGAGATTCGCAAGCTTGATTTTATGCTCTTGTGGGAAGAAAAG
CAACCCACTGAATTCCAGATTTGTTGTGTTTTCATGCATGGACGACATACTTTGAGTAATACCGTTACTGAGATTTTACCGAATTCGCATT
GCGTTGAGGCGTGAAGTTTCTTAATGCTGTGCCATATGGTTAAGTTGCGTTTCAAGATGGTCCACAAGTATTTTTGTATTTAAGCAGTGTC
AATTCAAGCCTAACTGCTCATAAAAACTACACGGTTTGCT
```

Fig. 1 Y shows SEQ ID NO: 133, which is the shortened LLP-promoter sequence delta233 corresponding to a 372 bases length of the shortened LLP-promoter

```
CTTACATCAATAATTAAAACTACTTACTCTATTAGTGCCAAAAATGGTAAACCGTATTCAAATTGCTGCAAGCATATGCTTAAAAGGATCG
CGTTGCGAGCTTCTTTTGAGATTCGCAAGCTTGATTTTATGCTCTTGTGGGAAGAAAAGCAACCCACTGAATTCCAGATTTGTTGTGTTTT
CATGCATGGACGACATACTTTGAGTAATACCGTTACTGAGATTTTACCGAATTCGCATTGCGTTGAGGCGTGAAGTTTCTTAATGCTGTGC
CATATGGTTAAGTTGCGTTTCAAGATGGTCCACAAGTATTTTTGTATTTAAGCAGTGTCAATTCAAGCCTAACTGCTCATAAAAACTACAC
GGTTTGCT
```

Fig. 1 Z shows SEQ ID NO: 134, which is the shortened LLP-promoter sequence delta300 corresponding to a 305 bases length of the shortened LLP-promoter

```
GCAAGCATATGCTTAAAAGGATCGCGTTGCGAGCTTCTTTTGAGATTCGCAAGCTTGATTTTATGCTCTTGTGGGAAGAAAAGCAACCCAC
TGAATTCCAGATTTGTTGTGTTTTCATGCATGGACGACATACTTTGAGTAATACCGTTACTGAGATTTTACCGAATTCGCATTGCGTTGAG
GCGTGAAGTTTCTTAATGCTGTGCCATATGGTTAAGTTGCGTTTCAAGATGGTCCACAAGTATTTTTGTATTTAAGCAGTGTCAATTCAAG
CCTAACTGCTCATAAAAACTACACGGTTTGCT
```

Fig. 2: Amino acid sequences

Fig. 2 A shows the amino acid sequence of the SSN6-like protein of P. Pastoris (SEQ ID NO: 8)

```
MNEPSQPPPVTLEVRHDPVPTSQADSQQRKVVYDKQLEFRKIAVSTWLALGSMAHEVHLYQLAIDSFDFALQNDPFNEKALCGLAAALRAM
DLVKDQTDGTAAALDVINDLLSRSSELYKDPSIWREAAECYLLLNNTTNAMEALQRCIQLTPNNSALWLLKGQTLMAAGSKHEAVDALNTA
LVKLPNDVADYTKEEIDVARSTHSEFASVLAAEGNIEAARDELEATLALPPPSSSRFTEYSSLWCALISANERLGDMAKAVRVCEEASGLL
GFEPCIYICHAYLLLLPNSHVFNPQSACVLLRQVVNSESNDFLPWFLLGEAYQMLRQPSEAYEAFQLALKRAPNHTIVWLAVGNLYAELGQ
LADALSAYMFVIKRETEQEQESKILLSFAWEGLSSVYEKCHGQLADSIEACMKSSSYASQAGDSSRANFLNSRLETLRRVVSGEIPLSDYR
PSTCCQSPLYLLRDLTSLSISERENLANASLDDIASAPEIKSSSKKRTDTSRPMPPYPSHSANNYNLPSEDSQPQRQNLPVHSLPNVPLAQ
QQRVHAPANKNLSPSADQRFSIATHPPVAPPTNFPSSCFTTVTTTTATTAATVSTTKLSALCAFTNVPTFPTIPIP
```

Fig. 2 B shows the amino acid sequence of the SSN6-like modified protein of P. Pastoris YJK_PVA_021 (SEQ ID NO: 9)

```
MNEPSQPPPVTLEVRHDPVPTSQADSQQRKVVYDKQLEFRKIAVSTWLALGSMAHEVHLYQLAIDSFDFALQNDPFNEKALCGLAAALRAM
DLVKDQTDGTAAALDVINDLLSRSSELYKDPSIWREAAECYLLLNNTTNAMEALQRCIQLTPNNSALWLLKGQTLMAAGSKHEAVDALNTA
LVKLPNDVADYTKEEIDVARSTHSEFASVLAAEGNIEAARDELEATLALPPPSSSRFTEYSSLWCALISANERLGDMAKAVRVCEEASGLL
GFEPCIYICHAYLLLLPNSHVFNPQSACVLLRQVVNSESNDFLPWFLLGEAYQMLRQPSEAYEAFQLALKRAPNHTIVWLAVGNLYAELGQ
LADEWYLQLR
```

Fig. 2 C shows the amino acid sequence of the LLP protein including LLP signal sequence of P. Pastoris (SEQ ID NO: 10). The LLP signalsequnce is underlined.

```
MFEKSKFVVSFLLLLQLFCVLGVHGQESGNGTTSDTAYACDIGATPFDGFNATIYQYQASDDNSIQDPVFMSTGYLQRNQLHSTTGVTNPG
FNIFTAGVATTTLYGIPNVNYQNMLLELKGYFRADASGNYGLSLRNIDDSAILFFGRETAFECCNENLIPLDEAPTDYSLFTIKEGEASTN
PDSYTYTQYLEAGRYYPVRTFFANIRTRAVFNFTMTLPDGSELTDFQNYIFQFGALNQQQCQAEIVTRENYTTTTEPWTGTFEATTTVIPS
GTEPGTVIVQTPYSTIDSTSTWTGTFTTFTTDADGSTIAVVPSSTIDDHFASTETVLTDTAISTTVITVTSCGTSKCTKTTALTGVTQRTL
TIDDRTTVVTTYCPLPTDVATIKTASVSGSEVVQTIYTAKHSQAVSYVHPSTVTITREVCDAQTCTQATIVTGEILQTTVVDSGSTTVVPK
YVPVETHEPTFELSTL
```

Fig. 2 D shows the amino acid sequence of the LLP signal sequence of P. Pastoris (SEQ ID NO: 140)

MFEKSKFVVSFLLLLQLFCVLGVHG

Fig. 3: Mechanism of the super-secretor strain 1
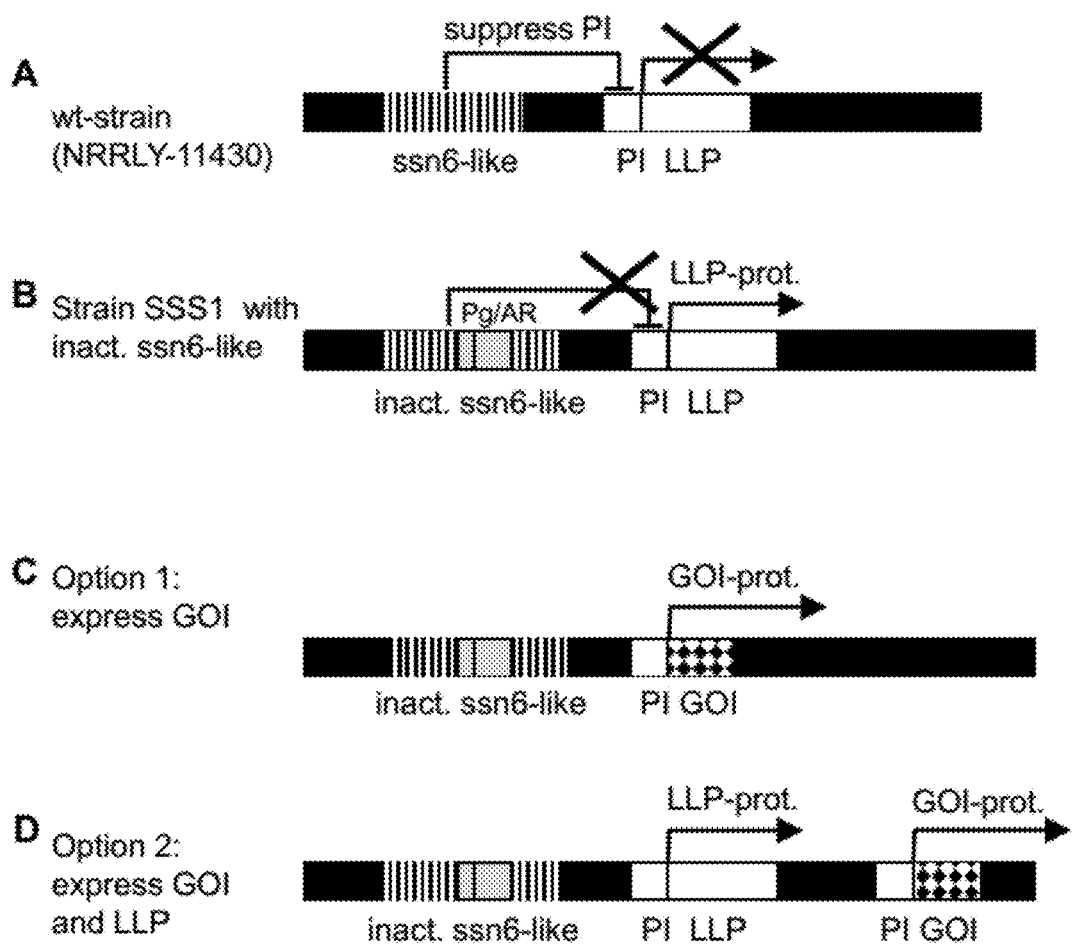

Fig. 7
7 A
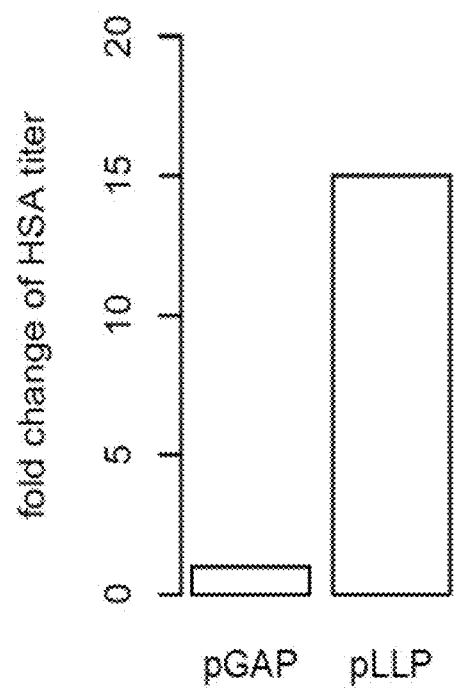
7 B
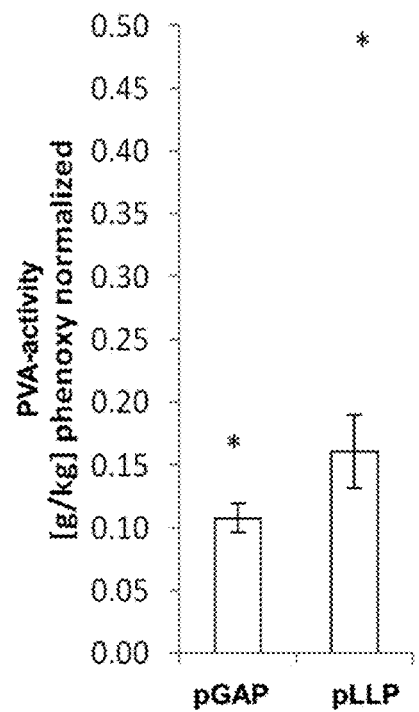

Fig. 8
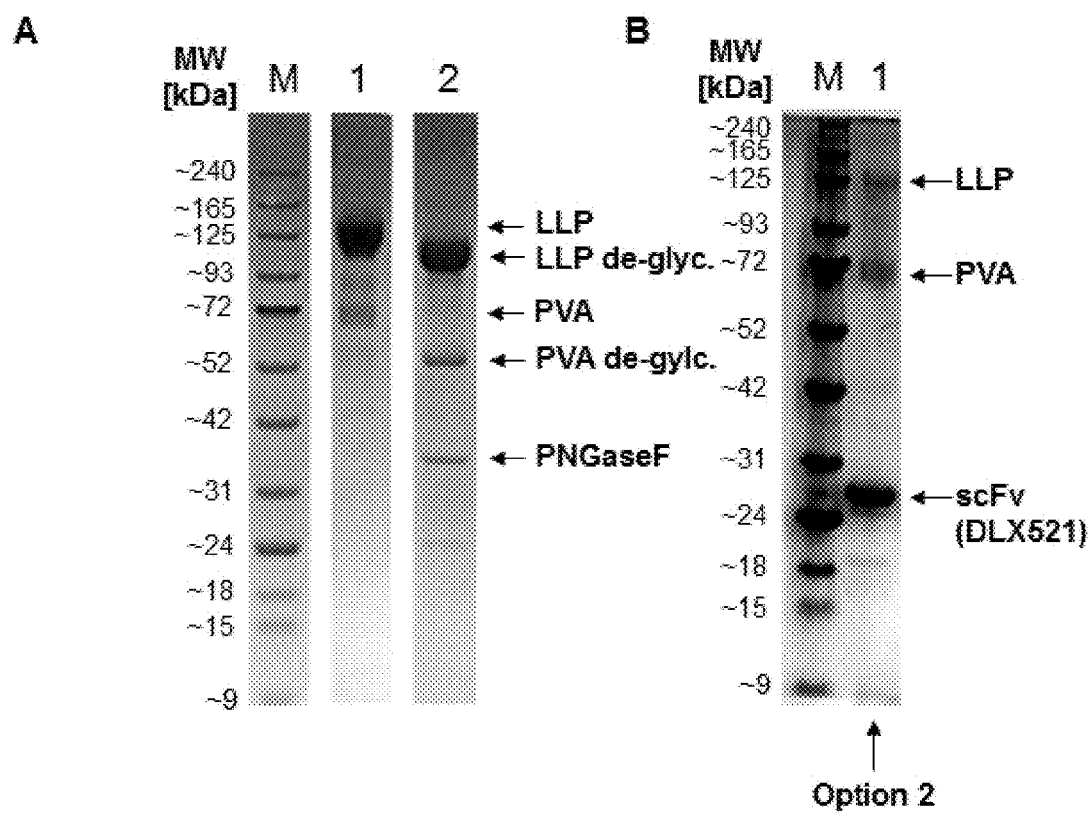
| Lane | M | 1 | 2 | | M | 1 |
|---|---|---|---|---|---|---|
| LLP, glycos. | | ++ | - | | | + |
| LLP, de-glycos. | | - | ++ | | | - |
| PVA, glycos. | | + | o | | | + |
| PVA, de-glycos. | | - | ++ | | | - |
| scFv, glycos. | | - | - | | | ++ |
| PNGaseF added | | no | yes | | | no |
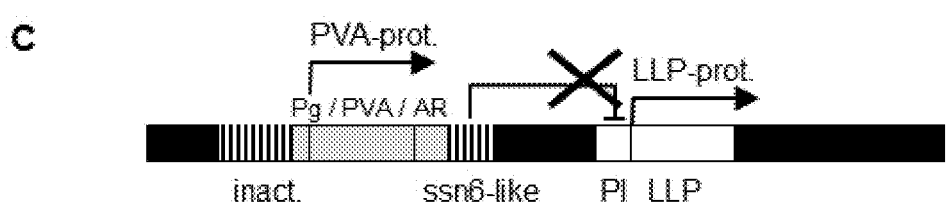

Pichia SSN6-like: WLAVGNLYAELGQLADALSAY
          352  355   360   365   370 372

Consensus Sequence 1:
W(CGL)(SLTA)(IMV)G(VINSTK)LY(YFLA)(QNSRKE)(INLM)
352         355              360
(GNSKR)Q(NFYL)(HRETPAK)D(AST)(LI)(DGTNASE)(AV)(YF)
   365                        370        372

C

Pichia SSN6-like: WEGLSSVYEKCHGQLADSIEACMK
         394   400   405   410  415 417

Consensus Sequence 2:
W(YFLED)(NDG)L(GLAS)(TSIQC)(LIV)YE(TSARKQ)(CS)
394                     400
(NHSDEH)(DNK-RGF)(Q-H)(ILTHVAS)(TSNQERIAMG)D
   405                                    410
(ASV)(LIASC)(DHNE)(SA)(YC)(EAKRQMTLNDS)(RQK)
            415                    417

A: Expression vector pLLP

Fig. 10 (continued)
B: Full sequence of pLLP (SEQ ID NO: 65)

LLP-promoter, LLP-terminator, NotI, EcoRV, AvrII

AAATTTTGCATAATCCTTTACAACATGGCTATATGGGAGCACTTAGCGCCCTCCAAAACCCATATTGCCTACGCATGTATAGGTGTTTTTT
CCACAATATTTTCTCTGTGCTCTCTTTTTATTAAAGAGAAGCTCTATATCGGAGAAGCTTCTGTGGCCGTTATATTCGGCCTTATCGTGGG
ACCACATTGCCTGAATTGGTTTGCCCCGGAAGATTGGGGAAACTTGGATCTGATTACCTTAGCTGCAGGTACCACTGAGCGTCAGACCCCG
TAGAAAAGATCAAAGGATCTTCTTGAGATCCTTTTTTTCTGCGCGTAATCTGCTGCTTGCAAACAAAAAAACCACCGCTACCAGCGGTGGT
TTGTTTGCCGGATCAAGAGCTACCAACTCTTTTTCCGAAGGTAACTGGCTTCAGCAGAGCGCAGATACCAAATACTGTTCTTCTAGTGTAG
CCGTAGTTAGGCCACCACTTCAAGAACTCTGTAGCACCGCCTACATACCTCGCTCTGCTAATCCTGTTACCAGTGGCTGCTGCCAGTGGCG
ATAAGTCGTGTCTTACCGGGTTGGACTCAAGACGATAGTTACCGGATAAGGCGCAGCGGTCGGGCTGAACGGGGGGTTCGTGCACACAGCC
CAGCTTGGAGCGAACGACCTACACCGAACTGAGATACCTACAGCGTGAGCTATGAGAAAGCGCCACGCTTCCCGAAGGGAGAAAGGCGGAC
AGGTATCCGGTAAGCGGCAGGGTCGGAACAGGAGAGCGCACGAGGGAGCTTCCAGGGGGAAACGCCTGGTATCTTTATAGTCCTGTCGGGT
TTCGCCACCTCTGACTTGAGCGTCGATTTTTGTGATGCTCGTCAGGGGGGCGGAGCCTATGGAAAAACGCCAGCAACGCGGCCTTTTTACG
GTTCCTGGCCTTTTGCTGGCCTTTTGCTCACATGTTCTTTCCTGCGGTACCCAGATCCAATTCCCGCTTTGACTGCCTGAAATCTCCATCG
CCTACAATGATGACATTTGGATTTGGTTGACTCATGTTGGTATTGTGAAATAGACGCAGATCGGGAACACTGAAAAATACACAGTTATTAT
TCATTTAAATC<u>ACGGTCTTGGAGTCATCAGGCTCTGACTGGGCAGCTGCTGCAACTGGAACTTCCCAAGCCTCCCACCAAACAGCAGGTGT
AGCCGAAAGTATTCACGTGTCCCAGAATGAGGCCCACAGTACATCTGTCACCGTTTCTCAACCCCCTTCAACGGTTTCTTTGCAAATTGGA
GAAGCAAATACCCTGAAATGGTCAGCTTTCTTTGGAGTAGTAGTTCCGCTGCTCAACGTACTCTTCGTTTAAAAGCCCT</u>CCTAGG*ACAAAA
TGGCC*AAGCTGGGAAACGGGATT*TGGTGGAACTTT*ATTATTCTTTCTACGATCCAAGCATTATGTTGTGGAACAAAGCGAATACTCT*TATT
AGCTGG*TAATTGAGCGAGTTGAAAAAATCAAGTCTA*TTGGAGGGT*ATGGTCAGAGTACTGATAGAGATCCCTGTTAAGATAATCGATCTTT
TTCAAATATCCAATTTCATTCCATCTTGCCATCGGGTCTTGGCTT*CTTACAT*CAATAATTAAAACTACTTACTCTATTAGTGCCAAAAATG
GTAAACCGTATTCAAATTGCTGCAAGCATATGCTTAAAAGGATCGCGTTGCGAGCTTCTTTTGAGATTCGCAAGCTTGATTTTATGCTCTT
GTGGGAAGAAAAGCAACCCACTGAATTCCAGATTTGTTGTGTTTTCATGCATGGACGACATACTTTGAGTAATACCGTTACTGAGATTTTA
CCGAATTCGCATTGCGTTGAGGCGTGAAGTTTCTTAATGCTGTGCCATATGGTTAAGTTGCGTTTCAAGATGGTCCACAAGTATTTTTGTA
TTTAAGCAGTGTCAATTCAAGCCTAACTGCTCATAAAAACTACACGGTTTGCTGATATCAAAACGATGTAAGGGCGGCCGCAGCGAATTTC
TTATGATTTATGATTTTTATTATTAAATAAGTTATAAAAAAAATAAGTGTATACAAATTTTAAAGTGACTCTTAGGTTTTAAAACGAAAAT
TCTTATTCTTGAGTAACTCTTTCCTGTAGGTCAGGTTGCTTTCTCAGGTATAGCATGAGGTCGCTCTTATTGACCACACCTCTACCGGCAT
GCCGAGCAAATGCCTGCAAATCGCTCCCCATTTCACCCAATTGTAGATATGCTAACTCCAGCAATGAGTTGATGAATCTCGGTGTGTATTT
TATGTCCTCAGAGGACAAGGATCCTTCAGTAATGTCTTGTTTCTTTTGTTGCAGTGGTGAGCCATTTTGACTTCGTGAAAGTTTCTTTAGA
ATAGTTGTTTCCAGAGGCCAAACATTCCACCCGTAGTAAAGTGCAAGCGTAGGAAGACCAAGACTGGCATAAATCAGGTATAAGTGTCGAG
CACTGGCAGGTGATCTTCTGAAAGTTTCTACTAGCAGATAAGATCCAGTAGTCATGCATATGGCAACAATGTACCGTGTGGATCTAAGAAC
GCGTCCTACTAACCTTCGCATTCGTTGGTCCAGTTTGTTGTTATCGATCAACGTGACAAGGTTGTCGATTCCGCGTAAGCATGCATACCCA
AGGACGCCTGTTGCAATTCCAAGTGAGCCAGTTCCAACAATCTTTGTAATATTAGAGCACTTCATTGTGTTGCGCTTGAAAGTAAAATGCG
AACAAATTAAGAGATAATCTCGAAACCGCGACTTCAAACGCCAATATGATGTGCGGCACACAATAAGCGTTCATATCCGCTGGGTGACTTT
CTCGCTTTAAAAAATTATCCGAAAAAATTTTCTAGAGTGTTGACACTTTATACTTCCGGCTCGTATAATACGACAAGGTGTAAGGAGGACT
AAACCATGGCTAAACTCACCTCTGCTGTTCCAGTCCTGACTGCTCGTGATGTTGCTGGTGCTGTTGAGTTCTGGACTGATAGACTCGGTTT
CTCCCGTGACTTCGTAGAGGACGACTTTGCCGGTGTTGTACGTGACGACGTTACCCTGTTCATCTCCGCAGTTCAGGACCAGGTTGTGCCA
GACAACACTCTGGCATGGGTATGGGTTCGTGGTCTGGACGAACTGTACGCTGAGTGGTCTGAGGTCGTGTCTACCAACTTCCGTGATGCAT
CTGGTCCAGCTATGACCGAGATCGGTGAACAGCCCTGGGGTCGTGAGTTTGCACTGCGTGATCCAGCTGGTAACTGCGTGCATTTCGTCGC
AGAAGAGCAGGACTAACCTCTAGGACACCTTACGATTATTTAGAGAGTATTTATTAGTTTTATTGTATGTATACGGATGTTTTATTATCTA
TTTATGCCCTTATATTCTGTAACTATCCAAAAGTCCTATCTTATCAAGCCAGCAATCTATGTCCGCGAACGTCAACTAAAAATAAGCTTTT
TATGCTCTTCTCTCTTTTTTTCCCTTCGGTATAATTATACCTTGCATCCACAGATTCTCCTGCC

A: Expression vector pGAP with DLX521 as GOI

Fig. 11 (continued)

B: Full sequence of pGAP with DLX521 as GOI (SEQ ID NO: 66)

```
TCCAAAACCCATATTGCCTACGCATGTATAGGTGTTTTTTCCACAATATTTTCTCTGTGCTCTCTTTTTATTAAAGAGAAGCTCTATATCG
GAGAAGCTTCTGTGGCCGTTATATTCGGCCTTATCGTGGGACCACATTGCCTGAATTGGTTTGCCCCGGAAGATTGGGGAAACTTGGATCT
GATTACCTTAGCTGCAGGTACCACTGAGCGTCAGACCCCGTAGAAAAGATCAAAGGATCTTCTTGAGATCCTTTTTTTCTGCGCGTAATCT
GCTGCTTGCAAACAAAAAAACCACCGCTACCAGCGGTGGTTTGTTTGTCGGATCAAGAGCTACCAACTCTTTTTCCGAAGGTAACTGGCTT
CAGCAGAGCGCAGATACCAAATACTGTTCTTCTAGTGTAGCCGTAGTTAGGCCACCACTTCAAGAACTCTGTAGCACCGCCTACATACCTC
GCTCTGCTAATCCTGTTACCAGTGGCTGCTGCCAGTGGCGATAAGTCGTGTCTTACCGGGTTGGACTCAAGACGATAGTTACCGGATAAGG
CGCAGCGGTCGGGCTGAACGGGGGGTTCGTGCACACAGCCCAGCTTGGAGCGAACGACCTACACCGAACTGAGATACCTACAGCGTGAGCT
ATGAGAAAGCGCCACGCTTCCCGAAGGGAGAAAGGCGGACAGGTATCCGGTAAGCGGCAGGGTCGGAACAGGAGAGCGCACGAGGGAGCTT
CCAGGGGGAAACGCCTGGTATCTTTATAGTCCTGTCGGGTTTCGCCACCTCTGACTTGAGCGTCGATTTTTGTGATGCTCGTCAGGGGGGC
GGAGCCTATGGAAAAACGCCAGCAACGCGGCCTTTTTACGGTTCCTGGCCTTTTGCTGGCCTTTTGCTCACATGTTCTTTCCTGCGGTACC
CAGATCCAATTCCCGCTTTGACTGCCTGAAATCTCCATCGCCTACAATGATGACATTTGGATTTGGTTGACTCATGTTGGTATTGTGAAAT
AGACGCAGATCGGGAACACTGAAAAATACACAGTTATTATTCATTTAAATTTTTTGTAGAAATGTCTTGGTGTCCTCGTCCAATCAGGTAG
CCATCTCTGAAATATCTGGCTCCGTTGCAACTCCGAACGACCTGCTGGCAACGTAAAATTCTCCGGGGTAAAACTTAAATGTGGAGTAATG
GAACCAGAAACGTCTCTTCCCTTCTCTCTCCTTCCACCGCCCGTTACCGTCCCTAGGAAATTTTACTCTGCTGGAGAGCTTCTTCTACGGC
CCCCTTGCAGCAATGCTCTTCCCAGCATTACGTTGCGGGTAAAACGGAGGTCGTGTACCCGACCTAGCAGCCCAGGGATGGAAAAGTCCCG
GCCGTCGCTGGCAATAATAGCGGGCGGACGCATGTCATGAGATTATTGGAAACCACCAGAATCGAATATAAAAGGCGAACACCTTTCCCAA
TTTTGGTTTCTCCTGACCCAAAGACTTTAAATTTAATTTATTTGTCCCTATTTCAATCAATTGAACAACTATCAAAACACAGAATTCAAAA
CGATGCGTTTCCCATCGATTTTCACAGCTGTTCTGTTTGCAGCTTCATCTGCTTTAGCTGCACCTGTTAACACAACTACAGAGGACGAAAC
GGCCCAGATCCCAGCTGAGGCAGTCATTGGTTATTCCGATTTGGAAGGTGATTTCGATGTCGCTGTGTTACCATTCAGTAATTCCACAAAT
AACGGTTTGCTGTTCATTAACACCACTATAGCAAGCATCGCTGCAAAAGAGGAAGGTGTTTCCCTAGAAAAGAGGGCCCAGTCCGTTTTGA
CTCAACCCCCTTCCGTATCCGCAGCTCCAGGCCAAAAAGTAACGATCTCTTGTTCAGGTTCCACTAGTAACATAGGTGACAATTATGTGTC
ATGGTACCAACAGTTGCCCGGAACTGCCCCTCAACTGCTGATCTACGACAATACCAAGAGGCCGTCAGGTATCCCAGACAGATTTTCCGGT
TCTAAGAGCGGCACATCGGCTACACTAGGTATCACGGGACTTCAAACCGGCGACGAGGCAGATTACTACTGCGCAACTTGGGATAATGATA
AGTGGGGAGTTGTTTTTGGAGGTGGTACTAAACTCGAAGTCTTGGGTGGTGGAGGAGGATCAGGAGGAGGAGGTTCTGGAGGAGGTGGTTC
ATCTGGCGGTGGATCTGAAGTGCAGCTTGTGGAGAGTGGTGGTGGTTTGGTTCAACCAGGAGGTAGCTTGAGACTGTCATGTGCCGCCAGC
GGTTTTACTTTCTCCTCCTATGCAATGTCTTGGGTCAGACAAGCACCTGGTAAGGGTTTGGAATGGGTATCAGCTATTTCGGGTAGTGGTG
GTTCGACATATTATGCTGACTCCGTTAAAGGTCGTTTTACTATTTCTAGAGACAATTCCAAAAATACCTTATATCTTCAAATGAACTCCCT
TAGAGCTGAGGATACTGCTGTTTACTACTGTGCTCGTGATGCTTGGTTGGATGTGTTGTCTGACGGCTTTGACTACTGGGGACAAGGTACT
TTGGTCACAGTGAGCAGCTGAGGGGCGGCCGCTCAAGAGGATGTCAGAATGCCATTTGCCTGAGAGATGCAGGCTTCATTTTTGATACTTT
TTTATTTGTAACCTATATAGTATAGGATTTTTTTTGTCATTTTGTTTCTTCTCGTACGAGCTTGCTCCTGATCAGCCTATCTCGCAGCAGA
TGAATATCTTGTGGTAGGGGTTTGGGAAAATCATTCGAGTTTGATGTTTTTCTTGGTATTTCCCACTCCTCTTCAGAGTACAGAAGATTAA
GTGAAACCTTCGTTTGTGCGGATCCTTCAGTAATGTCTTGTTTCTTTTGTTGCAGTGGTGAGCCATTTTGACTTCGTGAAAGTTTCTTTAG
AATAGTTGTTTCCAGAGGCCAAACATTCCACCCGTAGTAAAGTGCAAGCGTAGGAAGACCAAGACTGGCATAAATCAGGTATAAGTGTCGA
GCACTGGCAGGTGATCTTCTGAAAGTTTCTACTAGCAGATAAGATCCAGTAGTCATGCATATGGCAACAATGTACCGTGTGGATCTAAGAA
CGCGTCCTACTAACCTTCGCATTCGTTGGTCCAGTTTGTTGTTATCGATCAACGTGACAAGGTTGTCGATTCCGCGTAAGCATGCATACCC
AAGGACGCCTGTTGCAATTCCAAGTGAGCCAGTTCCAACAATCTTTGTAATATTAGAGCACTTCATTGTGTTGCGCTTGAAAGTAAAATGC
GAACAAATTAAGAGATAATCTCGAAACCGCGACTTCAAACGCCAATATGATGTGCGGCACACAATAAGCGTTCATATCCGCTGGGTGACTT
TCTCGCTTTAAAAAATTATCCGAAAAAATTTTCTAGAGTGTTGTTACTTTATACTTCCGGCTCGTATAATACGACAAGGTGTAAGGAGGAC
TAAACCATGGCTAAACTCACCTCTGCTGTTCCAGTCCTGACTGCTCGTGATGTTGCTGGTGCTGTTGAGTTCTGGACTGATAGACTCGGTT
TCTCCCGTGACTTCGTAGAGGACGACTTTGCCGGTGTTGTACGTGACGACGTTACCCTGTTCATCTCCGCAGTTCAGGACCAGGTTGTGCC
AGACAACACTCTGGCATGGGTATGGGTTCGTGGTCTGGACGAACTGTACGCTGAGTGGTCTGAGGTCGTGTCTACCAACTTCCGTGATGCA
TCTGGTCCAGCTATGACCGAGATCGGTGAACAGCCCTGGGGTCGTGAGTTTGCACTGCGTGATCCAGCTGGTAACTGCGTGCATTTCGTCG
CAGAAGAGCAGGACTAACAATTGACACCTTACGATTATTTAGAGAGTATTTATTAGTTTTATTGTATGTATACGGATGTTTTATTATCTAT
TTATGCCCTTATATTCTGTAACTATCCAAAAGTCCTATCTTATCAAGCCAGCAATCTATGTCCGCGAACGTCAACTAAAAATAAGCTTTTT
ATGCTCTTCTCTCTTTTTTTCCCTTCGGTATAATTATACCTTGCATCCACAGATTCTCCTGCCAAATTTTGCATAATCCTTTACAACATGG
CTATATGGGAGCACTTAGCGCCC
```

Fig. 12 A: Deep well plate expression of HSA fused to the LLP-signal sequence
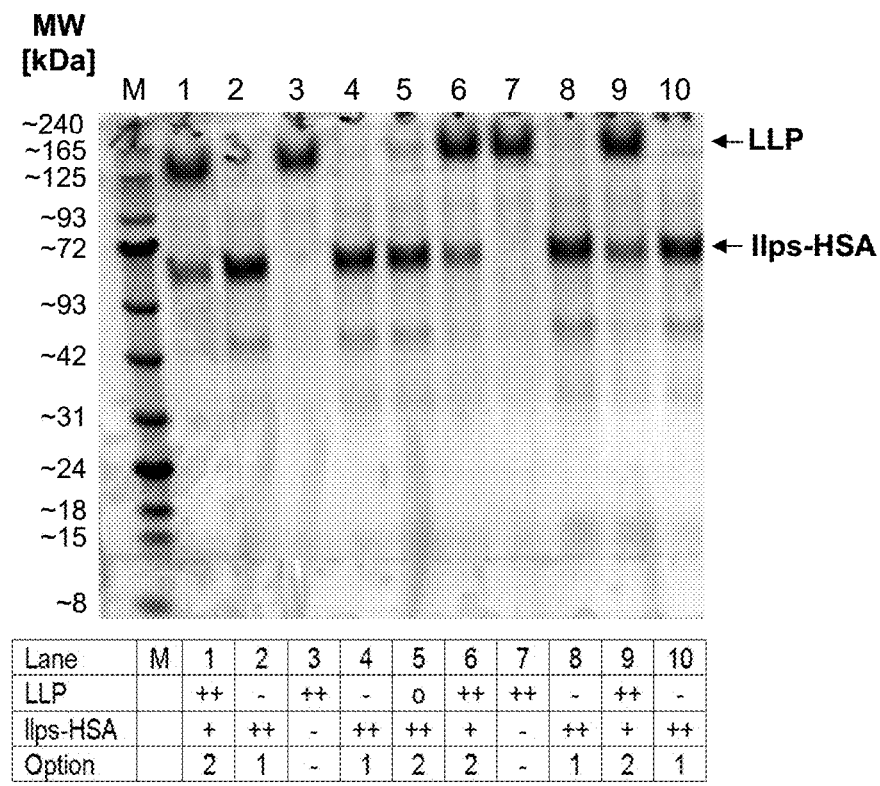
Fig. 12 B: Fermenter expression of HSA fused to the LLP-signal sequence
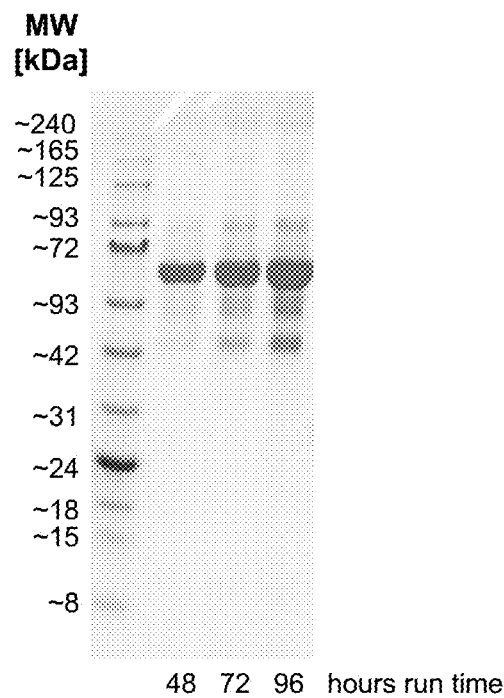

Fig. 13: Truncation-analysis of the LLP-promoter
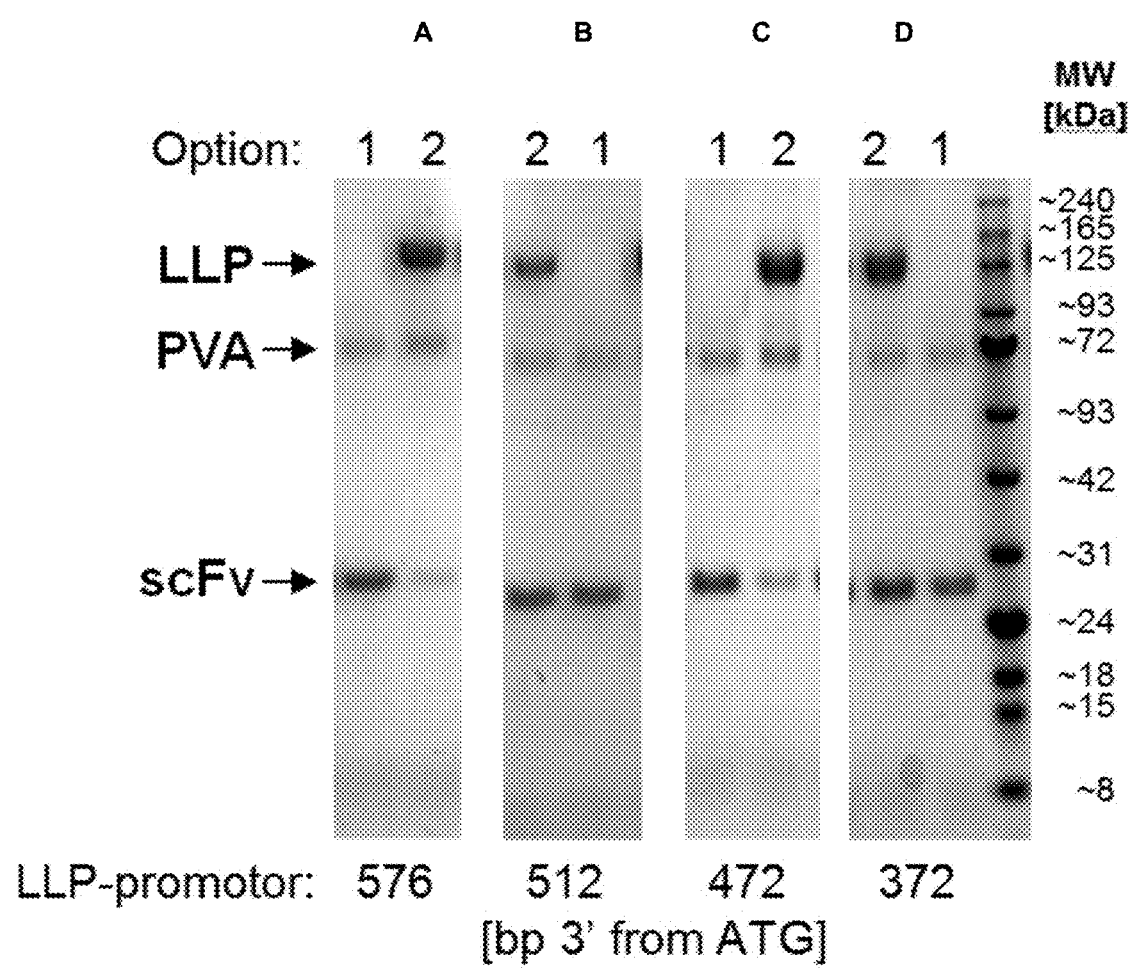

Fig. 14: Sequences S. cerevisae ssn6 and TUP1 (complete coding region)

A. Ssn6-nucleic acid (cyc8 = ssn6): SEQ ID NO: 135

>gi|398364854|ref|NM_001178460.3| Saccharomyces cerevisiae S288c
transcription regulator CYC8 (CYC8), partial mRNA

```
ATGAATCCGGGCGGTGAACAAACAATAATGGAACAACCCGCTCAACAGCAACAACAACAGCAACAACAACAGCAG
CAACAGCAACAGCAGGCAGCAGTTCCTCAGCAGCCACTCGACCCATTAACACAATCAACTGCGGAAACTTGGCTC
TCCATTGCTTCTTTGGCAGAAACCCTTGGTGATGGCGACAGGGCCGCAATGGCATATGACGCCACTTTACAGTTC
AATCCCTCATCTGCAAAGGCTTTAACATCTTTGGCTCACTTGTACCGTTCCAGAGACATGTTCCAAAGAGCTGCA
GAATTATATGAAAGAGCACTTTTGGTAAATCCCGAACTATCAGATGTGTGGGCTACTTTAGGTCATTGTTATCTG
ATGCTGGATGATCTGCAAAGAGCTTACAATGCCTATCAACAGGCTCTCTACCACCTCAGTAATCCCAACGTACCG
AAATTATGGCATGGAATCGGCATTCTTTATGACAGATATGGTTCGCTCGACTATGCCGAAGAAGCTTTTGCCAAA
GTTTTGGAATTGGACCCTCATTTTGAAAAGGCAAACGAAATTTACTTCAGACTAGGTATTATTTATAAACATCAG
GGTAAATGGTCTCAAGCTTTGGAATGCTTCAGATACATTCTCCCTCAACCTCCTGCTCCCTTGCAGGAGTGGGAC
ATATGGTTTCAGTTGGGTAGTGTTTTGGAGAGTATGGGAGAGTGGCAAGGTGCGAAGGAAGCCTACGAGCATGTC
TTGGCTCAAAATCAACATCATGCCAAAGTATTACAACAATTAGGTTGTCTTTACGGTATGAGTAACGTACAATTT
TATGACCCTCAAAAGGCATTGGATTATCTTCTAAAGTCGTTAGAAGCAGATCCCTCCGATGCCACTACATGGTAC
CATCTCGGTAGAGTGCATATGATTAGAACAGATTATACTGCCGCATATGATGCTTTCCAACAAGCTGTTAATAGA
GATTCAAGAAACCCTATCTTTTGGTGCTCAATCGGTGTTTTATATTACCAAATTTCTCAATACAGAGACGCCTTA
GACGCGTACACAAGAGCCATAAGATTAAATCCTTATATTAGTGAAGTTTGGTACGATCTAGGTACTCTTTACGAA
ACTTGTAACAACCAATTATCTGACGCCCTTGATGCGTATAAGCAAGCTGCAAGACTGGACGTAAATAATGTTCAC
ATAAGAGAAAGATTAGAAGCTTTAACAAAGCAGTTAGAAAACCCAGGCAATATAAACAAATCGAACGGTGCGCCA
ACGAATGCCTCTCCTGCCCCACCTCCTGTGATTTTACAACCTACCTTACAACCTAATGATCAAGGAAATCCTTTG
AACACTAGAATTTCAGCCCAATCTGCCAATGCTACTGCTTCAATGGTACAACAACAGCATCCTGCTCAACAAACG
CCTATTAACTCTTCTGCAACAATGTACAGTAATGGAGCTTCCCCTCAATTACAAGCTCAAGCTCAAGCTCAAGCT
CAAGCACAAGCTCAAGCACAAGCACAAGCTCAAGCACAAGCACAAGCACAAGCGCAAGCACAAGCACAAGCACAG
GCGCAAGCACAGGCACAAGCACAAGCACAAGCACATGCACAAGCGCAAGCACAAGCACAAGCACAGGCACAAGCA
CAAGCACAGGCGCAGGCACAACAACAACAACAACAACAGCAACAACAACAACAACAACAACAACAACAACAACAA
CAACAACAACAACAACAACAACAACAGCAGCAGCAATTACAGCCCCTACCAAGACAACAGCTGCAGCAAAAGGGA
GTTTCTGTGCAAATGTTAAATCCTCAACAAGGGCAACCATATATCACACAGCCAACAGTCATACAAGCTCACCAA
CTGCAACCATTTTCTACACAAGCTATGGAACATCCGCAAAGCTCTCAACTGCCACCTCAACAGCAACAACTACAA
TCTGTTCAACATCCACAACAACTTCAAGGCCAGCCTCAAGCCCAAGCTCCCCAACCTTTAATCCAGCATAACGTG
GAACAGAACGTTTTACCTCAAAAGAGATACATGGAAGGTGCAATCCACACTTTAGTAGATGCCGCCGTATCCAGT
AGCACCCACACAGAGAATAACACAAAGTCTCCTCGTCAACCAACCCATGCCATTCCAACGCAAGCTCCCGCAACA
GGAATAACGAACGCTGAACCACAGGTAAAGAAGCAAAAGTTGAACTCTCCAAATTCAAACATCAACAAATTAGTA
AATACTGCTACTTCCATTGAAGAAAATGCAAAATCTGAGGTGAGCAACCAATCGCCAGCAGTAGTGGAGTCTAAT
ACCAATAATACTTCACAAGAAGAAAAACCTGTAAAAGCAAACTCAATACCTTCAGTAATTGGCGCACAGGAACCT
CCACAGGAAGCTAGTCCTGCTGAAGAAGCTACCAAAGCAGCTTCTGTTTCTCCTTCTACAAAACCGCTTAATACG
GAACCAGAGTCATCTAGTGTCCAACCAACTGTATCATCAGAAAGTTCAACAACAAAAGCAAATGACCAAAGCACT
GCTGAGACCATAGAACTTTCTACTGCTACTGTTCCTGCAGAAGCAAGCCCTGTAGAAGACGAAGTAAGACAGCAT
TCTAAAGAGGAAAACGGCACAACTGAAGCATCTGCACCTTCTACTGAAGAGGCGGAGCCAGCAGCTTCCAGAGAT
GCTGAAAAACAACAAGATGAAACCGCTGCTACAACGATAACTGTAATCAAACCTACTTTGGAAACAATGGAAACA
GTGAAAGAGGAGGCCAAAATGCGTGAGGAAGAGCAAACATCTCAAGAAAATCCCCACAGGAGAACACACTTCCA
AGAGAAAATGTAGTAAGGCAAGTGGAAGAAGATGAAAACTACGACGACTAA
```

B. SSN6-Protein (SEQ ID NO: 137)
>NP_009670.3_SSN6_Saccharomyces cerevisiae

```
MNPGGEQTIMEQPAQQQQQQQQQQQQQQQAAVPQQPLDPLTQSTAETWLSIASLAETLGDGDRAAMAYDATLQF
NPSSAKALTSLAHLYRSRDMFQRAAELYERALLVNPELSDVWATLGHCYLMLDDLQRAYNAYQQALYHLSNPNVP
KLWHGIGILYDRYGSLDYAEEAFAKVLELDPHFEKANEIYFRLGIIYKHQGKWSQALECFRYILPQPPAPLQEWD
IWFQLGSVLESMGEWQGAKEAYEHVLAQNQHHAKVLQQLGCLYGMSNVQFYDPQKALDYLLKSLEADPSDATTWY
HLGRVHMIRTDYTAAYDAFQQAVNRDSRNPIFWCSIGVLYYQISQYRDALDAYTRAIRLNPYISEVWYDLGTLYE
TCNNQLSDALDAYKQAARLDVNNVHIRERLEALTKQLENPGNINKSNGAPTNASPAPPPVILQPTLQPNDQGNPL
NTRISAQSANATASMVQQQHPAQQTPINSSATMYSNGASPQLQAQAQAQAQAQAQAQAQAQAQAQAQAQAQAQAQ
AQAQAQAQAHAQAQAQAQAQAQAQAQQQQQQQQQQQQQQQQQQQQQQQQQLQPLPRQQLQQKG
VSVQMLNPQQGQPYITQPTVIQAHQLQPFSTQAMEHPQSSQLPPQQQQLQSVQHPQQLQGQPQAQAPQPLIQHNV
EQNVLPQKRYMEGAIHTLVDAAVSSSTHTENNTKSPRQPTHAIPTQAPATGITNAEPQVKKQKLNSPNSNINKLV
NTATSIEENAKSEVSNQSPAVVESNTNNTSQEEKPVKANSIPSVIGAQEPPQEASPAEEATKAASVSPSTKPLNT
```

Fig. 14 (continued)

EPESSSVQPTVSSESSTTKANDQSTAETIELSTATVPAEASPVEDEVRQHSKEENGTTEASAPSTEEAEPAASRD
AEKQQDETAATTITVIKPTLETMETVKEEAKMREEEQTSQEKSPQENTLPRENVVRQVEEDENYDD

C. Tup1-nucleic acid (SEQ ID NO: 136)

>gb|M35861.1|YSCAER2:247-2388 S.cerevisiae heme-regulated and catabolite
repressed genes repressor (TUP1) gene, complete cds ATGACTGCCAGCGTTTCGAATACGCAGAATAAGCTGAATGAGCTTCTCGATGCCATCAGACAGGAGTTTCTCCAA
GTCTCACAAGAGGCAAATACCTACCGTCTTCAAAACCAAAAGGATTACGATTTCAAAATGAACCAGCAGCTGGCT
GAGATGCAGCAGATAAGAAACACCGTCTACGAACTGGAACTAACTCACAGGAAAATGAAGGACGCGTACGAAGAA
GAGATCAAGCACTTGAAACTAGGGCTGGAGCAAAGAGACCATCAAATTGCATCTTTGACCGTCCAGCAACAGCGG
CAACAGCAACAGCAGCAACAGGTCCAGCAGCATTTACAACAGCAACAGCAGCAGCTAGCCGCTGCATCTGCATCT
GTTCCAGTTGCGCAACAACCACCGGCTACTACTTCGGCCACCGCCACTCCAGCAGCAAACACAACTACTGGTTCG
CCATCGGCCTTCCCAGTACAAGCTAGCCGTCCTAATCTGGTTGGCTCACAGTTGCCTACCACCACTTTGCCTGTG
GTGTCCTCAAACGCCCAACAACAACTACCACAACAGCAACTGCAACAGCAGCAACTTCAACAACAGCAACCACCT
CCCCAGGTTTCCGTGGCACCATTGAGTAACACAGCCATCAACGGATCTCCTACTTCTAAAGAGACCACTACTTTA
CCCTCTGTCAAGGCACCTGAATCTACGTTGAAAGAAACTGAACCGGAAAATAATAATACCTCGAAGATAAATGAC
ACCGGATCCGCCACCACGGCCACCACTACCACCGCAACTGAAACTGAAATCAAACCTAAGGAGGAAGACGCCACC
CCGGCTAGTTTGCACCAGGATCACTACTTAGTCCCTTATAATCAAAGAGCAAACCACTCTAAACCTATCCCACCT
TTCCTTTTGGATCTAGATTCCCAGTCTGTTCCCGATGCTCTGAAGAAGCAAACAAATGATTATTATATTTTATAC
AACCCGGCACTACCAAGAGAAATTGACGTTGAGTTACACAAATCTTTGGATCATACTTCAGTTGTTTGTTGCGTG
AAGTTCAGTAACGATGGTGAATACTTAGCCACAGGCTGCAACAAAACTACTCAAGTGTATCGCGTTTCAGATGGT
TCTCTGGTGGCCCGTCTATCTGACGATTCTGCTGCCAATAACCATCGAAATTCGATCACTGAAAATAACACCACC
ACGTCCACGGATAACAATACAATGACAACCACTACTACCACCACAATTACTACCACAGCGATGACTTCGGCAGCA
GAATTGGCAAAAGATGTGGAAAACCTGAACACTTCGTCTTCCCCATCATCCGACTTGTATATCCGTTCAGTGTGT
TTTTCTCCAGATGGGAAATTTTTGGCAACAGGTGCTGAAGACAGACTGATTAGAATTTGGGATATTGAAAATAGA
AAGATTGTTATGATTCTTCAAGGCCACGAACAAGATATTTATTCATTGGACTACTTTCCCTCAGGTGACAAATTA
GTCTCCGGTTCTGGTGACCGTACCGTTCGTATTTGGGACTTACGTACAGGCCAGTGTTCATTGACTTTATCCATT
GAAGATGGTGTTACCACCGTCGCTGTATCACCAGGTGATGGTAAATACATCGCTGCTGGTTCTCTAGATCGTGCT
GTGAGAGTTTGGGATTCCGAGACCGGATTCTTGGTGGAAAGACTAGATTCGGAAAACGAATCCGGTACAGGCCAC
AAGGACTCTGTTTATAGCGTTGTCTTCACTAGAGATGGACAAAGCGTTGTATCCGGCTCATTAGATAGATCTGTT
AAGCTCTGGAATTTGCAGAATGCAAACAACAAGAGCGATTCGAAAACTCCAAATTCCGGCACTTGTGAAGTTACG
TATATCGGGCATAAAGACTTTGTATTGTCCGTGGCCACCACACAAAATGATGAGTACATCTTGTCCGGTTCCAAA
GATCGTGGTGTCCTGTTTTGGGATAAGAAATCCGGCAATCCGTTATTGATGTTGCAAGGTCATAGGAATTCAGTT
ATATCTGTGGCTGTGGCAAACGGGTCTCCGCTGGGTCCAGAATATAACGTTTTTGCTACTGGTAGCGGTGATTGT
AAAGCAAGGATTTGGAAGTATAAAAAAATAGCGCCAAATTAA

D. Tup1-Protein (SEQ ID NO: 138)

MTASVSNTQNKLNELLDAIRQEFLQVSQEANTYRLQNQKDYDFKMNQQLAEMQQIRNTVYELELTHRKMKDAYEE
EIKHLKLGLEQRDHQIASLTVQQQRQQQQQQQVQQHLQQQQQQLAAASASVPVAQQPPATTSATATPAANTTTGS
PSAFPVQASRPNLVGSQLPTTTLPVVSSNAQQQLPQQQLQQQQLQQQQPPPQVSVAPLSNTAINGSPTSKETTTL
PSVKAPESTLKETEPENNNTSKINDTGSATTATTTTATETEIKPKEEDATPASLHQDHYLVPYNQRANHSKPIPP
FLLDLDSQSVPDALKKQTNDYYILYNPALPREIDVELHKSLDHTSVVCCVKFSNDGEYLATGCNKTTQVYRVSDG
SLVARLSDDSAANNHRNSITENNTTTSTDNNTMTTTTTTTITTTAMTSAAELAKDVENLNTSSSPSSDLYIRSVC
FSPDGKFLATGAEDRLIRIWDIENRKIVMILQGHEQDIYSLDYFPSGDKLVSGSGDRTVRIWDLRTGQCSLTLSI
EDGVTTVAVSPGDGKYIAAGSLDRAVRVWDSETGFLVERLDSENESGTGHKDSVYSVVFTRDGQSVVSGSLDRSV
KLWNLQNANNKSDSKTPNSGTCEVTYIGHKDFVLSVATTQNDEYILSGSKDRGVLFWDKKSGNPLLMLQGHRNSV
ISVAVANGSPLGPEYNVFATGSGDCKARIWKYKKIAPN

CONSTITUTIVE YEAST LLP PROMOTOR-BASED EXPRESSION SYSTEMS

This application is a Section 371 national phase entry of PCT application PCT/EP2016/054478, filed Mar. 2, 2016. This application also claims the benefit of the earlier filing date of European patent application 15157284.9, filed Mar. 3, 2015.

This application contains a Sequence Listing which has been submitted electronically in ASCII format and is herein incorporated by reference. The ASCII file, created on Aug. 17, 2017, is named 73091us-topto-20170830-SequenceListing.txt, and is 12,638,596 bytes in size.

FIELD OF THE INVENTION

The present invention belongs to the field of biotechnology, recombinant protein production, molecular biology, microbiology and microbial genetics. Specifically, the present invention relates to a modified eukaryotic cell, or expression system, respectively, comprising a modified gene, a polynucleotide sequence comprising said modified gene, an expression vector comprising said polynucleotiode sequence, a host cell comprising said expression vector, as well as to the use of said components.

Further, the present invention refers to methods using said components.

DESCRIPTION OF THE BACKGROUND ART

Expression systems for the expression of genes of interest (GOI) and also for the production of proteins of interest are widely known and of great importance in the field of molecular biology, microbiology and microbial genetics.

Until now, there are several expression systems known that allow the expression of certain desired genes and proteins, such as cell-based systems and cell-free systems. Cell-based systems comprise bacterial systems and eukaryotic systems, and cell-free systems are based for instance on the use of purified RNA polymerase, ribosomes, tRNA and ribonucleotides or are based on the use of systems containing cell-free protein synthesis systems such as for example rabbit reticulocyte lysates. The choice of the respectively used expression system depends on various factors such as the type of protein (eukaryotic or prokaryotic source of the protein) that is to be expressed, or whether post-translational modifications are necessary in order to ensure proper function and/or structure.

For instance, in general, if eukaryotic proteins are to be expressed, typically a eukaryotic expression system is selected. The reason therefore is that most eukaryotic proteins are modified for instance by phospohorylation, acylation, methylation, ubiquitylation or glycosylation. Bacteria are known to be no ideal host organisms for such modified proteins, as bacteria are prokaryotes which are not equipped with the full enzymatic machinery to accomplish the post-translational modifications or molecular folding that are required for many proteins to function properly. Thus, if eukaryotic proteins are to be expressed, typically expression systems using eukaryotic cells are used. Such expression systems are for instance based on yeast, fungi or insect cells. Expression systems in yeast use either inducible or non-inducible promoters for expression. Inducible promoters for methylotrophic yeast such as Pichia pastoris (P. Pastoris) often require the use of methanol as inducing substance.

Despite the known expression systems, there is still a need for an improved expression system, in particular for a eukaryotic expression system. Improvements are for instance desired with regard to the handling of the expression system, costs, safety aspects (e.g. avoiding the use of highly inflammable inducers such as methanol), complexity of the system, the time needed for expressing the proteins, or the yield of the expressed proteins.

SUMMARY OF THE INVENTION

The present invention provides the following aspects, subject-matters and preferred embodiments, which respectively taken alone or in combination, contribute to solving the object of the present invention:

(1) A modified eukaryotic cell, which is modified compared to its wildtype cell at least in that it comprises
- a modified ssn6-like gene or a modified ssn6-like related gene, and/or
- a modified expression level of SSN6-like protein or of SSN6-like related protein, or
- in that
- an ssn6-like gene or an ssn6-like related gene is deleted, respectively to the effect that
- the modified eukaryotic cell is not able to provide an SSN6-like protein or an SSN6-like related protein that exerts its wildtype function and/or wildtype activity,
- the amount of SSN6-like protein or of SSN6-like related protein being present in the modified eukaryotic cell differs from the amount of SSN6-like protein or of SSN6-like related protein being present in its wildtype form, and/or
- no SSN6-like protein or SSN6-like related protein is present in the modified cell, wherein said modified eukaryotic cell, compared to its wildtype cell, exhibits different SSN6-like protein or SSN6-like related -protein activity and/or function, preferably with respect to the proteins' ability in regulating gene expression.

In a preferred embodiment, said modified eukaryotic cell exhibits different SSN6-like protein or SSN6-like related protein activity and/or function with respect to the proteins' activity and/or function in regulating the expression of genes that are under control of the lectin-like protein (LLP) promoter.

(2) The modified eukaryotic cell according to item (1), wherein said modified eukaryotic cell exhibits reduced SSN6-like protein or SSN6-like related -protein activity and/or reduced function, or no SSN6-like protein or SSN6-like related -protein activity and/or function at all, preferably with regard to the proteins' activity and/or function in regulating gene expression, preferably in regulating the expression of genes that are under control of the LLP promoter.

(3) The modified eukaryotic cell according to item (1) or (2), wherein the ssn6-like gene and/or the ssn6-like related gene is/are modified in a regulatory sequence, such as promoter(s), enhancer(s), terminator(s), silencer(s), IRES-sequence(s), ribosome-binding site(s), and sequence(s) stabilizing or destabilizing the mRNA by secondary structure(s), and/or in a coding sequence.

(4) The modified eukryotic cell according to any of items (1) to (3), wherein the modified expression level of SSN6-like protein or of SSN6-like related protein is obtained by modifying the coding sequence of the ssn6-like gene and/or of the ssn6-like related gene.

(5) The modified eukaryotic cell according to any of items (1) to (4), wherein the total activity, function, preferably gene regulatory function, and/or amount of SSN6-like protein or SSN6-like related protein of the modified eukaryotic cell is at most 20%, preferably at most 15%, more preferably at most 10%, even more preferably at most 5% of the total activity, function and/or amount of SSN6-like protein or SSN6-like related protein of its wildtype form, and most preferably there is no activity and/or no function of the SSN6-like protein or SSN6-like related protein of the modified eukaryotic cell at all.

(6) The modified eukaryotic cell according to any of items (1) to (5), wherein the ssn6-like gene or the ssn6-like related gene and/or the expression level of the SSN6-like protein or of the SSN6-like related protein is modified by introduction of one or more point mutations, e.g. substitution, insertion or deletion of a single or more nucleotides in the polynucleotide sequence of the ssn6-like gene or of the ssn6-like related gene, partial or complete deletion of the polynucleotide sequence of the ssn6-like gene or of the ssn6-like related gene, and/or partial or complete replacement of the polynucleotide sequence of the ssn6-like gene or of the ssn6-like related gene by a different, e.g. heterologous, nucleotide sequence, wherein the polynucleotide sequence of the ssn6-like gene or of the ssn6-like related gene comprises coding and regulatory polynucleotide sequences, and wherein said regulatory polynucleotide sequences of the ssn6-like gene or of the ssn6-like related gene comprise promoters, enhancers, terminators, silencers, IRES-sequences, ribosome-binding sites, or sequences stabilizing or destabilizing the mRNA by secondary structures.

(7) The modified eukaryotic cell according to any of the preceding items, wherein said cell is a fungal cell, preferably a yeast cell, more preferably selected from the group consisting of *Saccharomyces* species (e.g., *Saccharomyces cerevisiae*), *Kluyveromyces* species (e.g., *Kluyveromyces lactis*), *Torulaspora* species, *Yarrowia* species (e.g., *Yarrowia lipolitica*), *Schizosaccharomyces* species (e.g., *Schizosaccharomyces pombe*), *Pichia* species (e.g., *Pichia pastoris* or *Pichia methanolica*), *Hansenula* species (e.g., *Hansenula polymorpha*), *Torulopsis* species, *Komagataella* species, *Candida* species (e.g., *Candida boidinii*), and *Karwinskia* species, even more preferably the eukaryotic cell is a *Pichia* cell, most preferably a *Pichia pastoris* cell according to current classification.

(8) The modified eukaryotic cell according to item (7), wherein the cell can be any *Pichia pastoris* cell, preferably a cell of a strain selected from the group consisting of NRRL Y-11430, CBS704, GS115, and KM71.

(9) The modified eukaryotic cell according to any of the preceding items, wherein said modified eukaryotic cell comprises a polynucleotide sequence which represents a modification of SEQ ID NO: 1, preferably the modified eukaryotic cell comprises SEQ ID NO: 7.

SEQ ID NO: 1 represents the coding region of the ssn6-like gene.

SEQ ID NO: 7 represents modified ssn6-like nucleotide sequence.

(10) The modified eukaryotic cell according to any of the proceding items, wherein said wildtype cell contains a SSN6-like or SSN6-like related protein, which protein comprises one or both of the consensus amino acid sequences depicted in SEQ ID NO: 63 and 64.

In other words, the eukaryotic cell, prior to its modification resulting in said modified eukaryotic cell, contained an SSN6-like or SSN6-like related protein, which protein comprised one or both of the amino acid sequences depicted in SEQ ID NO: 63 and 64.

(11) A polynucleotide sequence comprising, preferably consisting of, a modified ssn6-like gene or nucleotide sequence, e.g. as depicted in SEQ ID NO: 7, or a modified ssn6-like related gene, wherein, if said polynucleotide sequence (a) is introduced into a suitable expression system, and tried to be expressed, essentially no SSN6-like protein or SSN6-like related protein is expressed, or (b) is expressed in a suitable expression system, SSN6-like protein or SSN6-like related protein is expressed that does not exert its wildtype function and/or wildtype activity, preferably with respect to its activity and/or function in regulating gene expression, more preferably in regulating the expression of genes that are under control of the LLP promoter, and/or (c) is expressed in a suitable expression system, an amount of SSN6-like protein or SSN6-like related protein is expressed that differs from the amount of wildtype SSN6-like protein or of SSN6-like related protein.

In order to assess any of (a) to (c), the corresponding wildtype polynucleotide sequence is tried to be expressed under comparable or the same conditions, under which the modified ssn6-like gene or modified ssn6-like related gene is tried to be expressed.

(12) The polynucleotide sequence according to item (11), wherein, if said polynucleotide sequence is introduced into a suitable expression system, and tried to be expressed, or is expressed in a suitable expression system, the amount of SSN6-like protein or SSN6-like related protein is reduced, or there is essentially no, preferably no, SSN6-like protein or SSN6-like related protein at all present, compared to the amount of SSN6-like protein or SSN6-like related protein that is expressed when the corresponding wildtype polynucleotide sequence is expressed under comparable or the same conditions.

(13) The polynucleotide sequence according to item (11) or (12), wherein a regulatory sequence of the ssn6-like gene or of the ssn6-like related gene is selected from the group comprising promoters, enhancers, terminators, silencers, IRES-sequences, ribosome-binding sites, and sequences stabilizing or destabilizing the mRNA by secondary structures, preferably said regulatory sequence is selected from the group consisting of promoters, enhancers, and terminators.

(14) The polynucleotide sequence according to any of items (11) to (13), wherein the ssn6-like gene or the ssn6-like related gene has been modified as defined in item (6).

(15) The polynucleotide sequence according to any of items (11) to (14), wherein the polynucleotide sequence comprises, preferably consists of, modifications of SEQ ID NO: 1, preferably the polynucleotide sequence comprises, more preferably consists of, SEQ ID NO: 7.

(16) A nucleic acid sequence comprising the polynucleotide sequence according to any of items (11) to (15).

(17) A vector comprising the polynucleotide sequence/nucleic acid sequence according to any of items (11) to (16).

(18) A host cell comprising the vector according to item (17), or a polynucleotide according to any of items (11) to (13).

(19) The host cell according to item (18), wherein said host cell is a bacterium, preferably *Escherichia coli*.

(20) A polypeptide encoded by the polynucleotide sequence according to any of items (11) to (15).

(21) An expression vector comprising a promoter, wherein said promoter is characterized in that it is repressed in the presence of SSN6-like related protein or SSN6-like protein if said expression vector is introduced into a suitable expression system, e.g. into a eukaryotic cell as defined in item (7) or (8).

(22) The expression vector according to item (21), which further comprises one or more gene(s) of interest.

(23) The expression vector according to item (22), wherein the gene(s) of interest is/are under control of the promoter defined in item (21).

(24) The expression vector according to any of items (21) to (23), wherein said promoter is an LLP promoter, preferably an LLP promoter comprising, preferably consisting of, SEQ ID NO: 2 or 12, or consisting of a sequence having a length of 1000, 775, 675, 605, 576, 512, 472, 415, 404, 372, 305, 285, 235, 165, or 100 nucleotides counted in each case from the 3'-end of SEQ ID NO: 12, or modified versions thereof, said modified versions being characterized in that they still exhibit the promoter function.

(25) The expression vector according to any of items (21) to (24), wherein, if the promoter is an LLP promoter as defined in item (24), LLP protein is not encoded by the polynucleotide sequence of this expression vector, and preferably the gene of interest is selected from the group consisting of genes encoding enzymes, antibodies or fragments thereof, hormones, structural proteins (such as albumin), and protein-antigens being suitable for vaccines.

(26) The expression vector according to any of items (21) to (24), wherein, if the promoter is an LLP promoter as defined in item (24), LLP protein is encoded by the polynucleotide sequence of this expression vector, and preferably the gene of interest is selected from the group consisting of genes encoding enzymes, antibodies or fragments thereof, hormones, structural proteins (such as albumin), and protein-antigens being suitable for vaccines.

(27) The expression vector according to any of items (21) to (26), wherein said expression vector further comprises features selected from any one of the following: a selection marker;
(ii) a purification marker;
(iii) a signal sequence, preferably an alpha-factor secreting signal sequence, more preferably the MFalpha pre-pro signal sequence, even more preferably a signal sequence comprising or consisting of, preferably consisting of, SEQ ID NO: 14 or SEQ ID NO: 21;
(iv) an origin of replication; and/or
(v) a nucleotide sequence for targeted and/or random integration into the genome of a host cell.

In a preferred embodiment, the signal sequence (iii) of the expression vector according to item (27) comprises or consists, preferably consists of, SEQ ID NO: 14.

(28) The expression vector according to any of items (21) to (27), wherein said vector contains more than one promoter as defined in item (21), and/or wherein said vector contains more than one LLP promotor according to item (24), preferably 2, 3, 4, 5, or 6 LLP promoters according to item (24) and preferably different LLP promoters, e.g. different length LLP-promoters, according to item (24) which result in different expression rates of the genes of interest under control of said LLP promoter.

(29) The expression vector according to any of items (21) to (27), wherein said vector contains, besides one or more LLP promoters, in addition one or more other promoters different from a LLP promoter, which other promoters result in expression rates different to the expression rates of the LLP promoters.

(30) Use of an expression vector according to item (28) or (29) for the expression of a multimeric protein, said multimeric protein consisting of two or more individual protein chains, which individual protein chains are connected to each other by one or more disulfide bridges and/or which individual protein chains form a multimeric protein by other forms of protein chain-protein chain interactions.

(31) Use according to item (30) wherein said multimeric protein is expressed by transforming a cell with two or more individual vectors, wherein each vector is containing one or more promoter(s) as defined in item (21) and/or in item (24), or wherein at least one vector contains a LLP promoter and at least one vector contains other promoter different from a LLP promoter.

(32) A host cell, comprising the vector according to item (17) or any of items (21) to (29).

(33) The host cell according to item (32), wherein said host cell is a bacterium, preferably *Escherichia coli,* or the modified eukaryotic cell according to any of items (1) to (9).

(34) The modified eukaryotic cell according to any of items (1) to (10), comprising the expression vector according to any of items (21) to (29).

(35) An expression system, comprising
a) the modified eukaryotic cell as defined in any of items (1) to (10);
b) the expression vector as defined in any of items (21) to (29), wherein said expression vector can also be present in linearized form and/or at least parts of the vector being integrated into the genome of the modified eukaryotic cell.

(36) The modified eukaryotic cell according to any of items (1) to (10), further comprising a promoter as defined in item (21) or (24).

(37) The modified eukaryotic cell according to item (36), further comprising (a) gene(s) of interest being under control of the promoter as defined in item (21) or (24).

(38) The modified eukaryotic cell according to item (37), wherein the gene(s) of interest is (are) as defined in item (25).

(39) The modified eukaryotic cell according to item (37) or (38), wherein the LLP gene is not expressed in addition to the gene(s) of interest, or wherein the LLP gene is expressed in addition to the gene(s) of interest.

(40) The modified eukaryotic cell according to item (39),
wherein the LLP promoter or the LLP-like promoter controls (a) gene(s) of interest which is (are) different from LLP, and in addition another copy of said promoter controls the LLP-gene (e.g. Option 2 in FIG. 3D); or
wherein the LLP promoter or the LLP-like promoter only controls (a) gene(s) of interest which is (are) different from LLP and no LLP-gene is present (e.g. Option 1 in FIG. 3C).

(41) Use of
(A) the modified eukaryotic cell,
(B) the polynucleotide sequence,
(C) the expression vector,
(D) the host cell, or
(E) an expression system
according to any of items (1) to (40)
in a method of expressing, preferably overexpressing, gene(s) of interest.

(42) Method for determining the purity of a composition comprising the expression product of a gene of interest, comprising the following steps:

(a) expressing gene(s) of interest by using a modified eukaryotic cell according to any of items (1) to (10) and by using an expression vector according to item (25), wherein
  (a1) the modified eukaryotic cell comprises a gene encoding LLP protein under control of an LLP promoter or an LLP-like promoter, and wherein
  (a2) the expression vector comprises one or more gene(s) of interest under control of an LLP promoter or an LLP-like promoter, wherein said gene(s) of interest does (do) not encode LLP,
thereby obtaining a composition comprising the expression product of the gene(s) of interest, i.e. the protein(s) of interest, and the LLP protein;
(b) determining the amount of the expression product of the gene(s) of interest, i.e. the amount of the protein(s) of interest, and the amount of LLP protein being present in the composition obtained in step (a), wherein the amount of LLP protein compared to the amount of expression product of the gene(s) of interest, i.e. of the protein(s) of interst, is indicative for the purity of the composition obtained in step (a); and, optionally,
(c) subjecting the composition of step (a) to one or more downstream purification step(s), followed by step (b) for determining the amount of the the protein(s) of interest, and the amount of LLP protein being present in the composition obtained after having carried out said downstream purification step, i.e. monitoring host-cell-protein depletion (purity of gene of interest protein in the course of its purification).

(43) A method of expressing one or more gene(s) of interest in a eukaryotic cell comprising an ssn6-like gene or an ssn6-like related gene, wherein the translation of the mRNA transcript of the ssn6-like gene or the ssn6-like related gene is prevented by hybridizing a complementary sequence or a partial sequence thereof to the mRNA transcript.

(44) The method of item (43), wherein the partial sequence of the complementary sequence is a siRNA, antisense RNA, a ribozyme, or triplex RNA or DNA.

(45) A method of expressing one or more gene(s) of interest in a eukaryotic cell comprising an SSN6-like related expression cassette or SSN6-like expression cassette, wherein the SSN6-like related protein or the SSN6-like protein in said eukaryotic cell is modified or inhibited in its function and/or activity.

(46) The method according to item (45), wherein the SSN6-like related protein or SSN6-like protein of said eukaryotic cell is modified or inhibited in its function and/or activity in regulating the LLP promoter, preferably the SSN6-like related protein or SSN6-like protein exhibits reduced SSN6-like protein or SSN6-like related -protein activity and/or function, or no SSN6-like protein or SSN6-like related -protein activity and/or function at all.

(47) A eukaryotic cell comprising
a modified ssn6-like gene or a modified ssn6-like related gene, wherein said gene has inserted a foreign nucleotide sequence, to the effect that
  (i) the eukaryotic cell is not able to provide an SSN6-like protein or an SSN6-like related protein that exerts its wildtype function and/or wildtype activity, preferably with respect to its activity and/or function in regulating the LLP promoter or LLP-like promoter,
  (ii) the amount of SSN6-like protein or of SSN6-like related protein being present in the eukaryotic cell differs from the amount of SSN6-like protein or of SSN6-like related protein being present in its wildtype form, preferably the amount of the SSN6-like protein or of the SSN6-like related protein is reduced, and/or
  (iii) no SSN6-like protein or SSN6-like related protein is present in the eukaryotic cell,
and
a gene of interest that replaces a part or all of the coding region of the gene encoding the LLP protein, and that is under control of the LLP promoter, to the effect that essentially no LLP protein is present in the eukaryotic cell,
preferably wherein said eukaryotic cell exhibits reduced SSN6-like protein or SSN6-like related -protein activity and/or function, or no SSN6-like protein or SSN6-like related -protein activity and/or function at all.

(48) A eukaryotic cell comprising
a modified ssn6-like gene or a modified ssn6-like related gene, wherein said gene has inserted a foreign nucleotide sequence, to the effect that
  (i) the eukaryotic cell is not able to provide an SSN6-like protein or an SSN6-like related protein that exerts its wildtype function and/or wildtype activity, preferably with respect to its activity and/or function in regulating the LLP promoter,
  (ii) the amount of SSN6-like protein or of SSN6-like related protein being present in the eukaryotic cell differs from the amount of SSN6-like protein or of SSN6-like related protein being present in its wildtype form, preferably the amount of the SSN6-like protein or of the SSN6-like related protein is reduced, and/or
  (iii) no SSN6-like protein or SSN6-like related protein is present in the eukaryotic cell,
a gene of interest under control of the LLP promoter, and
an llp gene,
preferably wherein said eukaryotic cell exhibits reduced SSN6-like protein or SSN6-like related -protein activity and/or function, or no SSN6-like protein or SSN6-like related -protein activity and/or function at all.

(49) Nucleotide sequence comprising at it's 5'-end a nucleotide sequence which codes for the peptide sequence of the LLP-signalsequence and which is depicted in SEQ ID NO: 3, and further comprising a nucleotide sequence which is coding for a protein different to the native LLP-protein sequence.

(50) Use of a nucleotide sequence according to item (45) for the manufacture of a non-LLP-protein in a yeast cell, which yeast cell secreates said non-LLP-protein into the cell culture medium, due to the secretion-promoting activity of said peptide sequence of the LLP-signalsequence which is depicted in SEQ ID NO: 3.

(51) Use of a promotor comprising the LLP-promoter sequence according to SEQ ID NO: 12 (1000 bp of LLP-promoter), or according to SEQ ID NO: 2 (605 bp of LLP-promoter), or according to SEQ ID NO: 129 (576 bp of LLP-promoter), or according to SEQ ID NO: 130 (512 bp of LLP-promoter), or according to SEQ ID NO: 131 (472 bp of LLP-promoter), or according to SEQ ID NO: 132 (404 bp of LLP-promoter), or according to SEQ ID NO: 133 (372 bp of LLP-promoter), or according to SEQ ID NO: 134 (305 bp of LLP-promoter), in a vector for expression of a gene of interest, wherein said LLP-promoter sequence has at least 30%, preferably 40%, preferably 50%, preferably 60%, preferably 70%, preferably, preferably 80%, preferably 90%, preferably 95%, preferably 97%, preferably 99%, preferably 100% sequence identity with SEQ ID NO: 12.

(52) Vector comprising the LLP-promoter sequence as defined in item (51).

(53) Host cell comprising a vector according to item (52) or comprising one or more of the LLP-promoter sequences according to item (51).

(54) Nucleic acid comprising one or more of the LLP-promoter sequences according to item (51). In a preferred embodiment, the nucleic acid according to item (54) is used as a promoter, Definitions of Terms as Used Within the Meaning of the Present Invention Within the meaning of the present invention, the SSN6-like protein is a protein that comprises, preferably consists of, the amino acid sequence as depicted in SEQ ID NO: 8.

The term "ssn6-like gene" denotes a gene encoding the SSN6-like protein.

The coding region of the ssn6-like gene of *P. pastoris* is depicted in SEQ ID NO: 1.

Genes or proteins that resemble the ssn6-like gene or SSN6-like protein in respect of function, activity and sequence, or only in respect of function and activity, are denoted herein as "ssn6-like related genes" or "ssn6-like related proteins".

Within the meaning of the present invention, the term "gene" denotes a certain nucleic acid sequence that encodes a polypeptide or an RNA chain that has a function in the organism. The nucleic acid sequence comprises regulatory regions (herein also denoted as regulatory polynucleotide sequences or regulatory sequences), transcribed regions (such as regions that code for proteins, but also regions that are transcribed but do not code for proteins, such as introns) and/or other functional sequence regions.

In general, regulatory regions are primarily regions flanking the 3'- and 5'-region of the coding region of the gene, but certain regulatory regions such as Trans-regulatory elements, might be located quite distant within the same chromosome or might even be located on a different chromosome. In particular, within the meaning of the present invention, the regulatory regions of the ssn6-like (or ssn6-like related) gene comprise the flanking region being located up to 200 nucleotides up- and downstream of the 3'- and 5'-end of the ssn6-like coding region.

Examples of regulatory polynucleotide sequences are promoters, enhancers, terminators, silencers, IRES-sequences, ribosome-binding sites, and sequences stabilizing or destabilizing the mRNA by secondary structures. Within the meaning of the present invention, the term "regulatory polynucleotide sequence" denotes polynucleotide sequences that modify the expression of genes, for example the ssn6-like gene and/or of the ssn6 gene, and/or a gene of interest and/or the Llp gene.

"Protein-antigens that are suitbale for vaccines" are antigens that are able to elicit a proper, desired immune response upon vaccination. For instance, such antigens are neuraminidase (NA) or haemagglutinin (HA) of influenza virus. Further antigens that are suitbale for vaccination purpose are known to a person skilled in the art. Methods for testing the suitability of proteins for eliciting a proper immune response are known to a skilled person.

A "polynucleotide" or "nucleic acid" sequence includes DNA (desoxyribonucleic acid) or RNA (ribonucleic acid), in single stranded or double stranded form or otherwise.

In general, the term "ssn6-like gene" denotes a gene encoding the SSN6-like protein. The ssn6-like gene belongs to an evolutionary conserved family of proteins (see FIG. 9A), and it is known that certain yeasts, flies, worms and mammals contain proteins that resemble SSN6-like proteins in sequence and function/activity. These proteins are denoted herein as "SSN6-like related proteins", and the genes that encode these proteins are denoted herein as "ssn6-like related genes". Examples of yeasts that contain proteins that belong to the SSN6-like related protein family are *Pichia pastoris* (*P. Pastoris*), *Saccharomyces cerevisiae* (*S. cerevisiae*) and *Candida albicans* (*C. albicans*).

Within the meaning of the present invention, the term "ssn6-like-related protein" for example denotes the respective proteins whose NCBI (National Center for Biotechnology Information, USA) GenBank accession numbers are noted on the left hand site of FIG. 9A. FIG. 9A only shows an internal part of these sequences aligned to the corresponding sequence part of the *P. Pastoris* ssn6-like sequence (NCBI GenBank accession number CCA36593.1). In detail these proteins include XP_004181958.1 (SEQ ID NO: 24), KDQ17717.1 (SEQ ID NO: 25), CCK71477.1 (SEQ ID NO: 26), EDK38165.2 (SEQ ID NO: 27), XP_003688172.1 (SEQ ID NO: 28), XP_003667908.1 (SEQ ID NO: 29), EGA59684.1 (SEQ ID NO: 30), EDN64727.1 (SEQ ID NO: 31), AAA34545.1 (SEQ ID NO: 32), NP_009670.3 (SEQ ID NO: 33), XP_001731010.1 (SEQ ID NO: 34), CCU98386.1 (SEQ ID NO: 35), XP_646078.1 (SEQ ID NO: 36), XP_003288629.1 (SEQ ID NO: 37), CCF50299.1 (SEQ ID NO: 38), XP_761648.1 (SEQ ID NO: 39), XP_007880878.1 (SEQ ID NO: 40), EPB82504.1 (SEQ ID NO: 41), CDK26448.1 (SEQ ID NO: 42), ESW97404.1 (SEQ ID NO: 43), CCH42354.1 (SEQ ID NO: 44), CDR41214.1 (SEQ ID NO: 45), XP_002489776.1 (SEQ ID NO: 46), XP_002770760.1 (SEQ ID NO: 47), EDK37317.2 (SEQ ID NO: 48), XP_001485744.1 (SEQ ID NO: 49), XP_002619527.1 (SEQ ID NO: 50), XP_004200097.1 (SEQ ID NO: 51), XP_004199242.1 (SEQ ID NO: 52), XP_002419644.1 (SEQ ID NO: 53), BAF31137.1 (SEQ ID NO: 54), XP_719833.1 (SEQ ID NO: 55), EMG49052.1 (SEQ ID NO: 56), XP_002551300.1 (SEQ ID NO: 57), XP_001526425.1 (SEQ ID NO: 58), CCE42279.1 (SEQ ID NO: 59), XP_003868368.1 (SEQ ID NO: 60), XP_001387682.2 (SEQ ID NO: 61), XP_007376632.1 (SEQ ID NO: 62) as found in the NCBI data base.

Within the meaning of the present invention, the term "SSN6-like protein" denotes the protein comprising (preferably consisting of) the amino acid sequence as depicted in the sequence depicted in FIG. 2A (SEQ ID NO: 8).

Furthermore within the meaning of the present invention, the term "SSN6-like protein" denotes a protein comprising consensus amino acid sequences depicted in FIG. 9B or 9C, namely:

```
FIG. 9 B: Consensus sequence 1
                                      (SEQ ID NO: 63)
W(CGL)(SLTA)(IMV)G(VINSTK)LY(YFLA)(QNSRKE)(INLM)

(GNSKR)Q(NFYL)(HRETPAK)D(AST)(LI)(DGTNASE)(AV)(YF)
and/or

FIG. 9 C: Consensus sequence 2
                                      (SEQ ID NO: 64)
W(YFLED)(NDG)L(GLAS)(TSIQC)(LIV)YE(TSARKQ)(CS)

(NHSDEH)(DNK-RGF)(Q-H)(ILTHVAS)(TSNQERIAMG)D(ASV)

(LIASC)(DHNE)(SA)(YC)(EAKRQMTLNDS)(RQK)
```

The both consensus sequences are written in single letter code and groups of amino acids in brackets. Groups of amino acids in brackets means that either amino acid in the brackets can be present at that position within the consensus sequence. For example the consensus sequence in FIG. 9B starts with W at position 1, and at position 2 there can be present either C or G or L, at position 3 there can be present either S or L or T or A, etc.

The corresponding amino acid position within the context of the *P. pastoris* SSN6-like protein is given below the consensus sequences of FIGS. 9B and 9C, e.g. the Tryptophane residue (W) in position 1 of the consensus sequence in FIG. 9B corresponds to the amino acid position 352 of the *P. pastoris* SSN6-like protein sequence.

In case there is written a "-" (dash), for example at position 407 of consensus sequence in FIG. 9C, (Q-H), this means that on this position there can be either a Q, no amino acid, or a H.

Further within the meaning of the present invention, the term "ssn6-like related gene" or "SSN6-like related protein" denotes a gene or protein that resembles the ssn6-like gene or SSN6-like protein in respect of function, activity and sequence, or only in respect of function and activity.

The coding region of the ssn6-like gene of *P. Pastoris* is depicted in FIG. 1A (SEQ ID NO: 1). The amino acid sequence of the SSN6-like protein of *P. Pastoris* is depicted in FIG. 1J (SEQ ID NO: 13).

The term "llp gene" denotes a gene encoding LLP protein. SEQ ID NO: 16 depicts the nucleotide sequence of the coding region of the llp gene from *P. Pastoris,* including the signal sequence.

"Resembling with respect to function" or "resembling with respect to activity" defines that the ssn6-like related gene product, i.e. the SSN6-like related protein that is encoded by the "ssn6-like related gene", exhibits essentially the same function and activity as the SSN6-like protein of *P. Pastoris* (depicted in SEQ ID NO: 13) with regard to the LLP-promoter ("Lectin-like protein with similarity to Flo1p"), when said function and activity is compared in a suitable system when applying comparable, preferably corresponding, conditions. The function and activity that is of interest in the present invention, and thus has to be compared or assessed, respectively, is the ability of the SSN6-like protein and SSN6-like related protein, respectively, to regulate, preferably repress (reduce), and even more preferably prevent, the expression of genes that are under control of the LLP-promoter. For instance, in a wildtype situation, typically the gene that is under control of the LLP promter is a gene encoding LLP protein. In this case, in order to determine whether the SSN6-like related protein exhibits essentially the same function and/or activity as the SSN6-like protein, for instance the amount of LLP protein being present is compared, i.e. the amount of LLP protein in an expression system wherein an ssn6-like related gene (and, thus, an SSN6-like related protein) is present, compared to an expression system wherein an SSN6-like gene (and, thus, an SSN6-like protein) is present. If it is shown that the candidate ssn6-like related gene and the ssn6-like gene (and its gene products, (candidate) SSN6-like related protein and SSN6-like protein, respectively (also referred to herein as "SSN6-like/SSN6-like related protein" or "SSN6-like related/SSN6-like protein") exhibit essentially the same function/activity with regard to the LLP-promoter (and with regard to the gene that is under control of said promoter, such as the llp gene), e.g. with regard to the determined amount of LLP protein, then the candidate ssn6-like related gene is a ssn6-like related gene within the meaning of the present invention.

A promoter is defined as a DNA regulatory region capable of binding an RNA polymerase in a cell and that initiates transcription of a particular gene to which it operably links. Typically, promoters are located near the transcription start sites of the respective gene(s) that is under control of said promoter, on the same strand. FIG. 1B (SEQ ID NO: 2) and FIG. 1I (SEQ ID NO: 12) show nucleotide sequences of the LLP promoter of *P. Pastoris* (FIG. 1B=first 605 nucleotides 5' from ATG start codon, FIG. 1I=fist 1000 nucleotides 5' from ATG start codon).

Whenever reference is made herein to an LLP promoter, an "LLP-like promoter" is also comprised by this expression. Within the meaning of the present invention, an LLP-like promoter is a promoter that exhibits essentially the same function/activity as the LLP promoter, i.e. is still able to essentially exert the LLP promoter's wildtype function/activity.

In order to determine whether a candidate ssn6-like-related gene and SSN6-like-related protein, respectively, exhibits essentially the same function and activity as the ssn6-like-gene and SSN6-like protein, respectively, with respect to the LLP-promoter, any suitable method that is known to a person skilled in the art can be used. Examples of such methods are measuring the amount of LLP protein in the supernatant of a cell culture for example by Enzyme Linked Inmmunosorbent Assay (ELISA), or by western blotting, or measuring the level of LLP mRNA by northern blotting or by quantitative Polymerase Chain Reaction (qPCR) or reverse transcriptase qPCR, or measuring the activity of the LLP-promoter or LLP-like promoter ("LLP/LLP-like promoter") for example by using luciferase reporter gene assays or by using LLP-promoter-green fluorescent protein (GFP) constructs, etc. All these methods are well known to a person skilled in the art and represent routine work. A textbook comprising protocols for routine methods is for instance Sambrook et al., "Molecular Cloning: A Laboratory Manual", 4$^{th}$ Edition, Cold Spring Harbor Laboratory Press, (2012), referred to herein as Sambrook et al. Within the meaning of the present invention, a candidate ssn6-like-related gene is considered as exhibiting essentially the same function/activity as the ssn6-like-gene, if its effect (and the effect of its gene product, respectively) on the LLP protein expression is essentially the same.

Within the meaning of the present invention, the expression "essentially the same" defines a deviation of up to 20%, preferably of up to 10%, more preferably of up to 7% and even more preferably of up to 3% of a given value.

Accordingly, the expression "essentially no" defines that there is an amount/activity of the respective matter (such as protein) present (or left) that corresponds to at most 20%, preferably at most 10%, more preferably at most 7%, and even more preferably at most 3% of the respective wildtype amount/activity. "Essentially no" also includes the absence of the respective matter/amount/activity, preferably meaning below the detection limit of the methods described in this application for that matter/amount/activity.

Within the meaning of the present invention the term "reduced", e.g. "reduced" activity, "reduced" function, or "reduced" amount denotes that the total activity, function, preferably gene regulatory function, or amount of a matter (e.g. SSN6-like protein or SSN6-like related protein of the modified eukaryotic cell; or LLP promoter) is at most 20%, preferably at most 15%, more preferably at most 10%, even more preferably at most 5% of the total activity, function and/or amount of the wildtype form of this matter (e.g. SSN6-like protein or SSN6-like related protein; or LLP promoter).

It is possible that nucleotide sequences and the proteins they encode, respectively, which exhibit essentially the same function and activity as ssn6-like gene and SSN6-like protein, respectively, exhibit a comparably low degree of sequence identity such as 50%, 40% or 30% or even lower, such as 25%, 20%, 19%, 18%, 17%, 16%, 15%, 12%, 10%, or 5%. Thus, ssn6-like-related genes/SSN6-like-related proteins within the meaning of the present invention are genes/proteins that—first of all—exhibit essentially the same function/activity as the ssn6-like gene/SSN6-like protein with regard to the LLP protein (in wild type situation). Hence, in a preferred embodiment of the present invention, the term "ssn6-like-related gene" denotes genes that resemble the ssn6-like gene as defined herein in respect of function/activity, i.e. the ability of the SSN6-like-related protein being encoded by the ssn6-like-related gene to regulate the expression of genes that are under control of the LLP-promoter, and LLP-promoter sequence, respectively.

It is also possible that an SSN6-like related protein comprises the consensus amino acid sequences depicted in FIG. 9B and/or FIG. 9C.

In a further preferred embodiment of the present invention, the "ssn6-like related gene" resembles the ssn6-like gene as defined herein not only in respect of function/activity, i.e. the ability of the SSN6-like related protein being encoded by the ssn6-like related gene to regulate the expression of genes that are under control of the LLP-promoter or modified LLP promoter, and LLP-promoter sequence, respectively, but additionally originates from a microorganism being selected from the group consisting of *Komagataella pastoris* CBS 7435 (Synonym/other names: *Pichia pastoris, Pichia pastoris* CBS 7435), *Komagataella pastoris* GS115 (Synonym/other names: *Pichia pastoris, Pichia pastoris* GS115), *Scheffersomyces stipitis* CBS 6054 (Synonym/other names: *Pichia stipitis, Pichia stipitis* CBS 6054), *MNerozyma farinosa* CBS 7064 (other name: *Pichia farinosa* CBS 7064), *Candida parapsilosis, Candida orthopsilosis* Co 90-125, *Debaryomyces hansenii* CBS767, *Spathaspora passalidarum* NRRL Y-27907, *Candida albicans, Candida albicans, Candida albicans* SC5314, *Candida maltosa* Xu316, *Candida tropicalis* MYA-3404 (other name: *Candida tropicalis* T1), *Lodderomyces elongisporus* NRRL YB-4239 (other name: *Saccharomyces elongisporus*), *Clavispora lusitaniae* ATCC 4272 (genebank anamorph: *Candida lusitaniae* ATCC 42720), *Meyerozyma guilliermondii* ATCC 6260 (genebank anamorph: *Pichia guilliermondii* ATCC 6260), *Wickerhamomyces ciferrii, Ogataea parapolymorpha* DL-1 (synonym and other names: *Hansenula polymorpha, Hansenula polymorpha* DL-1, *Ogataea angusta* DL-1, *Ogataea parapolymorpha* ATCC 26012, *Ogataea parapolymorpha* DL-1, *Pichia angusta* DL-1), *Cyberlindnera fabianii* (synonyms and other names: *Hansenula fabianii, Pichia fabianii,* ... ) *Kuraishia capsulata* CBS 1993, *Dictyostelium discoideum* AX4 (belongs to social amoebae), *Tetrapisispora phaffil* CBS 4417 (synonym: *Fabospora phaffii, Dictyostelium purpureum* (belongs to social amoebae), *Pseudozyma flocculosa* PF-1, *Malassezia globosa* CBS 7966, *Botryobasidium botryosum* FD-172 SS1 (basidiomycete), *Naumovozyma dairenensis* CBS 421 (synonyme: *Saccharomyces dairenensis*), *Tetrapisispora blattae* CBS 6284, *Mucor circinelloides* f. *circinelloides* 1006PhL (Early diverging fungal lineage), *Malassezia sympodialis* ATCC 42132, *Kazachstania naganishii* CBS 8797 (*Saccharomyces naganishii*), *Saccharomyces cerevisiae* YJM789, *Saccharomyces cerevisiae* FostersB, *Saccharomyces cerevisiae, Saccharomyces cerevisiae* S288c, *Ustilago hordei* (Corn smut fungus, basidiomycete), *Meyerozyma guilliermondii* ATCC 6260 (synonym/other names: *Candida guilliermondii, Pichia guilliermondii* ATCC 6260), and *Ustilago maydis* 521 (Corn smut fungus, basidiomycete).

In a preferred embodiment, the "modified ssn6-like gene" and "modified ssn6-like related gene", and the respective proteins these genes encode, do not correspond to/are not derived from *Saccharomyces cerevisiae* ssn6 or Tup1 nucleotide or amino acid sequences, especially do not correspond to the following sequences:

SEQ ID NO: 135 (nucleotide sequence encoding SSN6)
SEQ ID NO: 136 (nucleotide sequence encoding Tup1)
SEQ ID NO: 137 (amino acid sequence of SSN6)
SEQ ID NO: 138, (amino acid sequence of Tup1).

In a further preferred embodiment, the modified eukaryotic cell comprises modified ssn6-like genes or ssn6-like related genes, but no other modified gene(s) that regulate(s) the expression of a gene that is under control of a promoter that is repressed in the presence of SSN6-like related protein or SSN6-like protein.

"Sequence identity" or "% identity" refers to the percentage of residue matches between at least two polypeptide or polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. For purposes of the present invention, the sequence identity between two amino acid sequences or nucleotide is determined using the NCBI BLAST program version 2.2.29 (Jan. 06, 2014) (Altschul et al., Nucleic Acids Res. (1997) 25:3389-3402). Sequence identity of two amino acid sequences can be determined with blastp set at the following parameters: Matrix: BLOSUM62, Word Size: 3; Expect value: 10; Gap cost: Existence=11, Extension=1; Filter=low complexity activated; Filter String: L; Compositional adjustments: Conditional compositional score matrix adjustment. For purposes of the present invention, the sequence identity between two nucleotide sequences is determined using the NCBI BLAST program version 2.2.29 (Jan. 06, 2014) with blastn set at the following exemplary parameters: Word Size: 11; Expect value: 10; Gap costs: Existence=5, Extension=2; Filter=low complexity activated; Match/Mismatch Scores: 2,-3; Filter String: L; m.

Nucleic acid sequences alternatively can be characterized by their degree of complementarity. As used herein, the term "complementary" refers to the ability of purine and pyrimidine nucleotide sequences to associate through hydrogen bonding to form double-stranded nucleic acid molecules. Guanine and cytosine, adenine and thymine, and adenine and uracil are complementary and can associate through hydrogen bonding resulting in the formation of doublestranded nucleic acid molecules when two nucleic acid molecules have "complementary" sequences. The complementary DNA sequences are referred to as a "complement." In accordance with the invention "highly stringent conditions" means hybridization at 65° C. in 5× SSPE and 50% formamide, and washing at 65° C. in 0.5× SSPE. Conditions for high stringency hybridization are described in Sambrook et al., "Molecular Cloning: A Laboratory Manual", 3rd Edition, Cold Spring Harbor Laboratory Press, (2001), incorporated herein by reference. In some illustrative aspects, hybridization can occur along the full-length of the isolated nucleic acid, or along part of its length, or to a fragment thereof.

The following list indicates examples of organisms that comprise ssn6-like related genes: *Komagataella pastoris* CBS 7435 (Synonym/other names: *Pichia pastoris, Pichia pastoris* CBS 7435), *Komagataella pastoris* GS115 (Synonym/other names: *Pichia pastoris, Pichia pastoris* GS115), *Scheffersomyces stipitis* CBS 6054 (Synonym/other names:

*Pichia stipitis, Pichia stipitis* CBS 6054), *Millerozyma farinosa* CBS 7064 (other name: *Pichia farinosa* CBS 7064), *Candida parapsilosis, Candida orthopsilosis* Co 90-125, *Debaryomyces hansenii* CBS767, *Spathaspora passalidarum* NRRL Y-27907, *Candida albicans, Candida albicans, Candida albicans* SC5314, *Candida maltosa* Xu316, *Candida tropicalis* MYA-3404 (other name: *Candida tropicalis* T1), *Lodderomyces elongisporus* NRRL YB-4239 (other name: *Saccharomyces elongisporus*), *Clavispora lusitaniae* ATCC 4272 (genebank anamorph: *Candida lusitaniae* ATCC 42720), *Meyerozyma guilliermondii* ATCC 6260 (genebank anamorph: *Pichia guilliermondii* ATCC 6260), *Wickerhamomyces ciferrii, Ogataea parapolymorpha* DL-1 (synonym and other names: *Hansenula polymorpha, Hansenula polymorpha* DL-1, *Ogataea angusta* DL-1, *Ogataea parapolymorpha* ATCC 26012, *Ogataea parapolymorpha* DL-1, *Pichia angusta* DL-1), *Cyberlindnera fabianii* (synonyms and other names: *Hansenula fabianii, Pichia fabianii, . . .* ), *Kuraishia capsulata* CBS 1993, *Dictyostelium discoideum* AX4 (belongs to social amoebae), *Tetrapisispora phaffii* CBS 4417 (synonym: *Fabospora phaffii, Dictyostelium purpureum* (belongs to social amoebae), *Pseudozyma flocculosa* PF-1, *Malassezia globosa* CBS 7966, *Botryobasidium botryosum* FD-172 SS1 (basidiomycete), *Naumovozyma dairenensis* CBS 421 (synonyme: *Saccharomyces dairenensis*), *Tetrapisispora blattae* CBS 6284, *Mucor circinelloides f. circinelloides* 1006PhL (Early diverging fungal lineage), *Malassezia sympodialis* ATCC 42132, *Kazachstania naganishii* CBS 8797 (*Saccharomyces naganishii*), *Saccharomyces cerevisiae* YJM789, *Saccharomyces cerevisiae* FostersB, *Saccharomyces cerevisiae, Saccharomyces cerevisiae* S288c, *Ustilago hordei* (Corn smut fungus, basidiomycete), *Meyerozyma guilliermondii* ATCC 6260 (synonym/other names: *Candida guilliermondii, Pichia guilliermondii* ATCC 6260), *Ustilago maydis* 521, (Corn smut fungus, basidiomycete).

Within the meaning of the present invention, the term "wildtype" denotes that a certain matter is present in its natural occurring state, and thus exerts its natural function and/or activity.

A "certain matter" can for instance be an organism such as a microorganism, a cell, or, preferably, a certain protein such as the SSN6 protein or the SSN6-like protein. The wildtype state, or wildtype form, respectively, of a certain matter is distinguishable from mutant forms of said matter, as for instance structural mutant forms can result from modifications that are carried out artificially, such as by in vitro, in vivo or ex vivo modifications or manipulations. Modifications that can be carried out artificially are described elsewhere herein. An organism that comprises modifications is "modified" compared to its wildtype form with regard to the modified structure.

Within the meaning of the present invention, the term "function" defines the physiological role of a certain matter, such as the SSN6-like protein or SSN6-like related protein, and the term "activity" defines to which extent said certain matter exerts its function. An example of a physiological role of a certain matter is the regulating, preferably repressing, role of SSN6-like protein or SSN6-like related protein, on the activity of the LLP-promoter, and hence, on the expression of genes that are under control of said promoter.

Within the meaning of the present invention, the term "wildtype function" denotes the function a certain structure or matter (such as an organism, a protein, or a gene) exerts in its natural state. Accordingly, the term "wildtype activity" denotes the activity a certain structure exerts in its natural state.

Within the meaning of the present invention, an organism can be modified only with regard to a single specific structural and/or functional feature, or with regard to multiple structural and/or functional features. Specific structural and/or functional features that are modified are features that modulate (i.e. influence, either positively or negatively, preferably negatively) the expression of the ssn6 gene or ssn6-like gene.

An example of a specific feature that can be modified is for instance the nucleotide sequence of ssn6-like gene or ssn6-like related gene, with this gene comprising a coding sequence and a regulatory sequence that influences the expression of said genes as disclosed elsewhere herein.

Regulatory sequences are sequences that control the expression of certain genes. Within the meaning of the present invention, said regulatory sequences are for example sequences that control the expression of the ssn6-like gene, the ssn6-like related gene or the LLP-gene, such as promoters, enhancers, terminators, silencers, IRES-sequences, ribosome-binding sites, and sequences stabilizing or destabilizing the mRNA by secondary structures.

Within the meaning of the present invention, the term "heterologous nucleotide sequence" is a polynucleotide that does not naturally occur in the cell, e.g. because the nucleotide sequence of the polynucleotide does not naturally occur in eukaryotic cells, such as eukaryotic cells as defined elsewhere herein.

Within the meaning of the present invention, the names "*Komagataella pastoris*" and "*Pichia pastoris*" are synonymous.

The names "NRRL Y-11430, CBS7435" are synonymously used in the present invention. The genome of CBS7435 comprises chromosomes 1 to 4 and a mitochondrium. The respective nucleotide sequences have the following GenBank Accession Numbers: Chromosome 1: FR839628.1; Chromosome 2: FR839629.1; Chromosome 3: FR839630.1; Chromosome 4: FR839631.1; Mitochondrium: FR839632.1 (Publication: High-quality genome sequence of Pichia pastoris CBS7435, Kuberl A, Schneider J, Thallinger G G, Anderl I, Wibberg D, Hajek T, Jaenicke S, Brinkrolf K, Goesmann A, Szczepanowski R, Puhler A, Schwab H, Glieder A, Pichler H, J Biotechnol, volume 154 issue 4, pages 312-320 year 2011).

A "vector" is a replicon, such as plasmid, phage, bacterial artificial chromosome (BAC) or cosmid, into which another DNA segment (e.g. a foreign gene) may be inserted so as to bring about the replication of said inserted DNA segment, resulting in expression of said inserted sequence. Vectors may comprise a promoter and one or more control elements (e.g., enhancer elements) that are homologous or heterologous to said inserted DNA segment but are recognized and used by the host cell. A "replicon" is any genetic element (e.g., plasmid, chromosome, virus) that functions as a unit of DNA replication within a cell. A replicon can be an autonomous unit. This means that it is capable of replication under its own control. Within the meaning of the present invention, the vector comprises a promoter, wherein said promoter is characterized in that it is repressed in the presence of SSN6-like related protein or SSN6-like protein if said vector is introduced into a suitable host cell. In a preferred embodiment of the present invention, the vector comprises a promoter for the coding sequence of the LLP-protein and/or for the coding sequence of a protein of interest, wherein said promoter is characterized in that it is repressed in the presence of SSN6-like related protein or SSN6-like protein if said vector is introduced into a suitable host cell.

A common type of vector is a "plasmid", which generally is a self-contained molecule of double-stranded DNA, usually of bacterial origin, that can readily accept additional (foreign) DNA and which can be readily introduced into a suitable host cell. In general, vectors enable the introduction of nucleotide sequences into a host cell, so as to transform the host and, optionally, to promote expression and/or replication of the introduced sequence.

A vector often contains coding DNA and regulatory sequences such as promoter DNA and has one or more restriction sites suitable for inserting additional, e.g. foreign such as heterologous, DNA. Promoter DNA and coding DNA may be from the same gene or from different genes, and may be from the same or different organisms. Vectors, such as recombinant cloning vectors, will often include one or more replication systems for cloning or expression, one or more markers for selection in the host, e.g. antibiotic resistance, and one or more expression cassettes. Vector, or vector constructs, respectively, may be produced using conventional molecular biology and recombinant DNA techniques within the skill of the art. Such techniques are explained fully in the literature. See, e.g., Sambrook, Fritsch & Maniatis, Molecular Cloning: A Laboratory Manual, 4$^{th}$ Edition (2012) Cold Spring Harbor Laboratory Press, Cold Spring Harbor, N.Y. (herein "Sambrook et al., 2012"); DNA Cloning: A Practical Approach, Volumes I and II (D. N. Glover ed. 1985); F. M. Ausubel et al. (eds.), Current Protocols in Molecular Biology, John Wiley & Sons, Inc. (1994).

Generally, the specific structural elements of a vector depend on the intended use of said vector. For instance, in order to propagate a vector in a host cell, it may contain one or more "origins of replication" sites (often also termed "ori"), which is a specific nucleic acid sequence at which replication is initiated. Accordingly, the term "origin of replication" or "ori" refers to a nucleic acid sequence that initiates nucleic acid replication.

"Ori T" refers to an "origin of transfer" that permits the transfer of the vector from one bacterial cell to another.

Dependent on in which organism/cell the (expression) vector is intended for being used, a person skilled in the art knows which markers have to be present in the vector. If, for instance, the vector is intended for being used in yeast, amongst others, commonly used yeast markers are present, such as beta-galactosidase, Zeocin, Geneticin, URA3, HIS3, LEU2, TRP1 and LYS2. If the vector is intended for being used in bacteria such as E. coli, amongst others an ori (see above) and/or selectable markers such as genes conferring antibiotic resistance can be present.

Suitable selectable markers depend on the respective system that is used and are known to a person skilled in the art. Transformed microorganisms, that is, those containing recombinant molecules such as a vector (expression vector) or plasmid, may be selected with a variety of positive and/or negative selection methods or markers. For instance, a positive selection marker can be a gene that allows growth in the absence of an essential nutrient, such as an amino acid. A variety of suitable positive/negative selection pairs are available and known in the art. For example, various amino acid analogs known in the art could be used as a negative selection, while growth on minimal media (relative to the amino acid analog) could be used as a positive selection. Visually detectable markers are also suitable for being uses in the present invention, and may be positively and negatively selected and/or screened using technologies such as fluorescence activated cell sorting (FACS) or microfluidics. Examples of detectable markers include various enzymes, prosthetic groups, fluorescent markers, luminescent markers, bioluminescent markers, and the like. Examples of suitable fluorescent proteins include, but are not limited to, yellow fluorescent protein (YFP), green fluorescence protein (GFP), cyan fluorescence protein (CFP), umbelliferone, fluorescein, fluorescein isothiocyanate, rhodamine, dichlorotriazinylamine fluorescein, dansyl chloride, phycoerythrin and the like. Examples of suitable bioluminescent markers include, but are not limited to, luciferase (e.g., bacterial, firefly, click beetle and the like), luciferin, aequorin and the like. Examples of suitable enzyme systems having visually detectable signals include, but are not limited to, galactosidases, glucorinidases, phosphatases, peroxidases, cholinesterases and the like. In other aspects, the positive selection marker is a gene that confers resistance to a compound, which would be lethal to the cell in the absence of the gene. For example, a cell expressing an antibiotic resistance gene would survive in the presence of an antibiotic, while a cell lacking the gene would not. For instance, the presence of a tetracycline resistance gene could be positively selected for in the presence of tetracycline, and negatively selected against in the presence of fusaric acid. Suitable antibiotic resistance genes include, but are not limited to, genes such as ampicillin-resistance gene, neomycin-resistance gene, blasticidin-resistance gene, hygromycin-resistance gene, puromycin-resistance gene, chloramphenicol-resistance gene, apramycin-resistance gene, geneticin-resistance gene, zeocin-resistance gene, and the like. In certain aspects, the negative selection marker is a gene that is lethal to the target cell in the presence of a particular substrate. For example, the thyA gene is lethal in the presence of trimethoprim. Accordingly, cells that grow in the presence trimethoprim do not express the thyA gene.

In order to purify the recombinant proteins, the respective (expression) vectors used often comprise suitable purification sequences (purification markers). For instance, a vector may comprise a C-terminal c-myc epitope and polyhistidine sequence for detection and purification of the recombinant protein(s).

As described elsewhere herein, a vector can be used for introducing a nucleic acid sequence into a host cell, or into the host cell's genome, such as the genome of a yeast such as P. pastoris, or of a bacterium, such as E. coli. The introduction of (heterologous) nucleic acid into a host cell's nucleic acid is denoted as "recombination". Such a recombination process can be targeted, i.e. take place at a defined, desired site of the genome (nucleic acid sequence) it is to be introduced. In this case, the recombination is denoted as "homologous recombination" (or "targeted recombination"/ "targeted integration"). Also, the recombination process can be random ("random recombination"/"random integration"). In this case, the recombination is non-homologous.

The term "homologous recombination" refers to a type of genetic recombination, a process of physical rearrangement occurring between two different strands of DNA molecules. Homologous recombination involves the alignment of identical or similar sequences, a crossover between the aligned homologous DNA strands of the two molecules, and breaking and repair of the DNA to produce an exchange of material between the strands. Homologous recombination is distinguished from other types of recombination. For example, "site specific recombination", as exemplified by invertible elements, resolvases, and some phage integration events are examples of non-homologous recombination. Though in many cases identical or similar sequences are required at the two recombining sites, the sequences are short, distinguishing them from the longer stretches (hundreds of base pairs) used in homologous recombination. (J Rubnitz and S Subramani. 1984, Mol Cell Biol. 4: 2253-2258).

If the vector aligns in a non-homologous region of the target nucleic acid, the recombination is random.

Within the meaning of the present invention, in connection with homologous recombination, two DNA sequences are "substantially homologous" if they are able to mediate a homologous recombination. This may for instance the case when at least about 80%, preferably at least about 90% or 95%, more preferably at least about 97% or 98% of the nucleotides match over a defined length of the DNA sequences, as determined by sequence comparison algorithms known to a person skilled in the art and described elsewhere in this application. It is also possible that two DNA sequences exhibit 100% match of the nucleotides over a defined length. In this case, the two DNA sequences are homologous to each other. Within the meaning of the present invention, a DNA sequence in the vector, e,g. the expression vector, is substantially homologous, or homologous, to a desired target integration site in the host cell.

Within the meaning of the present invention, both integration/recombination events can occur, i.e. the homologous recombination and the random recombination. For instance, if it is desired to replace a certain gene (or coding sequence) by the gene of interest, then a homologous recombination will be carried out. Within the meaning of the present invention, it may be desired to replace a gene that is under the control of a promoter that is repressable by SSN6-like related or SSN6-like protein, such as a nucleic acid sequence encoding LLP protein ("Option 1" in FIG. 3C).

Within the meaning of the present invention it is however also possible that it may be desired to not replace a gene that is under the control of a promoter that is repressable by SSN6-like related or SSN6-like protein, such as a nucleic acid sequence encoding LLP protein, but to express said gene (such as the gene encoding LLP), and to additionally express the gene of interest ("Option 2" in FIG. 3D). In such a case, a random (heterologous) recombination is carried out.

Within the meaning of the present invention, the term "gene of interest" (GOI) refers to a gene that is intended for being expressed in a host cell. In the present invention, genes of interest are genes selected for example from the group encoding enzymes, antibodies or fragments thereof, hormones, structural proteins (e.g. albumin) and protein-antigens present in vaccines.

Within the meaning of the present invention, the term "expression cassette" refers to a part of vector DNA that is for instance used for cloning and/or transformation. An expression cassette comprises one or more genes and sequences controlling their expression. An expression cassette can be inserted in a nucleotide sequence such as a genome for instance by means of homologous recombination or by heterologous recombination.

Within the meaning of the present invention, the term "host cell" denotes any cell that, under suitable conditions, is capable of propagating or expressing a vector such as an expression vector. For instance, in the present invention an expression vector can comprise a promoter, wherein said promoter is characterized in that it is repressed in the presence of SSN6-like protein or SSN6-like related protein.

The host cell that comprises a vector can be any suitable host cell, such as a bacterial cell, preferably an *E. coli* cell. It is also possible that the vector, such as the expression vector, is present in a eukaryotic cell. In this case, the host cell is said eukaryotic cell. If, as described elsewhere herein, said eukaryotic cell is modified with regard to the ssn6-like gene, ssn6-like related gene, SSN6-like protein or SSN6-like related protein, the eukaryotic cell is denoted as "modified eukaryotic cell". In a preferred embodiment of the present invention, the eukaryotic cell is a fungal cell, preferably a yeast cell, more preferably selected from the group consisting of *Saccharomyces, Kluyveromyces, Candida, Hansenula, Pichia, Komagataella* and *Torulopsis*, even more preferably the eukaryotic cell is a *Pichia* cell, most preferably a *Pichia pastoris* cell.

If the expression vector is intended for being present in a eukaryotic cell, which may be modified or not, it is preferred that the expression vector comprises features selected from any one of the following: a selection marker; a purification marker; a signal sequence, preferably the yeast alpha-factor secreting signal sequence, the yeast KILM1 signal peptide, the yeast PHO1 signal peptide, or the yeast SUC2 signal peptide, more preferably an alpha-factor secreting signal sequence, even more preferably the MFalpha pre-pro signal sequence; an origin of replication; and/or a nucleotide sequence for targeted (option 1, of FIG. 3C) and/or random integration (option 2, FIG. 3D) into the genome of a host cell.

Within the meaning of the present invention, the eukaryotic cells that are used are modified compared to their wildtype cell. This means that the modified eukaryotic cell (at least) comprises a modified ssn6-like related gene or a modified ssn6-like gene; and/or a modified, preferably reduced, expression level of SSN6-like related protein or of SSN6-like protein, or that an ssn6-like related gene or an ssn6-like gene is deleted resulting in the complete lack of said SSN6-like related protein or complete lack of said SSN6-like protein.

The effect of the respective modifications is that the modified eukaryotic cell is not able to provide an SSN6-like related protein or an SSN6-like protein that exerts its wildtype function and/or wildtype activity, preferably with respect to regulating the LLP promoter; and/or the amount of SSN6-like related protein or of SSN6-like protein being present in the modified eukaryotic cell differs (preferably in that it is reduced) from the amount of SSN6-like related protein or of SSN6-like protein being present in its wildtype form; and/or no SSN6-like related protein or SSN6-like protein is present in the modified cell. This, in turn, has the effect that said modified eukaryotic cell, compared to its wildtype cell, exhibits different (preferably reduced) SSN6-like related protein or SSN6-like protein activity and/or function, preferably with respect to its activity and/or function in regulating the LLP promoter.

As described elsewhere herein, if the modified eukaryotic cell is not able to provide a proper, sufficiently working SSN6-like related protein or SSN6-like protein (e.g. in terms of function, activity, and/or amount), as a result the regulatory sequences that are controlled by said protein, such as promoters, like the LLP promoter, are not affected in their function (e.g. are not repressed) any more. This, in turn, results in an overexpression of the protein that is under control of said regulatory polynucleotide sequence.

In other words, proper, sufficiently working SSN6-like related protein or SSN6-like protein represses the LLP promoter, which means that the LLP promoter exhibits reduced function, when compared to the function of the LLP promoter that is not repressed by said proteins. As to the term "reduced", reference is made to the description elsewhere herein.

Within the meaning of the present invention, the term "overexpression" defines that the expression of a protein (encoded for instance by the gene of interest) in a cell such as a (modified) eukaryotic cell is at levels greater than normal in a wildtype cell. For instance, in the present invention the modified eukaryotic cell can be used in order to overexpress a gene of interest.

Within the meaning of the present invention, the term "modification" denotes any suitable amendment that is known to a person skilled in the art that can be applied to a nucleotide sequence or gene, respectively, that results in one or more of the following effects (if the modified nucleotide sequence is expressed in a suitable expression system): the SSN6-like or SSN6-like related protein does not exert its wildtype function and/or wildtype activity; the amount of SSN6-like or SSN6-like related protein being present is lower as compared to non-modified cells; and/or no SSN6-like or SSN6-like related protein is present at all. In an embodiment of the present invention, the nucleotide sequence of the ssn66-like or ssn66-like related gene, respecticely, is modified by introduction of a point mutation, e.g. substitution, insertion or deletion of a single or more nucleotides; by partial or complete deletion; and/or by replacement by a different, e.g. heterologous, nucleotide sequence.

It is also possible that the expression level of the affected SSN6-like or SSN6-like related protein is modified, for instance by introduction of a point mutation, e.g. substitution, insertion or deletion of a single or more nucleotides in regulatory polynucleotide sequences of the affected ssn6-like or ssn6-like related nucleotide sequence or ssn6-like or ssn6-like related gene, respectively; by partial or complete deletion of regulatory polynucleotide sequences of the affected ssn6-like or ssn6-like related nucleotide sequence or ssn6-like or ssn6-like related gene, respectively; and/or by replacement of the regulatory polynucleotide sequences of the affected ssn6-like or ssn6-like related nucleotide sequence or ssn6 or ssn6-like gene, respectively, by different, e.g. heterologous, nucleotide sequences. The regulatory polynucleotide sequences are selected from the group as defined elsewhere herein.

In order to assess whether a modification in the meaning of the present invention has been carried out on a nucleotide sequence, suitable sequence alignments can be carried out: For instance, the sequence of the potentially modified polynucleotide sequence can be aligned with the respective wildtype counterpart. The resulting alignment indicates whether a modification has been carried out, and if so, which kind of modification.

Within the meaning of the present invention, the term "coding sequence" denotes a nucleotide sequence (e.g. heterologous or homologous nucleotide sequence or heterologous or homologous polynucleotide, respectively), such as a nucleotide sequence being comprised in a gene of interest, that encodes an expression product, such as an RNA or polypeptide, that, when expressed, results in production of the product (e.g. polypeptide (for instance a heterologous polypeptide), such as enzymes, antibodies or fragments thereof, hormones, or protein-antigens present in vaccines).

Here, the term "a promoter that is repressed" defines that the promoter is not able to exert its full, natural function and its full, natural activity. An example of such a promoter that is repressed in the presence of SSN6-like or SSN-like related protein is the LLP promoter: It is not yet known which mechanism is underlying said repression, however it is speculteted that the repression could be based on alteration of the local chromatin structure, or on interaction with the general transcription machinery (Smith et al., TIBS 25, July 2000, 325-330).

Within the meaning of the present invention, as a result of the repression of the promoter, the expression of a gene that is under control of said promoter is influenced to the effect that the respective encoded protein is not expressed; and that the amount of said expressed protein differs from the wildtype amount of said protein.

Within the meaning of the present invention a coding sequence (e.g. of a heterologous polynucleotide) is "under control of" (or the like) a transcriptional or translational control sequence (regulatory polynucleotide sequence) when the regulatory polynucleotide sequence directs RNA, preferably mRNA, which then may be spliced (if it contains introns) and, optionally, translated into a protein encoded by the coding sequence. In an embodiment of the present invention, a gene (such as a gene of interest) is under control of the LLP promoter. This means that as long as the promoter works as in a wildtype situation (for instance, is repressed by SSN6-like protein or SSN6-like related protein), a gene that is under control of said promoter is not expressed or expressed at low levels when the cells are cultivated in standard conditions. As soon as the LLP promoter is derepressed due to the presence of a modified SSN6-like related protein or SSN6-like protein or different cultivation conditions, a gene that is under control of this promoter is expressed at high to very high levels (compared to a situation where the promoter is not repressed). Based on the ratio underlying the present invention, it is likely that a SSN6-like protein or a SSN6-like related protein might be blocked not only be mutation of the ssn6-like gene or the ssn6-like related gene, but also by inhibitors of ssn6-like gene or protein or by inhibitors of ssn6-like related gene or protein, which also could result in increased activity of the LLP-promoter.

The term "functional" defines that the respective matter exhibits its natural function.

The term "selecting" refers to the identification and isolation of a recipient cell that contains the vector of interest. Transformed microorganisms, that is, those containing recombinant molecules such as a vector or plasmid, may be selected with a variety of positive and/or negative selection methods or markers. Details according to such selection methods and markers are described elsewhere in this appilication. Negative selection markers include, but are not limited to, genes such as thyA, sacB, gnd, gapC, zwJ, talA, taiB, ppc, gdhA, pgi, Jbp, pykA, cit, acs, edd, icdA, groEL, secA and the like.

In general, the term "expression system" denotes a system that is specifically designed for the production of a gene product of choice, also referrd to herein as protein of interest (POI). In the present invention, the expression system comprises a modified ssn6-like related gene or a modified ssn6-like gene, or an ssn6-like related gene or an ssn6-like gene and a modified regulatory polynucleotide sequence that is involved in the reglation of the expression of said genes, to the effect that said expression system is not able to express an SSN6-like related protein or SSN6-like protein, that SSN6-like related protein or SSN6-like protein is expressed that does not exert its wildtype function and/or wildtype activity, and/or that an amount of SSN6-like related protein or SSN6-like protein is expressed that differs, preferably is lower, when compared to the amount of SSN6-like related protein or of SSN6-like protein that is expressed by said expression system when the corresponding wildtype polynucleotide sequence is expressed by such an expression system under the same conditions.

The expression system of the present invention is a eukarytic expression system, i.e. an expression system that comprises a eukaryotic cell. In particular, within the meaning of the present invention, said eukaryotic cell is modified as described elsewhere herein.

DETAILED DESCRIPTION OF THE INVENTION

The present invention is now described in more detail by preferred embodiments and examples, which are however presented for illustrative purpose only and shall not be understood as limiting the scope of the present invention in any way.

Although expression systems for expressing proteins are widely known in prior art, these expression systems often exhibit disadvantages, for instance with regard to the yield of the expression product, or with regard to the expression system itself.

The present invention is based on the surprising general finding that an improved constitutive eukaryotic expresson system can be generated by modifying an ssn6-like related gene or ssn6-like gene ("ssn6-like related/ssn6-like gene") that is present in a eukaryotic cell, and/or by modifying the expression level of SSN6-like related protein or SSN6-like protein; or by deleting the ssn6-like related gene or ssn6-like gene, respectively to the effect that the resulting modified eukaryotic cell is not able to provide an SSN6-like related protein or an SSN6-like protein that exerts its wildtype function and/or wildtype activity in particular with regard to regulatory sequences such as a promoter that is regulated by said proteins (such as the LLP promoter); the amount of SSN6-like related protein or of SSN6-like protein being present in the modified eukaryotic cell differs (preferably is lower) from the amount of SSN6-like related protein or of SSN6-like protein being present in its wildtype form, to the effect that said proteins are not able to exert their wildtype function and/or activity in particular with regard to regulatory sequences such as a promoter that is regulated by said proteins; and/or no SSN6-like related protein or SSN6-like protein ("SSN6-like related/SSN6-like protein") is present in the modified cell, again to the effect that said proteins are not able to exert their wildtype function and/or activity in particular with regard to regulatory sequences such as a promoter that is regulated by said proteins. Thus, by preventing the SSN6-like related protein or SSN6-like protein from exerting its natural (wildtype) function, which function comprises the repressive direct and/or indirect interactions with regulatory sequences such as promoters (e.g. the LLP promoter), the expression of a gene that is under control of said regulatory sequences (e.g. LLP promoter) in a suitable expression system is, at least to a certain degree, not repessed any more. In other other words, the respective gene being under control of said promoter is overexpressed compared to its wildtype expression.

By applying the principle underlying the present invention, a eukaryotic expression system is provided, which is for instance improved with regard to expression product yield compared to the yield that is obtained when applying prior art expression systems. Moreover, the inventive expression system is improved with regard to safety aspects: Contrary to certain prior art eukaryotic expression systems, the present eukaryotic expression system is not based on the commonly used AOX (alcohol oxidase) promoters, which are tightly regulated by methanol. The presence of flammable and toxic methanol represents a major security risk, and also imposes a risk on alcohol-sensitive expression products or host cells. Especially in large scale fermentation of recombinant proteins the use of methanol is a serious safety and envirionmental risk. Alternative eukaryotic expression systems that use promoters that are not regulated by methanol are for instance based on the constitutive GAP (glyceraldehyde-3-phosphate dehydrogenase) promoter. However, the resulting yield for instance when applying a GAP-based expression system leaves much to be desired.

Within the meaning of the present invention it has been surprisingly found that the modification of an ssn6-like related gene or of an ssn6-like gene and/or the modification of the expression level of SSN6-like related protein or SSN6-like protein that is present in a eukaryotic cell to the effect that the resulting modified eukaryotic cell is not able to exert the wildtype function of SSN6-like related protein or SSN6-like protein with regard to a regulatory sequence that is regulted by said SSN6-like related protein or SSN6-like protein, such as a promoter (e.g. the LLP promoter), results in an enhanced expression of the gene that is under control of said regulatory sequence.

Thus, the present invention provides a modified eukaryotic cell, which is modified compared to its wildtype cell at least in that it comprises a modified ssn6-like related gene or a modified ssn6-like gene, and/or a modified expression level of SSN6-like related protein or of SSN6-like protein, or in that an ssn6-like related gene or an ssn6-like gene is deleted, respectively to the effect that the modified eukaryotic cell is not able to provide an SSN6-like related protein or an SSN6-like protein that exerts its wildtype function and/or wildtype activity, the amount of SSN6-like related protein or of SSN6-like protein being present in the modified eukaryotic cell differs from the amount of SSN6-like related protein or of SSN6-like protein being present in its wildtype form, and/or no SSN6-like related protein or SSN6-like protein is present in the modified cell.

In accordance with the ratio underlying the present invention, the resulting modified eukaryotic cell, when compared to its wildtype cell, exhibits different SSN6-like related protein or SSN6-like protein activity and/or function, preferably with respect to its activity and/or function in regulating the expression of a gene.

Whenever the term "wildtype function" is used in connection with SSN6-like related protein or SSN6-like protein, or the respective genes encoding said proteins, the function with regard to a regulatory sequence that is regulated by SSN6-like related protein or SSN6-like protein, such as a promoter (preferably the LLP promoter), is referred to.

As it is known to a person skilled in the art, the expression of a gene is, amongst others, regulated by a complex interplay of various factors that contribute to the regulation of the expression of (a) certain gene(s), such as promoters, enhancers, terminators, silencers, transcription factors, IRES-sequences, ribosome-binding sites, and sequences stabilizing or destabilizing the mRNA by secondary structures or enhancers.

Thus, in a preferred embodiment, the resulting modified eukaryotic cell exhibits different SSN6-like related protein or SSN6-like protein activity and/or function with regard to any promoter that is regulated by said proteins, preferably the LLP promoter. Hence, it is a preferred embodiment of the present invention that the modified eukaryotic cell, when compared to its wildtype cell, exhibits different SSN6-like related protein or SSN6-like protein activity and/or function with regard to regulating the expression of genes that are under control of the LLP promoter. The activity and/or function of said proteins (SSN6-like related and SSN6-like) results in that the genes that are under control of said promoter (LLP-promoter) are overexpressed.

The different activity and/or function of the SSN6-like related protein or SSN6-like protein can be any different activity and/or function that results in an overexpression of the respective gene that is under control of the affected regulatory sequence. For example an SSN6-like related protein or SSN6-like protein might be altered in its activity and/or function by "gain of function" or "loss of function" modifications. If several copies of different modified versions or wild-type SSN6-like related protein or SSN6-like protein are present within a cell at the same time, certain SSN6-like related proteins or SSN6-like proteins might be dominant regarding their activity and/or function. "Loss-of-function" mutants comprise a mutation that results in reduced or abolished protein function. "Gain-of-function" mutants comprise a mutation that results in an abnormal activity on a protein. Preferably, it is a reduced activity and/or function of the SSN6-like related protein or of the SSN6-like protein. It can also be that there is no SSN6-like related protein or SSN6-like protein at all present in the modified eukaryotic cell, or that there is no SSN6-like related protein or SSN6-like protein within the detection limit of commonly know methods such as for example RT-PCR, qPCR or other PCR-related techniques, western blotting, ELISA, or other immunological detection assays, reporter gene assays, mass spectrometric detection methods, chip assays detecting proteins or nucleic acids, etc.

In order to arrive at a modified eukaryotic cell that exhibits different, preferably reduced, more preferably essentially no, SSN6-like related protein or SSN6-like protein function and/or activity, the ssn6-like related gene or ssn6-like gene can be modified. This modification can for instance have taken place in a coding sequence encoding the respective protein, and/or in a respective regulatory sequence. A regulatory sequence that can be modified is for instance a promoter, enhancer, terminator, silencer, IRES-sequence, ribosome-binding site, and sequence stabilizing or destabilizing the mRNA by secondary structures or enhancer.

According to the present invention, the above modifications on the regulatory and/or coding regions of the genes encoding SSN6-like related protein and/or SSN6-like protein have an effect on the expression level of the SSN6-like related protein or SSN6-like protein in that the modified eukaryotic cell is not able to express said proteins, or that the amount of said proteins is different, preferably reduced, when compared with its wildtype form. The above modifications can also have an effect on the function and/or activity of SSN6-like related protein or SSN6-like protein in that said proteins do not exert their wildtype function and/or activity, It is also possible to arrive at a modified eukaryotic cell exhibiting impaired SSN6-like related/SSN6-like protein as defined above by impairing the transcription or translation of the gene encoding SSN6-like related/SSN6-like protein. Transkription and translation can be impaired by any suitable method that is known to a person skilled in the art, for instance translation can be impaired by hybridizing a complementary sequence or a partial sequence thereof to the mRNA transcript. The partial sequence of the complementary sequence is for example selected from siRNA, antisense RNA, ribozyme, and triplex RNA or DNA, etc.

Irrespective of whether the regulatory and/or coding regions of the ssn6-like related/ssn6-like gene is modified, or whether the transcription and/or translation of the gene encoding SSN6-like related/SSN6-like protein is impaired, as a result, the modified eukaryotic cell is not able to provide an SSN6-like related protein or an SSN6-like protein that exerts its wildtype function and/or wildtype activity, the amount of SSN6-like related protein or of SSN6-like protein being present in the modified eukaryotic cell differs from the amount of SSN6-like related protein or of SSN6-like protein being present in its wildtype form, and/or no SSN6-like related protein or SSN6-like protein is present in the modified cell, as it is disclosed elsewhere herein.

The ssn6-like related/ssn6-like gene and/or the expression level of the SSN6-like related/SSN6-like protein can be modified by any suitable method that is known to a person skilled in the art. For instance, the ssn6-like related/ssn6-like gene and/or the expression level of the SSN6-like related/SSN6-like protein is modified by introduction of one or more point mutations, e.g. substitution, insertion or deletion of a single or more nucleotides in the polynucleotide sequence of the ssn6-like related gene or of the ssn6-like gene, partial or complete deletion of the polynucleotide sequence of the ssn6-like related gene or of the ssn6-like gene, and/or partial or complete replacement of the polynucleotide sequence of the ssn6-like related gene or of the ssn6-like gene by a different, e.g. heterologous, nucleotide sequence.

In a preferred embodiment, the total activity, function, preferably gene regulatory function, and/or amount of SSN6-like related protein or SSN6-like protein of the modified eukaryotic cell is at most 20%, preferably at most 15%, more preferably at most 10%, even more preferably at most 5% of the activity, function and/or amount of SSN6-like related protein or SSN6-like protein of its wildtype form, and most preferably there is no activity and/or no function of the SSN6-like related protein or SSN6-like protein of the modified eukaryotic cell at all.

Within the meaning of the present invention, the term "total activity, function, and/or amount of SSN6-like related protein or SSN6-like protein of the modified eukaryotic cell" defines the overall activity, function, and/or amount of SSN6-like related protein or SSN6-like protein of a sample of modified eukaryotic cells. For instance, in order to assess whether the activity, function, and/or amount of SSN6-like related protein or SSN6-like protein of the modified eukaryotic cells differs from the corresponding feature of the wildtype cells, the total amount of SSN6-like protein being present in a sample of a certain number of wildtype cells is compared with the total amount of SSN6-like protein being present in a sample of essentially the same number of modified eukaryotic cells.

Within the meaning of the present invention, the modified eukaryotic cell can be any suitable cell, i.e. any suitable eukaryotic cell that comprises, in its wildtype form, a polynucleotide sequence encoding SSN6-like related/SSN6-like protein. In a preferred embodiment, said suitable cell additionally comprises a nucleotide sequence representing the LLP promoter. In order to determine whether a eukaryotic cell comprises the above defined sequences, any suitable method that is known to a person skilled in the art can be used, for instance techniques such as northern blotting, real time PCR, reverse transcriptase quantitative PCR (RT-qPCR), or microarray hybridization experiments. Microarray hybridization expriments can be used to quantify the expression of hundreds to thousands of genes at the same time. Suitable protocols can for instance be found in Sambrook et al.

In a preferred embodiment of the present invention, the modified eukaryotic cell is a fungal cell, preferably a yeast cell, more preferably selected from the group consisting of *Saccharomyces* species (e.g., *Saccharomyces cerevisiae*), *Kluyveromyces* species (e.g., *Kluyveromyces lactis*), *Torulaspora* species, *Yarrowia* species (e.g., *Yarrowia lipolitica*), *Schizosaccharomyces* species (e.g., *Schizosaccharomyces pombe*), *Pichia* species (e.g., *Pichia pastoris* or *Pichia methanolica*), *Hansenula* species (e.g., *Hansenula polymorpha*), *Torulopsis* species, *Komagataella* species, *Candida* species (e.g., *Candida boidinii*), and *Karwinskia* species, even more preferably the eukaryotic cell is a *Pichia* cell, most preferably a *Pichia pastoris* cell according to current classification.

In a further preferred embodiment, the modified eukaryotic cell is a *P. Pastoris* cell, preferably a cell of a strain selected from the group consisting of NRRL Y-11430, CBS704, GS115, and KM71.

As disclosed herein, the modified eukaryotic cell according to the present invention can comprise a modified ssn6-like related gene or a modified ssn6-like gene. Thus, in a further embodiment, the modified eukaryotic cell comprises a polynucleotide sequence which represents a modification of SEQ ID NO: 1.

As explained elsewhere herein, it has been found that a modification of ssn6-like related/ssn6-like gene according to the present invention, i.e. a modification that results in a modified expression of SSN6-like related/SSN6-like protein, results in an overexpression of genes that are under control of a promoter that is regulated by SSN6-like related/SSN6-like protein, such as the LLP promoter. Thus, the present invention also refers to a polynucleotide sequence comprising a modified ssn6-like related gene or a modified ssn6-like gene comprising a coding sequence and a regulatory sequence, wherein, if said polynucleotide sequence is expressed in a suitable expression system, essentially no SSN6-like related protein or SSN6-like protein is expressed, or SSN6-like related protein or SSN6-like protein is expressed that does not exert its wildtype function and/or wildtype activity, preferably with respect to its activity and/or function in regulating gene expression, more preferably in regulating the expression of genes that are under control of the LLP promoter, and/or an amount of SSN6-like related protein or SSN6-like protein is expressed that differs from the amount of SSN6-like related protein or of SSN6-like protein that is expressed when the corresponding wildtype polynucleotide sequence is expressed under comparable or the same conditions.

In a preferred embodiment, the amount of SSN6-like related protein or SSN6-like protein that is expressed differs from the amount of SSN6-like related protein or of SSN6-like protein that is expressed when the corresponding wildtype polynucleotide sequence is expressed under comparable or the same conditions in that it is reduced.

In a further embodiment, the above polynucleotide consists of said modified ssn6-like/ssn6 gene.

In a preferred embodiment, the amount of SSN6-like related/SSN6-like protein is reduced, or there is no SSN6-like related protein or SSN6-like protein present at all, compared to the amount of SSN6-like related/SSN6-like protein that is expressed when the corresponding wildtype polynucleotide sequence is expressed under comparable or the same conditions.

The modifications can be carried out in the regulatory sequence (regulatory region) and/or in the coding sequence (coding region) of the ssn6-like related/ssn6-like gene. The regulatory sequence can be any regulatory sequence, preferably the regulatory sequence is selected from the group comprising or consisting of promoters, enhancers, terminators, silencers, IRES-sequences, ribosome-binding sites, and sequences stabilizing or destabilizing the mRNA by secondary structures, more preferably said regulatory sequence is selected from the group consisting of promoters, enhancers, and terminators.

The ssn6-like related/ssn6-like gene has been modified as disclosed elsewhere herein. In a preferred embodiment, the polynucleotide comprises, preferably consists of, modifications of SEQ ID NO: 1. An example of a modified ssn6-like gene is depicted in FIG. 1G (SEQ ID NO: 7). Thus, in a further preferred embodiment, the polynucleotide according to the present invention comprises, preferably consists of, SEQ ID NO: 7.

As it is known to a person skilled in the art, it is possible to propagate and/or express a certain nucleotide sequence by inserting this sequence into a vector, which is then, in turn, introduced in a host cell such as a bacterium, with this bacterium preferably being *Escherichia coli* (*E. coli*) or a eukaryotic cell for instance as disclosed elsewhere herein, Thus, the present invention also refers to a vector comprising the polynucleotide sequence comprising the modified ssn6-like related/ssn6-like gene, as well as to a host cell comprising said vector or parts of said vector.

Depending on the respective intended use, said vector contains specific structural elements. If it is for instance intended to propagate the nucleotide sequence, then the corresponding vector has to contain an ori.

The present invention also refers to a polypeptide encoded by the polynucleotide sequence according to the present invention. If the polynucleotide sequence according to the present invention, comprising a modified ssn6-like related/ssn6-like gene as disclosed above, is expressed in a suitable expression system, the expression of a gene product, e.g. of a polypeptide or protein, depends on the modifications that have been carried out. For instance, if the modification results in a shift of the complete reading frame, in all likelihood no gene product can be expressed. It can however also be that the modification only results in a truncated ("shortened") nucleotide sequence, which in turn results in the expression of a truncated gene product which may also contain a short heterolgous amino acid sequence at its C-terminus which is coded by the inserted heterologous nucleotide sequence (see FIG. 2B, SEQ ID NO: 9, with 7 heterologous C-terminal amino acids (EWYLQLR, underlined in FIG. 2B; SEQ ID NO: 139), as compared to the non-mutated sequence in FIG. 2A, SEQ ID NO: 8).

In the present invention it has been surprisingly found that by partially or completely inhibiting the wildtype function and/or activity of SSN6-like related/SSN6-like protein, or by effecting that SSN6-like related/SSN6-like protein is essentially not present, respectively in a cell that in its wildtype form comprises a gene encoding said protein, a gene being under the control of a promoter that is repressed in the presence of SSN6-like related/SSN6-like protein can be overexpressed in a suitable expression system.

Thus, the present invention further refers to an expression vector comprising a promoter, wherein said promoter is characterized in that it is repressed in the presence of SSN6-like protein or SSN6-like related protein if said expression vector is introduced into a suitable expression system, e.g. into a eukaryotic cell as defined elsewhere herein. By using this expression vector, a gene under control of a promoter that is repressed in the presence of SSN6-like related/SSN6-like protein can be overexpressed in a suitable expression system. In order to determine whether a promoter is repressible by SSN6-like related/SSN6-like protein, any suitable method that is known to a person skilled in the art can be used. For instance, expression vectors can be designed that comprise the promoter to be tested, and an indicator gene (also called reporter-gene) such as luciferase that is under control of the promoter to be tested. If, in the presence of SSN6-like related/SSN6-like protein, the espression of the gene product is reduced, then the candidate promoter is repressed in the presence of SSN6-like related/SSN6-like. Determination of the reduced candidate promoter activity for example can be measured by quantifying the indicator gene product or its activity, for example luciferase, by methods known in the art. There are a number of assays know in the art, which can be used to determine promoter-activity or mesure interaction of proteins with promoter-sequences and which thereby are suitable to test wether the activity of a certain promoter is influenced by an SSN6-like or SSN6-like related protein. Examples of such assays are reporter gene assays, electrophoretic mobility shift assays (EMSA, gel shift assays), double-stranded DNA pull-down assay, chromatin immune-precipitation assays, and DNase footprinting assays, etc.

In a preferred embodiment of the present invention, the expression vector comprises one or more gene(s) of interest that are under control of said promoter, i.e. the promoter that is repressed in the presence of SSN6-like related/SSN6-like protein. By applying suitable protocols that are known to a skilled person, such as a protocol as disclosed above, a person skilled in the art is able to assess whether a promoter is repressed in the presence of SSN6-like related/SSN6-like protein, or not. In a preferred embodiment of the present invention, the promoter being comprised in the expression vector and contolling the gene(s) of interest is an LLP promter or a modified version thereof. Preferably, the LLP promoter comprises, preferably consists of, the polynucleotide sequence depicted in SEQ ID NO: 2 or 12. The term "modified version" of the LLP promoter defines that said modified LLP promoter still exhibits the function of an LLP promoter in terms of regulating the expression of the gene that is under its control.

It is further possible that the promoter is an LLP promoter, and that LLP is encoded or is not encoded by the polynucleotide sequence of the expression vector. In either case, and also in case the promoter is not LLP promoter but a different promoter that is repressed in the presence of SSN6-like related/SSN6-like protein, the gene of interest preferably is selected from the group consisting of genes encoding enzymes, antibodies or fragments thereof, hormones, structural proteins, and protein-antigens being present in vaccines.

Preferably, the expression vector further comprises features selected from any one of the following:
(i) a selection marker;
(ii) a purification marker;
(iii) a signal sequence, preferably an alpha-factor secreting signal sequence, more preferably the MFalpha pre-pro signal sequence, even more preferably a signal sequence comprising or consisting of, preferably consisting of, SEQ ID NO: 14 or SEQ ID NO: 21;
(iv) an origin of replication; and/or
(v) a nucleotide sequence for targeted and/or random integration into the genome of a host cell.

The expression vector can be comprised in a host cell as described herein, preferably in a bacterium such as E. coli, for instance for propagation purposes.

The expression vector can also be introduced into the modified eukaryotic cell according to the present invention, resulting in the introduction of the expression vector's expression cassette into the modified eukaryotic cell's genome. The introduction of the expression vector into the host cell can be carried out according to any suitable method that is known to a skilled person, for instance by electroporation. In addition, transient expression, i.e. the expression vector is not integrated into the genome, can also be considered.

The present invention also refers to a modified eukaryotic cell comprising the expression vector as defined herein.

The introduction of the expression cassette of the expression vector into the modified eukaryotic cell is also denoted as "recombination" and can be a targeted, i.e. homologous, recombination, or a random recombination. If a random recombination takes place, the expression cassette integrates in such a way into the genome of the modified eukaryotic cell that the nucleotide sequence encoding LLP protein present in the modified eukaryotic cell is not affected. In other words, the modified eukaryotic cell expresses not only the gene of interest, but also the LLP protein. In this case, the amount of LLP protein being present in the modified cell, the supernatant of the modified cell or in subfractions thereof can be used as an indicator of the purity of the expression product of the gene of interest, i.e. the protein of interest, for example during purification of the protein of interest. This situation, where the LLP protein is expressed in addition to the gene(s) of interest, is referred to as "Option 2" (FIG. 3D).

Thus, the present invention also refers to a eukaryotic cell comprising
a modified ssn6-like related gene or a modified ssn6-like gene, wherein said gene has inserted a foreign nucleotide sequence, to the effect that
(i) the eukaryotic cell is not able to provide an SSN6-like related protein or an SSN6-like protein that exerts its wildtype function and/or wildtype activity, preferably with respect to its activity and/or function in regulating the LLP promoter,
(ii) the amount of SSN6-like related protein or of SSN6-like protein being present in the eukaryotic cell differs from the amount of SSN6-like related protein or of SSN6-like protein being present in its wildtype form, preferably the amount of the SSN6-like related protein or of the SSN6-like protein is reduced, and/or
(iii) no SSN6-like related protein or SSN6-like protein is present in the eukaryotic cell,
a gene of interest under control of the LLP promoter, and an llp gene,
preferably wherein said eukaryotic cell exhibits reduced SSN6-like related protein or SSN6-like protein activity and/or function, or no SSN6-like related protein or SSN6-like protein activity and/or function at all.

If a targeted, i.e. homologous, recombination takes place, and if additionally the promoter of the expression cassette is an LLP promoter or a modification thereof, then the expression cassette is inserted in such a way that it replaces (partially or completely) the nucleotide sequence of the gene encoding the LLP protein. In this case, there is no expression of LLP. This situation, where only the gene(s) of interest, but no LLP protein, is expressed, is referred to as "Opition 1".

Thus, the present invention also refers to a eukaryotic cell comprising
- a modified ssn6-like related gene or a modified ssn6-like gene, wherein said gene has inserted a foreign nucleotide sequence, to the effect that
  (i) the eukaryotic cell is not able to provide an SSN6-like related protein or an SSN6-like protein that exerts its wildtype function and/or wildtype activity, preferably with respect to its activity and/or function in regulating the LLP promoter,
  (ii) the amount of SSN6-like related protein or of SSN6-like protein being present in the eukaryotic cell differs from the amount of SSN6-like related protein or of SSN6-like protein being present in its wildtype form, preferably the amount of the SSN6-like related protein or of the SSN6-like protein is reduced, and/or
  (iii) no SSN6-like related protein or SSN6-like protein is present in the eukaryotic cell,
and
- a gene of interest that replaces a part or all of the coding region of the gene encoding the LLP protein, to the effect that essentially no LLP protein is present in the eukaryotic cell, and that is under control of the LLP promoter,
preferably wherein said eukaryotic cell exhibits reduced SSN6-like related protein or SSN6-like protein activity and/or function, or no SSN6-like related protein or SSN6-like-protein activity and/or function at all.

The present invention further refers to an expression system, comprising
  a) the modified eukaryotic cell as defined herein;
  b) the expression vector as defined herein, wherein said expression vector can also be present in linearized form and/or at least parts of the vector being integrated into the genome of the modified eukaryotic cell.

In a further preferred embodiment of the present invention, the modified eukaryotic cell additionally comprises a promoter, wherein said promoter is repressed in the presence of SSN6 protein or SSN6-like protein. Preferably, said promoter is an LLP promoter, preferably an LLP promoter comprising, preferably consisting of, SEQ ID NO: 2 or 12, or modified versions thereof, said modified versions being characterized in that they still exhibit essentially the same promoter function as a wildtype LLP promoter.

In a further embodiment, the modified eukaryotic cell additionally comprises (a) gene(s) of interest, preferably selected from the group consisting of genes encoding enzymes, antibodies or fragments thereof, hormones, structural proteins, and protein-antigens being present in vaccines, wherein said gene(s) of interest is (are) under control of a promoter being repressed in the presence of SSN6-like protein or SSN6-like related protein. Preferably, this promoter is an LLP promoter, preferably an LLP promoter comprising, preferably consisting of, SEQ ID NO: 2 or 12, or modified versions thereof, said modified versions being characterized in that they still exhibit essentially the same promoter function as a wildtype promoter.

As already explained above, it is possible that in said expression system the LLP gene is not expressed in addition to the gene(s) of interest (option 1), and it is also possible that the LLP gene is expressed in addition to the gene(s) of interest (option 2). In the first case (option 1), the LLP promoter only controls the expression of (a) gene(s) of interest, and in the latter case (option 2), the LLP promoter controls the expression of (a) gene(s) of interest (which are different from genes encoding LLP), and LLP.

The present invention further refers to the use of the modified eukaryotic cell, the modified polynucleotide sequence, the expression vector, the host cell, or an expression system as defined herein in a method of expressing, preferably overexpressing, gene(s) of interest.

As disclosed above, the amount of LLP protein being present in a composition comprising the protein of interest is an indicator of the purity of said composition regarding said protein of interest. Thus, the present invention also refers to a method for determining the purity of a composition comprising the expression product of a gene of interest, comprising the following steps:
  (a) expressing gene(s) of interest by using the modified eukaryotic cell and the expression vector, respectively according to the present invention, wherein
    (a1) the modified eukaryotic cell comprises a gene encoding LLP protein under control of an LLP promoter, and wherein
    (a2) the expression vector comprises one or more gene(s) of interest under control of an LLP promoter or a modified LLP promoter, wherein said gene of interest does not encode LLP,
  thereby obtaining a composition comprising the expression product of the gene(s) of interest, i.e. the protein(s) of interest, and the LLP protein;
  (b) determining the amount of the expression product of the gene(s) of interest, i.e. the amount of the protein(s) of interest, and the amount of LLP protein being present in the composition obtained in step (a), wherein the amount of LLP protein compared to the amount of expression product of the gene(s) of interest, i.e. of the protein(s) of interst, is indicative for the purity of the composition obtained in step (a); and, optionally,
  (c) subjecting the composition of step (a) to one or more downstream purification step(s), followed by step b), i.e. determining the amount of the expression product of the gene(s) of interest, i.e. the protein(s) of interest, and the amount of LLP protein being present in the composition obtained after having carried out said downstream purification step.

In order to obtain a composition that comprises LLP, in addition to the gene(s) of interest, the integration of the expression cassette of the expression vector represents a random integration into the genome of the modified eukaryotic cell.

The composition comprising the protein(s) of interest and the LLP protein can be any composition that arises in the course of the process of producing the protein(s) of interest. Accordingly, such a composition can for instance be a supernatant of the cell culture used in expressing the protein (s) of interest The present invention further refers to a method of expressing one or more gene(s) of interest in a eukaryotic cell comprising an ssn6-like related gene or an ssn6-like gene, wherein the translation of the mRNA transcript of the ssn6-like related gene or the ssn6-like gene is prevented by hybridizing a complementary sequence or a partial sequence thereof to the mRNA transcript. In a preferred embodiment, the partial sequence of the complementary sequence is a siRNA, anti-sense RNA, a ribozyme, or triplex RNA or DNA.

In a further embodiment, the present invention refers to a method of expressing one or more gene(s) of interest in a eukaryotic cell comprising an SSN6-like expression cassette or SSN6-like related expression cassette, wherein the SSN6-like protein or the SSN6-like related protein in said eukaryotic cell is modified or inhibited in its function and/or activity. Preferably, the SSN6-like protein or SSN6-like related protein of said eukaryotic cell is modified or inhibited in its function and/or activity in regulating the LLP promoter, more preferably the SSN6-like protein or SSN6-like related protein exhibits reduced SSN6-like related protein or SSN6-like protein activity and/or function, or no SSN6-like related protein or SSN6-like protein activity and/or function.

DESCRIPTION OF THE FIGURES

FIG. 1: Polynucleotide Sequences

FIG. 1 shows various polynucleotide sequences.

FIG. 1A shows the nucleotide sequence of the coding region of the ssn6-likegene of *P. Pastoris* (SEQ ID. NO: 1).

FIG. 1B shows the nucleotide sequence of the LLP promoter of *P. pastoris*, 605 bp 3' from the ATG start codon of LLP (SEQ ID NO: 2).

FIG. 1C shows the nucleotide sequence of the signal sequence of the LLP protein of *P. Pastoris* (SEQ ID NO: 3).

FIG. 1D shows the nucleotide sequence of the terminator sequence of llp gene of *P. Pastoris* (SEQ ID NO: 4).

FIG. 1E shows the nucleotide sequence of the SSN6-like promoter of *P. Pastoris*, 1000 bp 3' from the ATG start codon of SSN6-like (SEQ ID NO: 5).

FIG. 1F shows the nucleotide sequence of the terminator sequence of ssn6-like gene of *P. Pastoris* (SEQ ID NO: 6).

FIG. 1G shows the nucleotide sequence of the SSN6-like modified DNA of *P. Pastoris* (from the ATG start to the TAA stop codon) as present in *P. Pastoris* strain SSS1. This results in a ssn6-like coding region with an internal insertation of a heterologous nucleotide sequence, which disrupts the coding sequence of ssn6-like coding sequence (SEQ ID NO: 7).

FIG. 1H shows the nucleotide sequence of the Kozak start sequence (SEQ ID NO: 11).

FIG. 1I shows the nucleotide sequence of the LLP promoter, 1000 bp 3' from the ATG start codon of LLP (SEQ ID NO: 12).

FIG. 1J shows the amino acid sequence of the SSN6-like protein (SEQ ID NO: 13)

FIG. 1K shows MFalpha pre-pro signal sequence: FIG. 1K(A) shows said signal sequence without EAEA repeat (SEQ ID NO: 14), and FIG. 1K(B) shows said signal sequence with EAEA repeat (SEQ ID NO: 21).

FIG. 1L shows the codon optimized DNA sequence of encoding a single chain antibody fragment DLX521 (SEQ ID NO: 15).

FIG. 1M shows the coding region of the DNA sequence of the llp-gene including the signal sequence (SEQ ID NO: 16).

FIG. 1N shows the codon optimized nucleotide sequence of the human Growth Hormone (hGH) as used in the examples of this application (SEQ ID NO: 17)

FIG. 1O shows the nucleotide sequence of the human serum albumin (HSA) as used in the examples of this application (SEQ ID NO: 18).

FIG. 1P shows the nucleotide sequence of the penicillin V amidase (PVA) as used in the examples of this application (SEQ ID NO: 19).

FIG. 1Q shows the nucleotide sequence of the vector pGAPk used for generating the SSS1 yeast cell line (plasmid without a GOI and with a Geneticin resistance marker) (SEQ ID NO: 20)

FIG. 1R shows the sequence of a pLLP vector containing a Geneticin resistance marker (pLLPk) corresponding to SEQ ID NO: 22.

FIG. 1S shows SEQ ID NO: 23, which is part of the nuceleotide sequence of chromosome 1 of the genomic sequence of yeast strain YJK_PVA_021 after random integration of a PVA- and a Zeocin-expression cassette into the coding region of ssn6-like (reverse-complement sequence of ssn6-like) at position 807,480 of chromosome 1 of the reference strain *Pichia pastoris* CBS 7435. The ssn6-likesequenceisunderlined, the start codon is shown in bold and double-underlined (ATG→reverse-complement→CAT). Shown is the interrupted ssn6-like coding sequence including 10 nucleotides flanking 5' and 3' to the ssn6-like coding sequence. The sequence shown is part of the Illumina-sequenced genome of strain YJK_PVA_021 (SEQ ID NOs: 67-115) and the sequence of SEQ ID NO: 23 is part of the genomic sequence SEQ ID NO: 103 obtained by Illumina Inc. Sequences of oligo2395 (reverse-complement sequence of oligo2395) and oligo2398 are labeled in grey.

FIG. 1T shows the LLP signal sequence fused to the 3' end of HSA coding sequence replacing the native HSA-signal sequence resulting in the sequence according to SEQ ID NO: 121.

FIG. 1U shows SEQ ID NO: 129, which is the shortened LLP-promoter sequence delta29 corresponding to a 576 bases length of the shortened LLP-promoter.

FIG. 1V shows SEQ ID NO: 130, which is the shortened LLP-promoter sequence delta93 corresponding to a 512 bases length of the shortened LLP-promoter.

FIG. 1W shows SEQ ID NO: 131, which is the shortened LLP-promoter sequence delta133 corresponding to a 472 bases length of the shortened LLP-promoter.

FIG. 1X shows SEQ ID NO: 132, which is the shortened LLP-promoter sequence delta201 corresponding to a 404 bases length of the shortened LLP-promoter.

FIG. 1Y shows SEQ ID NO: 133, which is the shortened LLP-promoter sequence delta233 corresponding to a 372 bases length of the shortened LLP-promoter.

FIG. 1Z shows SEQ ID NO: 134, which is the shortened LLP-promoter sequence delta300 corresponding to a 305 bases length of the shortened LLP-promoter.

FIG. 2: Amino Acid Sequences

FIG. 2 shows various amino acid sequences.

FIG. 2A shows the amino acid sequence of the SSN6-like protein of *P. Pastoris* (SEQ ID NO: 8)

FIG. 2B shows the amino acid sequence of the SSN6-like modified protein of *P. Pastoris* YJK_PVA_021 (SEQ ID NO: 9). The underlined 7 amino acids represent heterologous, non-SSN6-like amino acids originationg from the vector used to inactivate the SSN6-like protein.

FIG. 2C shows the amino acid sequence of the LLP protein including LLP signal sequence (SEQ ID NO: 10).

FIG. 2D shows the amino acid sequence of the LLP signal sequence of *p. pastoris* (SEQ ID NO: 140).

FIG. 3: Mechanism of Super-Secretor *Pichia Pastoris* (SSS1)

wt=wild-type, ssn6-like=ssn6-like gene, LLP=LLP coding sequence, Pl=LLP-promoter, LLP-prot.=LLP-protein, Pg=GAP-promoter, AR=antibiotic resistance, GOI=coding sequence of gene of interest, GOI-prot.=gene of interest protein

FIG. 3A

The wt-strain (wild-type strain, NRRL Y-11430) contains an intact ssn6-like gene which according to our interpretation suppresses the promoter (Pl) of the lectine like protein (LLP). The ssn6-like gene is on the reverse strand of chromosome 1 (coding sequence is from 806379-808244)

and the LLP gene is on the forward strand of chromosome 1 (coding sequence is from 2492530 to 2493945).

FIG. 3B

An expression construct with a radomly integrated Pg/AR sequence into the coding sequence of ssn6-like gene of strain NRRL Y-11430 was obtained. The resulting strain contains a disrupted ssn6-like gene (inact. ssn6-like). According to our interpretation, disruption of the ssn6-like resulting in inact. ssn6-like removes the suppressing effect of ssn6-like on the Pl-promoter, threby activating of the Pl-promoter finally resulting in high expression of LLP-protein or of other GOIs (Gene Of Interest) under control of a LLP-promoter.

FIG. 3C

A gene of interest (GOI) can be introduced into the yeast strain of Fig. B by either homologous recombination thereby replacing the coding region of the LLP-gene by the coding sequence of the GOI (FIG. 3C,=Option 1), and resulting in expression of the GOI (GOI-protein), whereas no LLP-protein is produced.

FIG. 3D

Alternatively a gene of interest (GOI) fused to the LLP-promoter (Pl, GOI) can be introduced into the yeast strain of Fig. B by random recombination leaving the LLP intact and inserting the GOI under control of the LLP-promoter (Pl) into a random position of the yeast genome. This results in concomit expression of the GOI (GOI-prot.) and of LLP (LLP-prot.).

Figure 4:
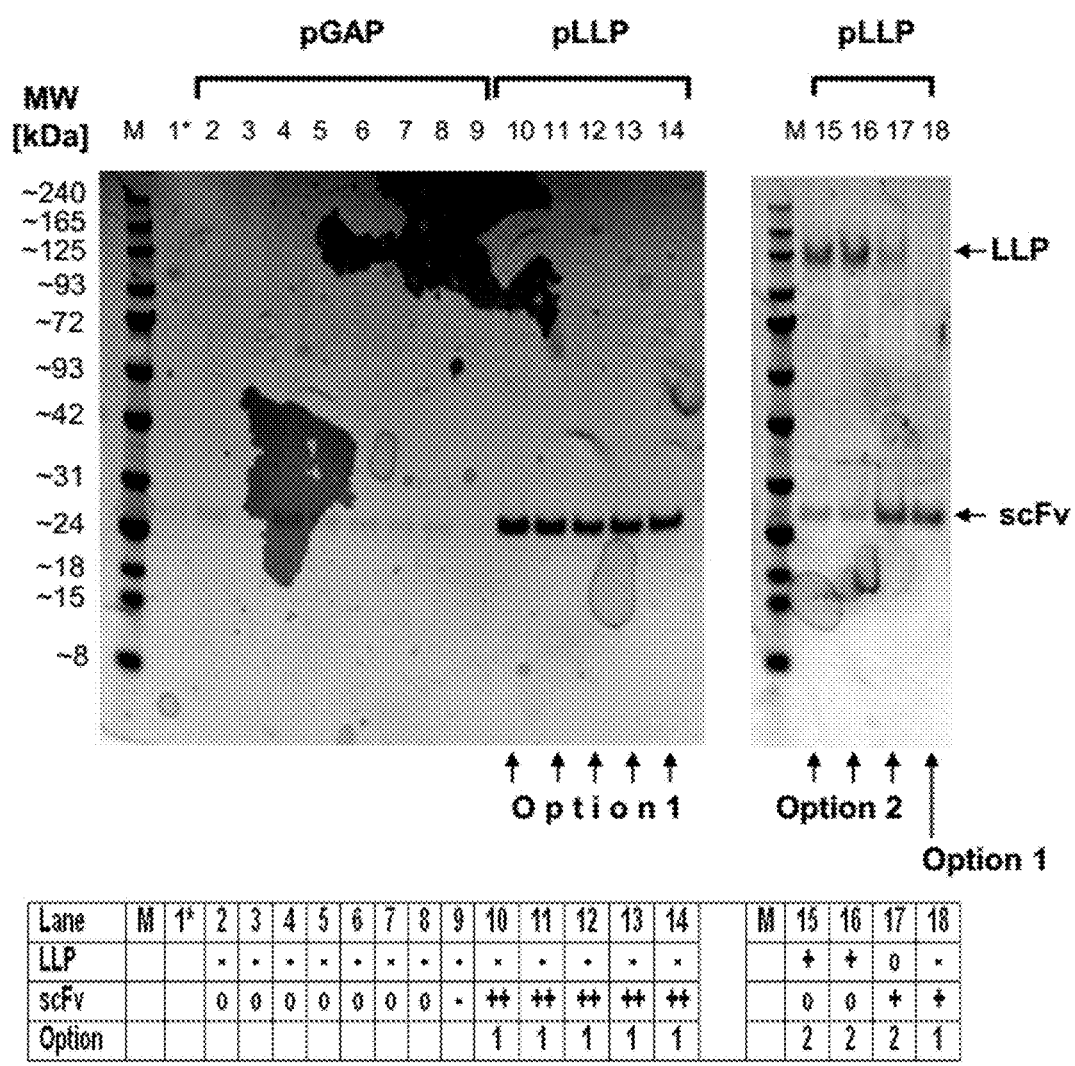

FIG. 4: SDS-PAGE Analysis

A codon optimized (done by DNA2.0 Inc., Menelo Park, USA) DNA sequence encoding the model protein DLX521 (an scFv=single chain variable Fragment of an antibody) was inserted into a plasmid with the GAP-promoter (pGAP=pJ905 from DNA2.0 Inc.) between restriction sites EcoRl and Notl, and a plasmid with the LLP-promoter (pLLP) between restriction sites EcoRV and Notl. The pGAP plasmid was linearized with Swal and transformed in NRRL Y-11430 and the pLLP plasmid was linearized with Avrll and transformed in SSS1. For the pGAP plasmid, transformants were PCR screened and 8 clones with a positive PCR signal were randomly picked and used for glycerol stock preparation. For the pLLP plasmid, transformants were PCR screened and 9 clones with a positive PCR signal were randomly picked and used for glycerol stock preparation. The glycerol stocks of the 8 pGAP and 9 pLLP strains were subjected to expression studies at microtiter plate scale (25° C., 350 rpm, 70 h). The OD (optical density) at 600 nm was comparable at harvest (OD was determined at harvest to check for biomass variability). Subsequently, 15 µL of the samples (supernatant mixed with NuPAGE® LDS sample buffer incl. 2-mercaptoethanol according to manufacturers (Invitrogen/Life Technologies) instructions) were loaded onto the gel.

The SDS-polyacrylamide gel (SDS-PAGE) system used was the Novex NuPAGE® Bis-Tris 4-12% grandient gel (Invitrogen/Life Technologies) using the MES-buffer system (Invitrogen/Life Technologieis), The protein molecular weight marker (M) used was from AppliChem GmbH, Darmstadt, Germany. The used Protein Marker VI, prestained (AppliChem), shows the indicated approximate molecular weights in kilo Dalton (kDa) of the marker proteins if separated in a 10% SDS polyacrylamide gel (SDS-PAGE) using Bis-Tris 10% MES buffer according the manufacturer AppliChem. Loading volume was 15 µl yeast culture supernatand/lane. All pGAP- and pLLP-strains were pre-tested by PCR for scFv. Only scFv-positive strains were subsequently tested for expression of scFv protein. The table below the SDS PAGE gel lists the protein bands at the molecular weight positions of LLP and scFV, the intensity of the protein band (++ strong band, + clear band, o faint band, – no band) as well as the Option according to FIG. 1 to which this yeast clone belongs (Option 1: only GOI is expressed, no LLP; Option 2: GOI and LLP are expressed)

M: Protein Marker VI prestained (AppliChem)

Lane 1 scFv control strain that did not grow very well in deep well plates

Lanes 2-9: strain YJK_PVA_021, expressing low amounts of PVA under control of the GAP-promoter (faint band of scFV protein can be seen in lanes 2-9)

Lanes 10-18: strain PP_ESBA521_010 expressing scFv protein under control of the LLP-promoter.

Lanes 10 to 14: strong protein band at the molecular weight of scFv (see←scFv) ("←" indicates the protein band corresponding to the scFv protein) no protein band at the molecular weight of LLP (see←LLP), example of Option 1 (only expresion of GOI)

Lanes 15 and 16: strong protein band at molecular weight of LLP (see←LLP) ("←" indicates the protein band corresponding to the LLP protein) and clear band of scFv at molecular weight of scFv (see←scFv), example of Option 2 (parallel expression of GOI and of LLP)

Lane 17: clear protein band at molecular weight of LLP (see←LLP) and strong protein band of scFv at molecular weight of scFv (see←scFv), example of Option 2

Lane 18: no protein band at molecular weight of LLP (see←LLP) and strong protein band of scFv at molecular weight of scFv (see←scFv), example of Option 1

The high molecular weight protein band in the gel at the position of about the molecular weight marker 125 kDa represents a dimer of the LLP-protein. The identity of the LLP-protein was proven by the following experiments and evidences. First the LLP-band was cut out of the gel and the C-terminal amino acid sequence was determined by peptide sequencing using standard methods know in the art. Furthermore the LLP-gel band was analyzed by mass spectrometey using standard methods known in the art. Both methods proved that this protein band in the gel indeed is LLP-protein. Furthermore LLP was treted with an enzyme removing glyco-strctures from proteins, namely PNGase F. Treatment of LLP with PNGase F lowered the molecular weight of the LLP-dimer from about 125 kDa to about 110 kDa. Furthermore it is known from the literatrue (IUBMB Live, 2009, 61:252-60), that lectins can form very stable multimers such as dimers. Therefore we conclude the high molecular LLP-protein band in our SDS-PAGE gels is a stable LLP-protein dimer.

Figure 5:
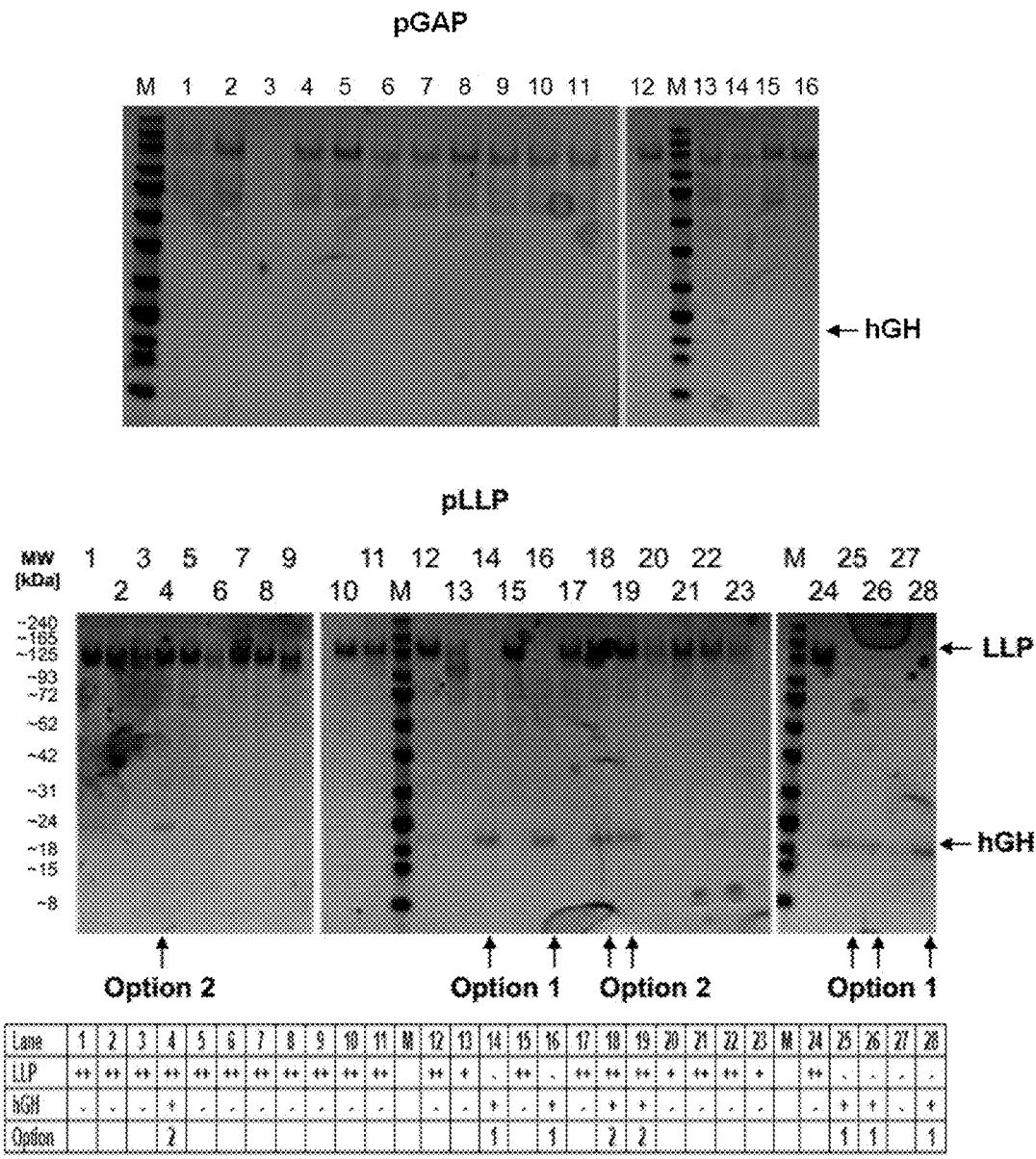
Figure 5:
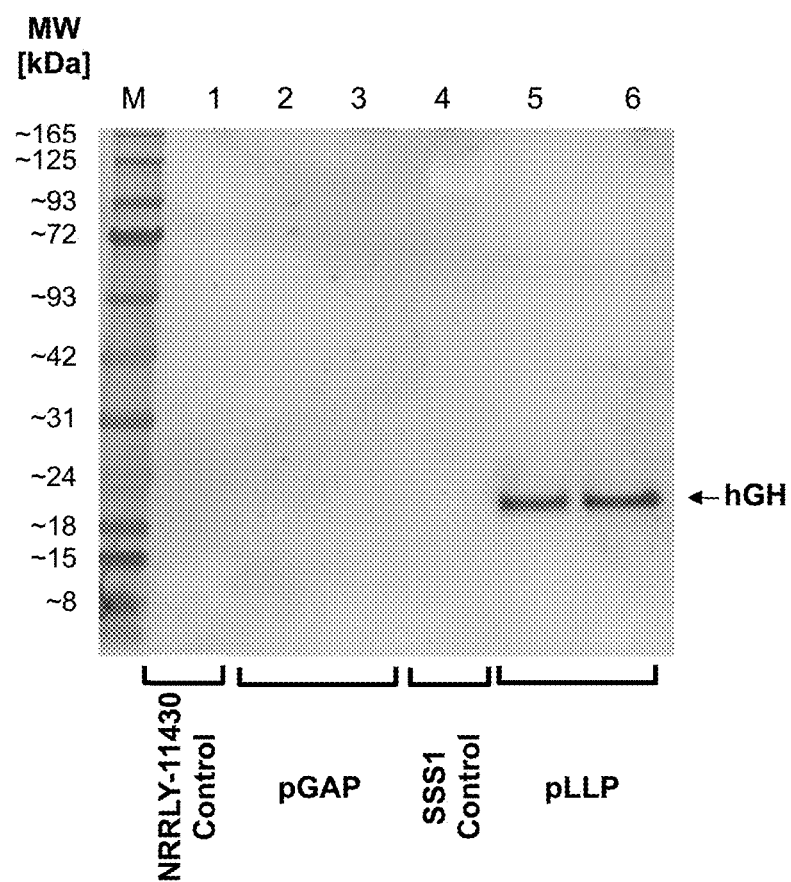

FIG. 5A: SDS PAGE Analysis

A codon optimized DNA sequence (SEQ ID NO: 17) encoding the model protein hGH was inserted into a plasmid with the GAP-promoter (pGAP) and one plasmid with the LLP-promoter (pLLP). The pGAP plasmid was transformed in NRRL Y-11430 and the pLLP plasmid in SSS1. For pGAP, 16 transformants were randomly picked and subjected to expression studies at microtiter plate scale (25° C., 350 rpm, 70 h). For pLLP, 28 transformants were randomly picked and subjected to expression studies at microtiter plate scale (25° C., 350 rpm, 70 h). The OD at 600 nm was comparable at harvest (OD was determined at harvest to check for biomass variability). Subsequently, 15 µL of the samples (supernatant mixed with NuPAGE® LDS sample buffer incl. 2-mercaptoethanol) were loaded onto the gel.

M: Protein Marker VI 10-245 from AppliChem.

pGAP: a protein band corresponding to hGH was detected by visual inspection of SDS-PAGE gels in 0/16 randomly picked clones (without prior PCR screening)

pLLP: a protein band corresponding to hGH was detected by visual inspection of SDS-PAGE gels in 8/28 randomly picked clones (without prior PCR screening)

This result indicates that the pLLP system is superior to the pGAP system.

FIG. 5B: hGH Western Blot 15, 20 or 30 µl supernatant samples of deep well plate cultures of *Pichia pastoris* cells transformed as described under FIG. 5A were directly loaded on SDS-PAGE gels (Novex NuPage 4-12% Bis-Tris Gels from Invitrogen with MES-running buffer). The proteins were then transferred to a PVDF membrane. After transfer and blocking, the membrane was incubated with a solution containing anti-hGH antibody (Zymed Cat.Nr. 18-0090, dilution: 1:1000) for 2 h. After washing the membrane, a secondary antibody coupled with alkaline phosphatase (anti-rabbit IgG alkaline-phosphatase conjugate, Sigma Cat. No. A3687, dilution: 1:16.000) was added for 1 h. After washing the membrane, NBT/BCIP (nitro-blue tetrazolium chloride/5-bromo-4-chloro-3-indolylphosphate toluidine salt) was added to detect hGH.

Figure 6:
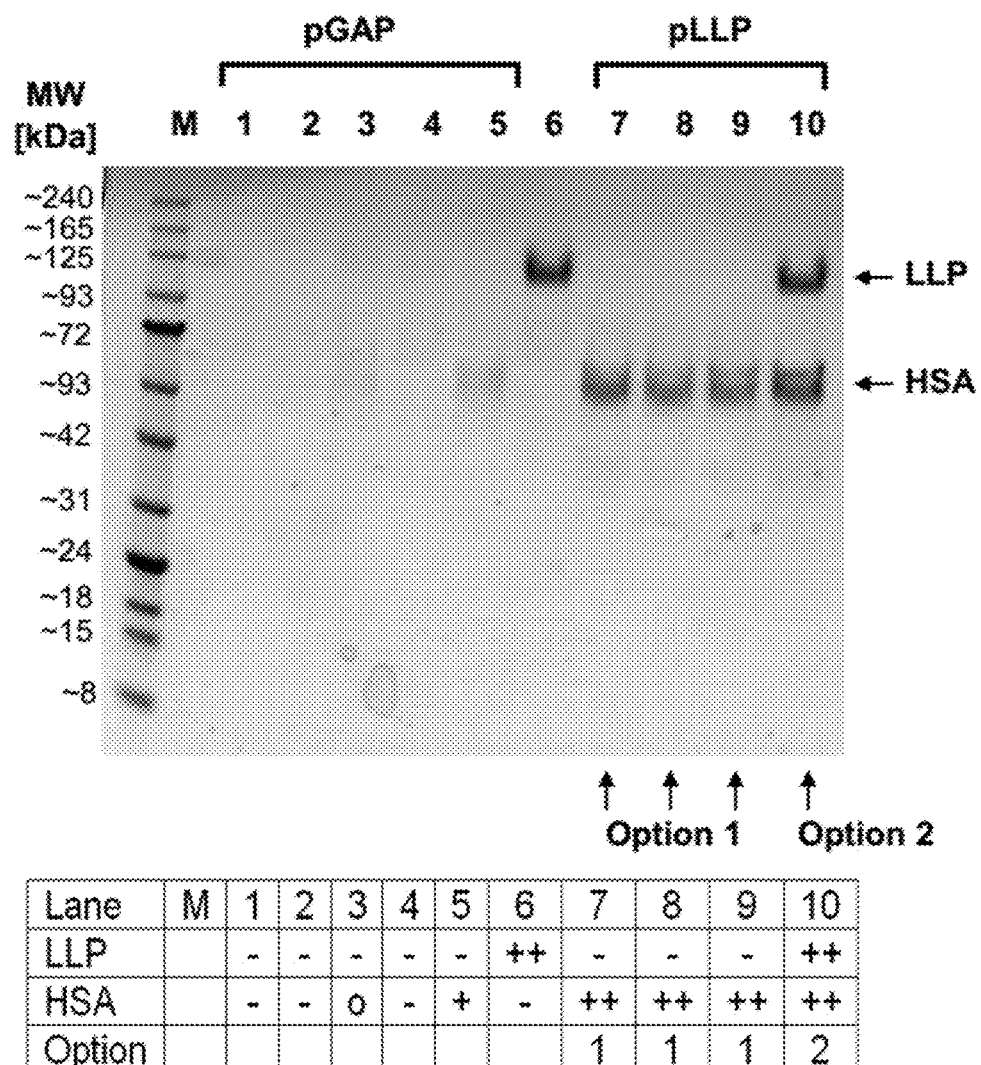

M: Protein Marker VI;
NRRL Y-11430 Control: wild type strain without hGH;
SSS1 Control: supersecretor strain without hGH;
pGAP: expression of hGH under control of GAP-promotor;
pLLP: expression of hGH under control of the LLP-promoter FIG. 6: SDS PAGE Analysis Lane 6 contains a sample of SSS1-cells not tranfected with a pLLP construct (negative control).

SDS-PAGE analysis. A codon optimized DNA sequence encoding the model protein HSA was inserted into on plasmid with the GAP-promoter (pGAP) and one plasmid with the LLP-promoter (pLLP). The pGAP plasmid was transformed in NRRL Y-11430 and the pLLP plasmid in SSS1. Colony PCR was applied to screen for transformants which were then subjected to expression studies at microtiter plate scale (25° C., 350 rpm, 70 h). The OD at 600 nm was comparable at harvest (OD was determined at harvest to check for biomass variability). Subsequently, 15 µL of the samples (supernatant mixed with NuPAGE® LDS sample buffer incl. 2-mercaptoethanol) were loaded onto the gel.

M: Protein Marker VI 10-245 from AppliChem.
pGAP: a faint protein band corresponding to HSA was detected by visual inspection of SDS-PAGE gels in 2/5 selected clones (lanes 3 and 5) (with prior PCR screening)
pLLP: a protein band corresponding to HSA was detected by visual inspection of SDS-PAGE gels in 4/4 selected clones (with prior PCR screening)

This result indicates that the pLLP system is superior to the pGAP system.

FIG. 7 Comparison of pGAP Expression System with pLLP Expression System

This result indicates that the pLLP system is superior to the pGAP system.

7A:

*Pichia pastoris* strains transformed with HSA either under control of the GAP promoter (pGAP =*P. pastoris* glyceraldehyde-3-phosphate dehydrogenase promotor) or under control of the LLP promoter (pLLP=*P. pastoris* Lectin Like Protein promotor) were cultured in a 5 liter fermenter for 144 h at 25° C., pH 6.0 and 30% oxygen, using glycerol in batch growth phase and using constant glucose feed in main growth stage. Culture supernatant was analyzed for HSA employing a Human Serum Albumin ELISA (Enzyme Linked Immuno Sorbent Assay) kit from Cygnus Technologies (Cat. Nr. F055) according to the manufacturer's instructions. Mixtures of transformed yeast strains (pGAP) and mixtures of transformed yeast strains (pLLP) were tested in order to account for expression differences in individual strains, e.g. to determine the average expression rate of pGAP- and of pLLP-strains.

7B:

PVA enzyme assay. A codon optimized DNA sequence encoding PVA (*Pleurotus ostreatus*-Penicillin V Amidase) was inserted into a plasmid with the GAP-promoter (pGAP) and into a plasmid with the LLP-promoter (pLLP). The pGAP plasmid was transformed in NRRL Y-11430 and the pLLP plasmid in SSS1 yeast cells. For each plasmid, 16 transformants were randomly picked and subjected to expression studies at microtiter plate scale (25° C., 350 rpm, 70 h). The PVA titer (g/kg phenoxy actetic acid) and OD at 600 nm were determined at harvest and used for normalization (g/kg phenoxy normalized). The diagram shows the mean value±SEM (standard error of the mean) of PVA activity as measured by PVA-mediated-conversion of phenoxymethylpenicillin into phenoxy acetic acid g/kg. The highest individual value in each group is labeled with an asterix (*). For expression purpose one would usually choose those strains which do express the highest amount of PVA-activity (labeled with * in the diagram). In this case the best strain expressing PVA under control of the pLLP expressed about 2.9-fold more PVA-activity as compared to the best pGAP strain (pGAP: n=13, max. value was 0.17 g/kg, pLLP: n=15, max. value was 0.49 g/kg), The pGAP vector from DNA2.0 Inc. and the pGAP vector from Sandoz are almost identical. All Vector elements such as promoters, terminators, resistance-marker, pUC ori, etc. are the same in both vectors. Only minor differences regarding the used restriction enzyme sites and short nucleotide sequences which connect some of these elements within the vectors and are slightly different between both vectors.

FIG. 8: Expression of Gene of Interest (GOI) in Fermentor Yeast Cultures

8A

A codon optimized DNA sequence encoding the enzyme PVA (Penicillin V Amidase) was inserted into a plasmid under the control of the GAP-promoter (pGAP). The pGAP plasmid was transformed in NRRL Y-11430 yeast cells (*Pichia pastoris*), and cells were grown in a fermentor under standard conditions using standard media and culturing conditions as know in the art. The pGAP vector integrated randomly into the SSN6-gene, thereby activating the LLP-promoter. The superantant of the fermentation culture was subsequently treated with the enzyme PNGase F (Peptide N-Glycosidase F; cleaves asparagine-linked high mannose as well as hybrid complex oligosaccharides from glycoproteins; New England Biolabs, Catalogue Number P0704S). Samples of the untreated cell culture supernatand (lane 1) and of PNGase F-treated cell culture supernatand (lane 2) were separated in SDS-PAGE. Lane 1 shows the glycosylated LLP-dimer as a very strong band at about 125 kDa, whereas the PVA-band is somewhat diffuse at around 72 kDa, probably because individual molecules of PVA are glycosylated to a different extend. Lane 3 shows at about 36 kDa the protein band of the added PNGase F, at about 110 kDa the very strong band of the deglycosylated LLP-dimer (←LLP de-glyc.) and at about 52 kDa a now very clear, distinct band representing declycosylated PVA (←PVA de-glyc.).

8B

A codon optimized DNA sequence encoding a single chain antibody fragment (scFv), in this case the scFv named DLX521, was inserted into a plasmid under control of the LLP-promoter (pLLP). The pLLP plasmid containing a Geneticin resistance was randomly transformed into YJK_PVA_021(the already PVA-transformed yeast cells of FIG. 8A), and cells were grown in a fermentor under standard conditions using standard media and culturing conditions as know in the art. Supernatant of the fermentation was diluted 20-fold and 15 µl were loaded onto SDS-PAGE in the presence of 2-mercaptoethanol. A very strong protein band at the molecular weight position of the scFv is visible in the gel in lane 1. In addition a minor band at the position of the LLP-dimer is seen at about 125 kDa and a strong protein band of PVA is seen at about 72 kDa. No PNGase was added so all proteins are glycosylated. 20-fold dilution of the cell culture supernatand was done in order to depict the very high expression rate of the scFv relative to the LLP. This yeast strain is an example of the "Option 2" as depicted in FIG. 3D, except that 2 GOI are expressed (PVA and DLX521). PVA is under control of the GAP promoter and randomly integrated by chance into the ssn6-like gene.

This is an example showing, that besides the LLP promoter also other promotors, such as the GAP promoter, can be used in conjuction with the expression system of the invention.

8C

This scheme shows the expression construct used in FIG. 8A. A codon optimized DNA sequence encoding the enzyme PVA under control of the GAP-promoter was inserted into a plasmid (pGAP), This pGAP plasmid was transformed in NRRL Y-11430 yeast cells (*Pichia pastoris*), and cells were grown in a fermentor under standard conditions using standard media and culturing. OD600 measurements were used to adjust cell densities. The pGAP vector integrated randomly into the ssn6 gene, thereby activating the LLP-promoter and resulting in an expression of LLP protein.

This expression construct is a proof-of-principle, again showing that interrupting the ssn6 gene results in an improved expression of the gene being under control of the LLP promoter, in this case in an improved expression of the LLP protein, in addition to the expression of the PVA protein.

FIG. 9:

A:

Partial aligment of 39 different protein sequences showing sequence homology to *P. pastoris* SSN6-like protein (CCA36593.1) (SEQ ID NO: 8)

B:

*P. pastoris* SSN6-like consensus sequence 1 (SEQ ID NO: 63)

C:

*P. pastoris* SSN6-like consensus sequence 2 (SEQ ID NO: 64)

Figure 10:
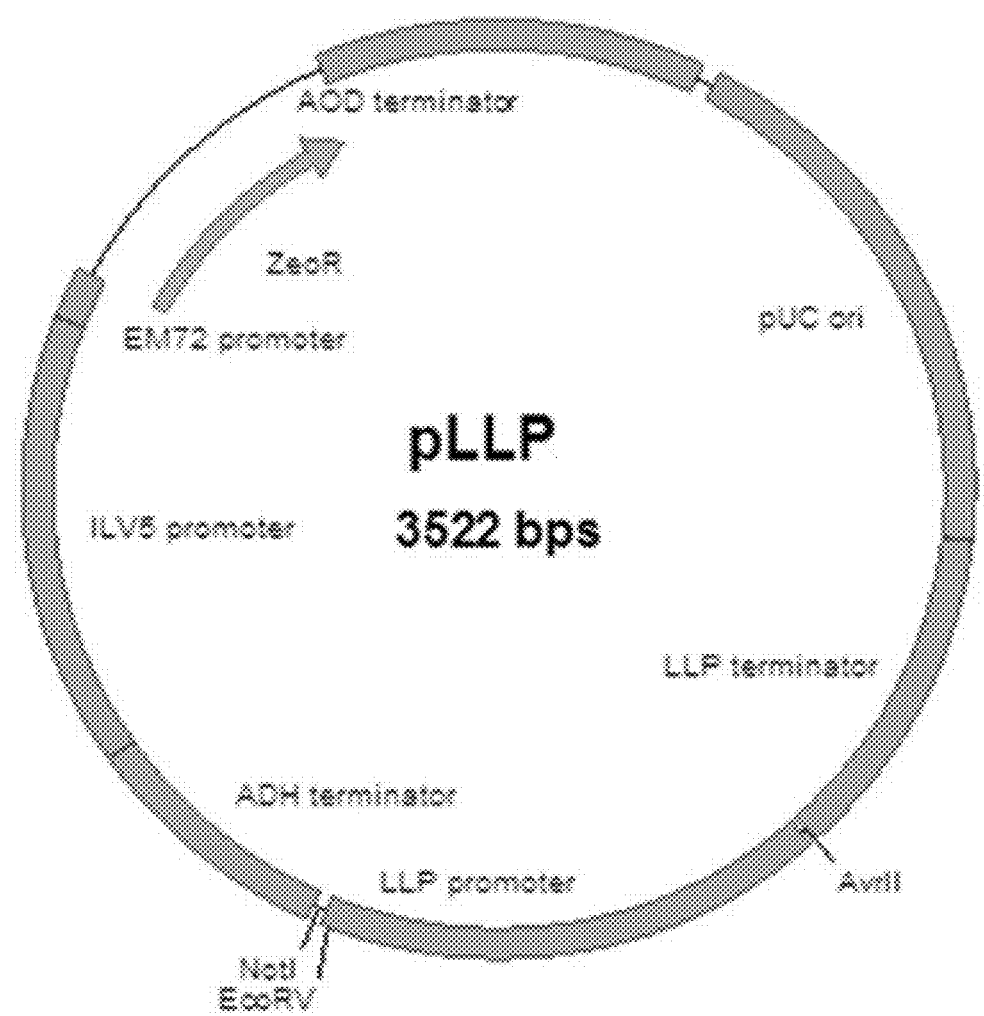

FIG. 10: Expression Vector pLLP

This figure shows the expression vector pLLP without inserted GOI (FIG. 10A), and its full length sequence (FIG. 10B) (SEQ ID NO: 65).

Expression vector (without inserted GOI): The gene of interest (GOI) can be inserted into this vector using the restriction endonuclease cleavage sites NotI and/or EcoRV, resulting in the GOI being under control of the LLP promoter and the ADH terminator. In order to insert the expression vector into the yeast genome, the vector can be linearized by cleaving with the restriction endonuclease AvrII, which restriction site is located between the LLP promoter and the LLP terminator sequence. The resulting linearized vector contains at its 5'-end the LLP promoter and at its 3'-end the LLP terminator. If inserted into the yeast genome by homologous recombination via the LLP promoter- and the LLP terminator-sequences, this homologous recombination removes the native LLP-coding sequence from the yeast genome. At the same time the GOI under control of the LLP promoter and the ADH terminator as well as a Zeocin expression cassette and all other parts of the pLLP vector are inserted into the yeast genome.

Figure 11:
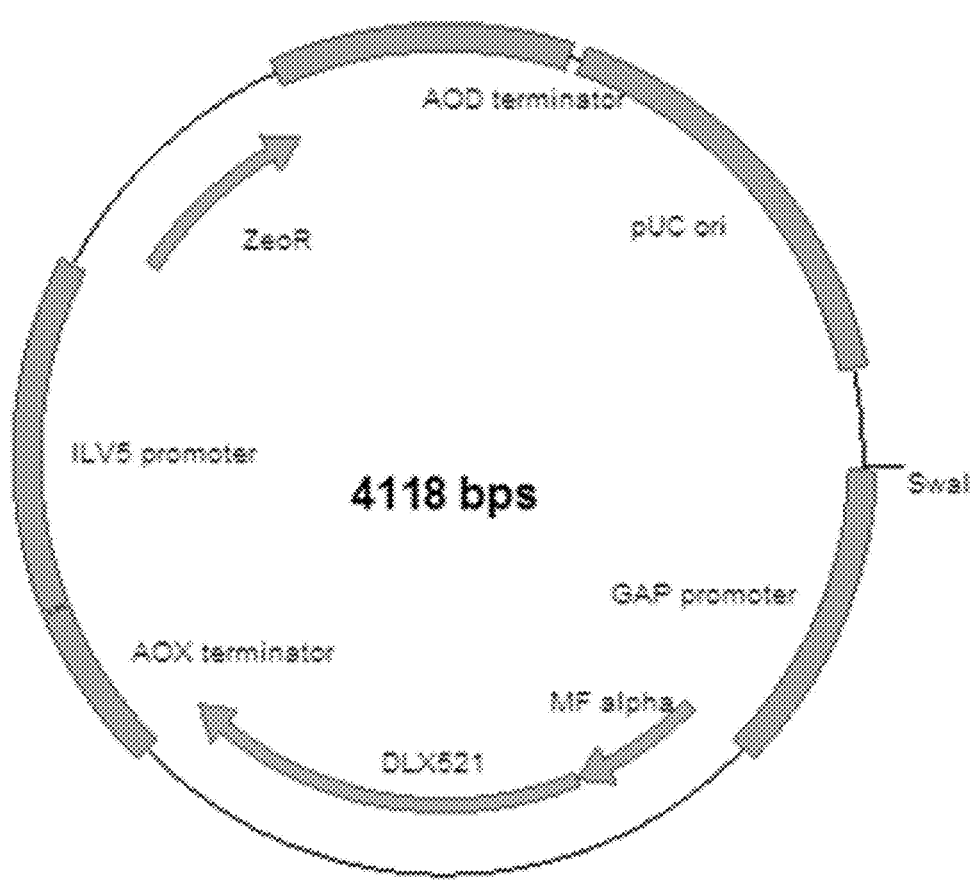

FIG. 11: Expression Vector pGAP with DLX521 as GOI

This figure shows the expression vector pGAP with DLX521 as GOI (FIG. 11A), and its full length sequence (FIG. 11B) (SEQ ID NO: 66).

Linearization of the vector has been carried out with SwaI.

FIG. 12: Expression of HSA Using LLP-Signal Sequence

This figure shows the expression of human serum albumin (HSA) utilizing the secreation signal sequence of LLP. The LLP-signal sequence was fused N-terminally to the coding sequence of HSA (llps-HSA), transformed into yeast cells. 10 randomly picked clones were grown in deep well plates and the supernatant checked for HSA expression (FIG. 12A). One clone was expressed also in a 1 liter fermenter for 48, 72 and 96 hours (FIG. 12B). Expression was shown by SDS-PAGE followed by Coomassie blue staining.

FIG. 13A-D: Analysis of the Functionality of LLP-Promoter Fragments (Truncation Analysis)

The LLP-promoter was successively shortened by cloning of PCR-generated LLP-promoter fragments into YJK_PVA_021 yeast strain. 11 randomly picked clones for each LLP-promoter length were picked and grown in deep well plates and the supernatant analyzed by SDS-PAGE followed by Coomassie blue staining. The lengths of the tested LLP-promoter fragments were as follows: Fig. A: 576 bp, Fig. B: 512 bp, Fig. C: 472 bp, and Fig. D: 372 bp. Each figure shows two representative lines, with "Option 1" denoting that only scFv is expressed, and with "Option 2" denoting that scFv and LLP is expressed.

FIG. 14: Sequences *S. Cerevisae* ssn6 and TUP1 (Complete Coding Region)

This figure shows the respective complete coding region of the following:
A. Ssn6 nucleic acid, of *S. cerevisiae* (SEQ ID NO: 135);
B: SSN6 Protein, of *S. cerevisiae* (SEQ ID NO: 137);
C: Tup-1 nucleic acid of *S. cerevisiae* (SEQ ID NO: 136);
D: Tup-1 protein of *S. cerevisiae* (SEQ ID NO: 138).

METHODS

1. Assessing the amount of a candidate ssn6-like related gene

The level of expression of a candidate ssn6-like related gene can be measured for example by measuring the level of mRNA of said ssn6-like related gene by northern blotting or by quantitative Polymerase Chain Reaction (qPCR) or reverse transcriptase qPCR, or measuring the activity of the promoter of said ssn6-like related gene for example by using luciferase reporter gene assays or by using ssn6-like related promoter-green fluorescent protein (GFP) constructs, etc. All these methods are well known to a person skilled in the art and represent routine work. A textbook comprising protocols for routine methods is for instance Sambrook et al., "Molecular Cloning: A Laboratory Manual", 4$^{th}$ Edition, Cold Spring Harbor Laboratory Press, (2012), referred to herein as Sambrook et al.

2. Assessing whether a candidate ssn6-like related gene resembles the ssn6-like gene as defined herein with respect to function, activity and sequence 2.1 Measuring the amount of LLP protein expressed in cell culture:

The amount of a protein (or its expression level) can be determined according to any suitable method that is known to a person skilled in the art, for instance by measuring the amount of LLP protein in the supernatant of a cell culture by ELISA, by western blotting, or SDS PAGE (sodium dodecyl sulfate polyacrylamide gel electrophoresis) analysis of LLP protein.

In the present invention, the amount of LLP protein in the supernatant has been measured by carrying out a qualitative SDS PAGE analysis (Novex NuPage 4-12% Bis-Tris Gels with MES running buffer, from Invitrogen).

Alternatively the level of LLP protein can be determined indirectly by measuring LLP-mRNA using the same methods as described above in paragraph 1 "Assessing the amount of a candidate ssn6-like related gene".

2.2 Measuring the Amount of a Gene of Interest (GOI) Expressed Under Control of the LLP-Promoter in Cell Culture The same methods for measuring the amount of LLP-protein, as described above under 2.1, can also be used for measuring GOI-protein expressed under control of a LLP-promoter according to the invention.

2.3 Measuring Activity and Function of a Protein

In order to measure the function and activity of SSN6-like protein or SSN6-like related protein, any suitable protocol that is known to a skilled person can be used. Especially any method suitable to measure the functioning of the LLP-promotor can be use to measure the function and activity of SSN6-like protein or SSN6-like related protein, such as the methods mentioned under 2.1 and 2.2 above.

Once an SSN6-like protein or a SSN6-like related protein has been identified, its LLP-promoter-suppressing activity can be inhibited by inactivating the corresponding ssn6-like gene or ssn6-like related gene by methods described elsewhere in this application. Once this blockage has been performed the functioning (meaning the reduced amount of, or the complete lack of) the corresponding SSN6-like protein or mRNA or SSN6-like related protein or mRNA can be measured. Suitable methods are described elsewhere in this application.

PVA enzyme assay: an aliquot of the supernatant was mixed with the substrate Phenoxymethylpenicillin-Kalium and incubated at 22° C. The presence of active PVA enzyme will result in cleavage of the substrate in a titer-dependent manner. The reaction was stopped after 60 min by addition of ice-cold methanol. The amount of the cleavage product phenoxy acetic acid was determined by quantitatve HPLC.

3. Comparison of Different Expression Systems

In order to compare the protein expression of different expression systems, any suitable method that is known to a person skilled in the art can be carried out. In the present invention, the following protocol has been applied for this purpose:

The supernatants obtained from the pLLP expression system and from the pGAP system (same volume) were directly loaded on SDS-PAGE gels for relative comparisons of the pLLP vs. pGAP system.

4. Identification of Regulatory DNA Sequences

There are various tools available to predict regulatory DNA sequences, reviewed for example by Wassermann et al., Nature Reviews Genetics 5, 276-287. There are also tools for the prediction the total length of a promotor sequence, as well as tools predicting distinct positions within such a promoter, which supposedly bind to certain transcription factors, etc. One of these online tools is available from the University of Copenhagen, Bioinformatics Center. We used the JASPAR development server, Version 5.0_ALPHA. Settings of this online tool were: JASPAR CORE fungi, all JASPAR matrix models were choosen (we searched for all transcription recognition sites listed for fungi in the JASPER CORE fungi database), profile score threshold was set to 95%. Our input sequence was the LLP-promoter sequence SEQ ID NO: 12. This anlaysis resulted in 63 predicted binding sites for transcription factors within the tested sequence as shown in the table below.

More details on transcripton factor binding site prediction can be found in Nat Rev Genet. 2004:4, 276-87.

| Model name | Score | Start | End | Strand | predicted site sequence |
|---|---|---|---|---|---|
| SKO1 | 14.890 | 274 | 281 | 1 | ACGTAATG |
| ABF1 | 13.893 | 204 | 219 | -1 | CCGTAAAAAGCGATAC (SEQ ID NO: 116) |
| CST6 | 13.595 | 271 | 279 | 1 | ATGACGTAA |
| SUM1 | 11.962 | 346 | 354 | 1 | ATAATTTTT |
| SPT23 | 11.708 | 750 | 757 | -1 | AAAATCAA |
| SPT23 | 11.708 | 516 | 523 | 1 | AAAATCAA |
| YOX1 | 11.696 | 638 | 645 | -1 | TTAATTAT |
| RFX1 | 11.668 | 39 | 46 | -1 | CGTTGCTA |
| STE12 | 11.624 | 917 | 923 | -1 | TGAAACG |
| YHP1 | 11.563 | 499 | 504 | 1 | TAATTG |
| AFT2 | 11.464 | 69 | 76 | -1 | CACACCCT |
| TEA1 | 11.362 | 265 | 272 | 1 | GCGGACAT |
| YML081W | 11.251 | 72 | 80 | -1 | ACCCCACAC |
| ARR1 | 11.154 | 684 | 691 | -1 | ATTTGAAT |
| TOS8 | 11.143 | 380 | 387 | 1 | GTGTCAAA |
| MBP1::SWI6 | 10.880 | 717 | 723 | 1 | TCGCGTT |
| PHD1 | 10.721 | 104 | 113 | -1 | ACCTGCATCA (SEQ ID NO: 117) |
| YPR022C | 10.671 | 73 | 79 | -1 | CCCCACA |
| YGR067C | 10.573 | 67 | 80 | -1 | ACCCCACACCCTAC (SEQ ID NO: 118) |
| ACE2 | 10.293 | 333 | 339 | 1 | CCCAGCA |
| ADR1 | 10.260 | 74 | 80 | -1 | ACCCCAC |
| MIG3 | 10.179 | 73 | 79 | -1 | CCCCACA |
| STB5 | 10.040 | 835 | 842 | -1 | CGGTATTA |
| MIG2 | 10.037 | 73 | 79 | -1 | CCCCACA |
| MIG1 | 9.822 | 74 | 80 | -1 | ACCCCAC |
| YAP5 | 9.428 | 704 | 709 | -1 | AAGCAT |
| YAP5 | 9.428 | 698 | 703 | 1 | AAGCAT |
| YAP5 | 9.428 | 456 | 461 | 1 | AAGCAT |

| Model name | Score | Start | End | Strand | predicted site sequence |
|---|---|---|---|---|---|
| SIG1 | 9.387 | 222 | 226 | -1 | ATATA |
| ARR1 | 9.314 | 106 | 113 | -1 | ACCTGCAT |
| MOT3 | 9.052 | 296 | 301 | 1 | AAGGTA |
| YAP5 | 8.787 | 259 | 264 | 1 | AAACAT |
| HAP2 | 8.684 | 424 | 428 | 1 | TTGGT |
| HAP2 | 8.684 | 159 | 163 | 1 | TTGGT |
| SKN7 | 8.580 | 401 | 406 | -1 | GGCCAT |
| HAP2 | 8.495 | 665 | 669 | -1 | TTGGC |
| HAP2 | 8.495 | 622 | 626 | 1 | TTGGC |
| HAP2 | 8.495 | 404 | 408 | -1 | TTGGC |
| PHO2 | 8.463 | 436 | 441 | -1 | ATAATA |
| GLN3 | 8.378 | 570 | 574 | 1 | GATAA |
| GLN3 | 8.378 | 6 | 10 | 1 | GATAA |
| MBP1 | 8.257 | 716 | 722 | -1 | ACGCGAT |
| PHO2 | 8.131 | 119 | 124 | 1 | ATATTA |
| PHO2 | 8.131 | 90 | 95 | -1 | ATATTA |
| SKN7 | 8.026 | 403 | 408 | 1 | GGCCAA |
| ARG80 | 7.974 | 956 | 961 | -1 | TGACAC |
| ARG80 | 7.974 | 380 | 385 | -1 | TGACAC |
| YAP5 | 7.933 | 185 | 190 | 1 | AGACAT |
| FZF1 | 7.932 | 551 | 556 | -1 | CTATCA |
| PHO2 | 7.806 | 488 | 493 | 1 | TTATTA |
| PHO2 | 7.806 | 435 | 440 | 1 | TTATTA |
| PHO2 | 7.733 | 638 | 643 | 1 | ATAATT |
| PHO2 | 7.733 | 346 | 351 | 1 | ATAATT |
| PHO2 | 7.733 | 51 | 56 | 1 | ATAATT |
| PHO2 | 7.408 | 640 | 645 | -1 | TTAATT |
| PHO2 | 7.402 | 587 | 592 | -1 | ATATTT |
| GLN3 | 7.272 | 552 | 556 | 1 | GATAG |
| GLN3 | 7.272 | 28 | 32 | -1 | GATAG |
| GLN3 | 7.272 | 2 | 6 | 1 | GATAG |
| HAP2 | 7.252 | 592 | 596 | -1 | TTGGA |
| HAP2 | 7.252 | 529 | 533 | 1 | TTGGA |
| HAP2 | 7.252 | 453 | 457 | -1 | TTGGA |
| HAP2 | 7.252 | 196 | 200 | -1 | TTGGA |

5. Transformation and Cultivation of Strains

Expression constructs were linearized by digestion with suitable restriction enzyme and transformed in Pichia strains by electroporation. The transformants were subseuqently plated on agar plates containing Zeocin (final concentration: 100 mg/L) and/or Geneticin (final concentration: 300 mg/L).

Single colonies or glycerol stocks were subjected to expression studies in 48-well plates using a starch/amylase based cell culture medium. OD (Optical Densitiy) at 600 nm at harvest was around 10, 6. Testing of Promoter Activity Promoter activity can be measured by any suitable method that is known to a person skilled in the art. An example of such a method is the use of qPCR or reporter gene assays (e.g. Luciferase, Green Fluorescent Protein (GFP) etc.), both of which are standard methods that are known to a person skilled in the art. For example the most suitable part of the LLP-promoter for high level expression of a GOI can be determined by successively shortened versions of the LLP-promoter sequence according to SEQ ID NO. 12, by inserting such shortened LLP-promoter sequences together with a Kozak sequence and a model protein sequence such as DLX521 (scFv), hGH, HSA, PVA, etc. and together with a signal sequence such as the MF-alpha pre-pro signal sequence with or without EAEA repeat, the natural signal sequence of said model protein, etc. into a pLLP vector carrying a resistance-marker such as Geneticin, Zeocin, etc. and transfecting such pLLP vetor into a suitable yeast cell such as for example YJK_PVA_021-cells, SSS1-cells, NRRL Y-11430-cells, etc. Individual clones or pooled clones of such transformed yeast cells then can be grown under standard growth conditions in deep well plated, shaker flasks, fermetors, etc. and the amount of expression of said model protein being measured using methods such as SDS-PAGE, ELISA, or protein-activity assays such as the PVA-assay described elsewhere in this application, etc. Shortened versions of the promoter could represent parts of the promoter sequence disclosed in SEQ ID NO: 12, for example a LLP-promoter having a length of 1000, 775, 675, 605, 576, 512, 472, 415, 404, 372, 305, 285, 235, 165, 100 nucleotides, etc. counted in each case from the 3'-end of SEQ ID NO: 12.

7. Assessing Degree of Identity of Nucleotide Sequences or Amino Acid Sequences

"Sequence identity" or "% identity" refers to the percentage of residue matches between at least two polypeptide or polynucleotide sequences aligned using a standardized algorithm. Such an algorithm may insert, in a standardized and reproducible way, gaps in the sequences being compared in order to optimize alignment between two or more sequences, and therefore achieve a more meaningful comparison of the sequences. For purposes of the present invention, the sequence identity between two amino acid or nucleotide sequences is determined using the NCBI BLAST program version 2.2.29 (Jan. 06, 2014) (Altschul et al., Nucleic Acids Res. (1997) 25:3389-3402). Sequence identity of two amino acid sequences can be determined with blastp set at the following parameters: Matrix: BLOSUM62, Word Size: 3; Expect value: 10; Gap cost: Existence=11, Extension=1; Filter=low complexity activated; Filter String: L; Compositional adjustments: Conditional compositional score matrix adjustment. For purposes of the present invention, the sequence identity between two nucleotide sequences is determined using the NCBI BLAST program version 2.2.29 (Jan. 06, 2014) with blastn set at the following exemplary parameters: Word Size: 11; Expect value: 10; Gap costs: Existence=5, Extension=2; Filter=low complexity activated; Match/Mismatch Scores: 2,-3; Filter String: L; m.

8. Generation of the Super-Secretor Strain (SSS1)

An expression cassette encoding the enzyme PVA (Penicillin V Amidase) under the control of the GAP promoter and another expression cassette coding for Zeocin was transformed into the *P. pastoris* strain NRRL Y-11430 (see table below). Clones secreting high levels of active PVA were screened by the following enzyme assay:

The cleavage of the PVA substrate penicillin V to the products 6-APA (6-Aminopenicillanic acid) and phenoxyacetic acid was determined by quantifying the phenoxyacetic acid amount by HPLC, One clone showing high PVA titers was identified and named YJK_PVA_021. Surprisingly, this clone not only secreted high amounts of PVA but also the LLP protein at even higher levels. Thus, YJK_PVA_021 was further characterized by whole genome sequencing done by the company Illumina Inc., San Diego, Calif., USA, After de-novo assembly of the genome done by Illumina Inc. (see SEQ ID NOs: 67-115, showing the results of genomic sequencing), the localization of the sequence of the PVA expression construct was identified to be in SEQ ID NO: 103 and the adjacent genomic sequences were compared to the reference strain (*P. Pastoris* CBS 7435, gi|328351301|emb|FR839629.1|) for identification of the insertion site. A single copy of the expression cassette encoding PVA was found to be integrated randomly at position 807,480 of chromosome 1 of the reference strain Pichia pastoris CBS 7435. This position lies within the ssn6-like gene sequence resulting in disruption of the ssn6-like gene leading to a C-terminal truncated protein (see FIG. 2B, see SEQ ID NO: 9) and to a 3'-truncated coding region of the ssn6-like gene, respectively (for details see FIG. 1S, see SEQ ID NO: 23. No further obvious deviations from the reference sequence were found. Thus, this single random integration event resulted in high level secretion of LLP. The PVA expression cassette was removed from YJK_PVA_021 resulting in clone SSS1 (see also FIG. 3).

The vector pGAPk was PCR-amplified (linearized by PCR) using oligo2395 (TCCTCGTCCAATCAGGTAG; SEQ ID NO: 119) and oligo2398 (AGTGGTACCTGCAGCTAAG; SEQ ID NO: 120) and the PCR-product was transformed into yeast strain YJK_PVA_021. Homologous recombination replaced the pGAP-PVA expression vector containing the Zeocin-resistance marker with the empty vector sequence of pGAPk (empty expression cassette and Geneticin-resistance marker), Clones with Geneticin-resistance and without PVA activity were screened. PVA was measured as indicated above. One strain which does not express PVA but expresses high amounts of LLP was denoted SSS1 and used for subsequent expression studies of different GOIs.

9. Characterization of the LLP Signal Sequence

The secreted LLP protein was N-terminally sequenced by Edman degradation to identify the LLP signal sequence cleavage site (Seq. ID NO. 3, FIG. 1C). In order to proof the general functionality of the LLP signal sequence, resulting in the secretion of heterologous proteins fused to the LLP signal sequence, the following experiments were performed:

The LLP signal sequence was fused to the 3' end of HSA coding sequence replacing the native HSA-signal sequence resulting in the sequence according to SEQ. ID NO: 121, (FIG. 1T) and cloned into the pLLP plasmid via EcoRV and NotI restriction enzyme sites. The HSA coding sequence was codon optimized (done by DNA2.0 Inc., Menelo Park, USA) and a silent point mutation was inserted into the LLP-signal sequence at position 45 exchanging G for a C, which does not change the amino acid sequence of the LLP-signal peptide, but which deletes the restriction enzyme site PstI from the LLP-signal sequence. The resulting plasmid was transformed into SSS1 yest strain. 10 clones were randomly picked and subjected to cultivation in deep well plates. 15-20 µl/lane supernatant of deep well plate cultures were directly loaded on SDS-PAGE gels (Novex NuPage 4-12% Bis-Tris Gels from Invitrogen with MES-running buffer). FIG. 12A shows the results of this experiment: Lanes 3 and 7 represent clones bearing no HSA insert, lanes 2, 4, 8 and 10 represent clones according to option 1 (only HSA expressed), and lanes 1, 5, 6 and 9 represent clones according to option 2 (HSA expressed in parallel to LLP). FIG. 12B shows the result of a 1 liter fermenter expression using the same clone used in lane 2 of the gel in FIG. 12A. A sample from the fermenter supernatant was collected after 48, 72 and 96 hours and 15 µl of each sample subjected to SDS-PAGE, followed by Coomassie blue staining using the "SimplyBlue SafeStain" system from Life Technologies according to the manufacturer's instruction.

10. Characterization of the ssn6-like/LLP-Promoter Expression System

The table below shows the basic characteristics of the expression constructs/vectors and the yeast cells used in order to evaluate the functioning of the expresson system for various classes of proteins/genes of interest (GOIs), namely hormones, antibodies, enzymes and structural proteins. The expression results of GOI depicted in the figures were generated with the expression contructs/vetors/host strain combinations listed in the table below. Comparison of the expression of a GOI using a standard GAP-promoter or the LLP-promoter was done using SDS-PAGE, ELISA and/or enzymatic activity assays, as described in the figures.

| Protein name | Protein class | Codon usage for GOI | Signal sequence | GOI inserted in vector between | Plasmid (linearized with) | Resistance marker | Host strain | Comments |
|---|---|---|---|---|---|---|---|---|
| hGH | Hormone | codon optimized for *Pichia pastoris* | *S. cerevisiae* MF-alpha (without EAEA repeat) | EcoRV and NotI | pLLP (AvrII) | Zeocin | SSS1 | pLLP from Sandoz |
|  |  |  |  | EcoRI and NotI | pGAP (SwaI) | Zeocin | NRRL Y-11430 | pGAP from DNA2.0 (pJ905) |
| DLX521 | Antibody (fragment scFv) | codon optimized for *Pichia pastoris* | *S. cerevisiae* MF-alpha (without EAEA repeat) | EcoRV and NotI | pLLP (AvrII) | Zeocin | SSS1 | pLLP from Sandoz |
|  |  |  |  | EcoRI and NotI | pGAP (SwaI) | Zeocin | NRRL Y-11430 | pGAP from DNA2.0 (pJ905) |
|  |  |  |  | EcoRV and NotI | pLLP (AvrII) | Geneticin | YJK_PVA_021 | pLLP from Sandoz |

-continued

| Protein name | Protein class | Codon usage for GOI | Signal sequence | GOI inserted in vector between | Plasmid (linearized with) | Resistance marker | Host strain | Comments |
|---|---|---|---|---|---|---|---|---|
| PVA | Enzyme | codon optimized for *Pichia pastoris* | *S. cerevisiae* MF-alpha (with EAEA repeat) | EcoRV and NotI | pLLP (AvrII) | Zeocin | SSS1 | pLLP from Sandoz |
|  |  |  |  | EcoRI and NotI | pGAP (BglII*) | Zeocin | NRRL Y-11430 | pGAP from Sandoz |
| HSA | Structural protein | codon optimized for *Pichia pastoris* | Human HSA pre-pro signal sequence | EcoRV and NotI | pLLP (AvrII) | Zeocin | SSS1 | pLLP from Sandoz |
|  |  |  |  | EcoRI and NotI I | pGAP (SwaI) | Zeocin | NRRL Y-11430 | pGAP from DNA2.0 (pJ905) |
|  |  |  | *Pichia pastoris* LLP-signal sequence**, *** | EcoRV and NotI | pLLP (AvrII) | Zeocin | SSS1 | pLLP from Sandoz |

*This plasmid was also linearized by PCR as described elsewhere in this application (see paragraph 8. "Generation of the super secretor strain (SSS1)").
**HSA coding sequence was independently codon optimized resulting in identical amino acid sequences but in slightly different nucleotide sequences as compared to the HSA-sequence one row above
***P. pastoris signal sequence contains a silent point mutation at position 45 changing G to C in order to delete a restriction enzyme site 11. Identification of ssn6-Like Consensus Sequences The ssn6-like sequence of *Pichia pastoris* strain NRRL Y-11430 was used for a BLAST-search of similar sequences. BLAST parameters were "automatically adjust paramters for short input sequences", Expect threshold: 10, Word size: 3, Max matches in a querry range: 0, Matrix: BLOSUM62, Gap Costs: Existence: Extension:1, Compositional adjustments: "Conditional compositional score matrix adjustment. The top 39 sequences originate from the following organisms (also see FIG. 9A):

*Komagataella pastoris* CBS 7435 (Synonym/other names: *Pichia pastoris, Pichia pastoris* CBS 7435), *Komagataella pastoris* GS115 (Synonym/other names: *Pichia pastoris, Pichia pastoris* GS115), *Scheffersomyces stipitis* CBS 6054 (Synonym/other names: *Pichia stipitis, Pichia stipitis* CBS 6054), *Millerozyma farinosa* CBS 7064 (other name: *Pichia farinosa* CBS 7064), *Candida parapsilosis, Candida orthopsilosis* Co 90-125, *Debaryomyces hansenii* CBS767, *Spathaspora passalidarum* NRRL Y-27907, *Candida albicans, Candida albicans* SC5314, *Candida maltosa* Xu316, *Candida tropicalis* MYA-3404 (other name: *Candida tropicalis* T1), *Lodderomyces elongisporus* NRRL YB-4239 (other name: *Saccharomyces elongisporus*), *Clavispora lusitaniae* ATCC 4272 (genebank anamorph: *Candida lusitaniae* ATCC 42720), *Meyerozyma guilliermondii* ATCC 6260 (genebank anamorph: *Pichia guilliermondii* ATCC 6260), *Wickerhamomyces ciferrii, Ogataea parapolymorpha* DL-1 (synonym and other names: *Hansenula polymorpha, Hansenula polymorpha* DL-1, *Ogataea angusta* DL-1, *Ogataea parapolymorpha* ATCC 26012, *Ogataea parapolymorpha* DL-1, *Pichia angusta* DL-1), *Cyberlindnera fabianii* (synonyms and other names: *Hansenula fabianii, Pichia fabianii*, . . . ), *Kuraishia capsulata* CBS 1993, *Dictyostelium discoideum* AX4 (belongs to social amoebae), *Tetrapisispora phaffii* CBS 4417 (synonym: *Fabospora phaffii, Dictyostelium purpureum* (belongs to social amoebae), *Pseudozyma flocculosa* PF-1, *Malassezia globosa* CBS 7966, *Botryobasidium botryosum* FD-172 SS1 (basidiomycete), *Naumovozyma dairenensis* CBS 421 (synonyme; *Saccharomyces dairenensis*), *Tetrapisispora blattae* CBS 6284, *Mucor circinelloides f. circinelloides* 1006PhL (Early diverging fungal lineage), *Malassezia sympodialis* ATCC 42132, *Kazachstania naganishii* CBS 8797 (*Saccharomyces naganishii*), *Saccharomyces cerevisiae* YJM789, *Saccharomyces cerevisiae* FostersB, *Saccharomyces cerevisiae, Saccharomyces cerevisiae* S288c, *Ustilago hordei* (Corn smut fungus, basidiomycete), *Meyerozyma guilliermondii* ATCC 6260 (synonym/other names: *Candida guilliermondii, Pichia guilliermondii* ATCC 6260), *Ustilago maydis* 521, (Corn smut fungus, basidiomycete).

Figure 9A:
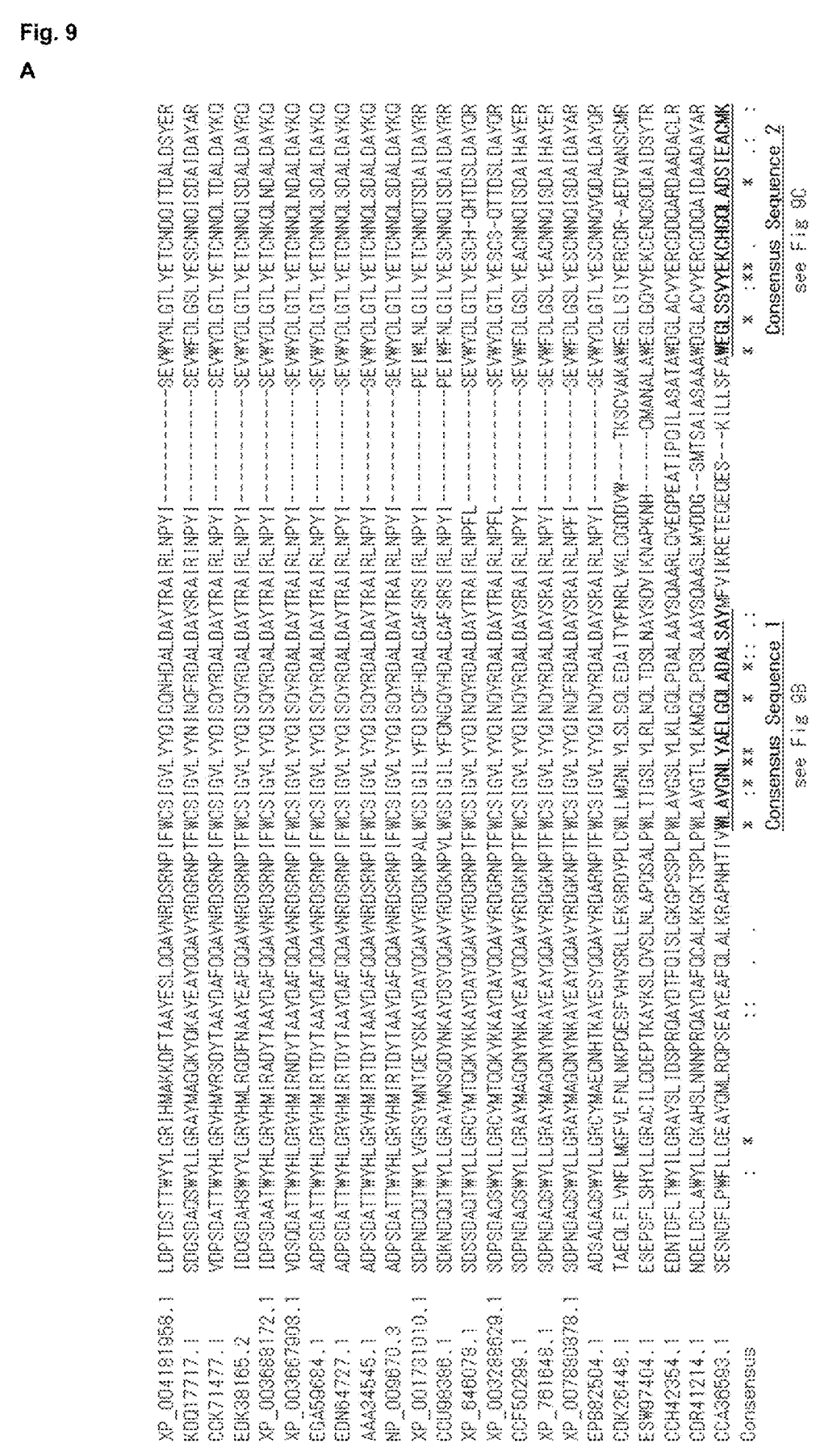
Figure 9:
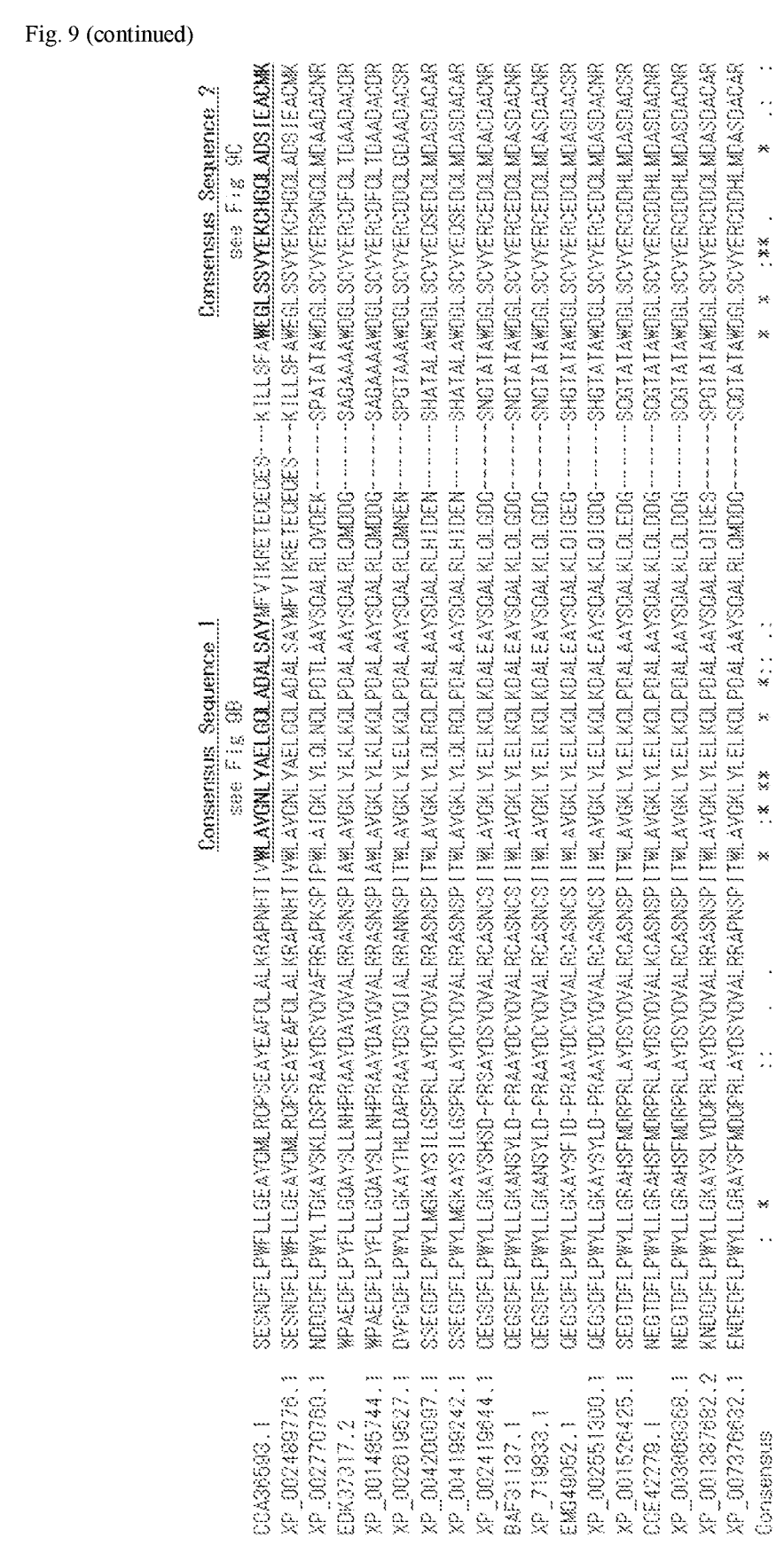

The top 39 identified amino acid sequences were aligned to the ssn6-like-amino acid sequence (=identical to CCA36593.1) revealing significant similarities (see FIGS. 9B and 9C). The alignment was done using the online tool Clustal Omega provided by the EMBL-EBI which is described by Sievers et al., Molecular Systems Biology 7, article number: 539, Valentin et al., Nucleic acids research, 2010, 38, Suppl, W695-9, and by McWilliam et al., Nucleic acids research, 2013, July; 41 (Web Server issue): W597-600. Clustal Omega uses the HHalign algorithm and its default settings as its core alignment engine. The algorithm is described in Söding, J. (2005) 'Protein homology detection by HMM-HMM comparison'. Bioinformatics 21, 951-960. The default transition matrix is Gonnet, gap opening penalty is 6 bits, gap extension is 1 bit. The symbols used for the consensus sequence at the bottom of the alignment are as follows. An "*" (asterisk) indicates amino acid positions which have a single, fully conserved residue across all 40 aligned sequences. A ":" (colon) indicates conservation between groups of amino acids of strongly similar properties—scoring>0.5 in the Gonnet PAM 250 matrix. A "." (period) indicates conservation between groups of amino acids of weakly similar properties—scoring≥0.5 in the Gonnet PAM 250 matrix. Sequence CCA36593.1 corresponds to the *Pichia pastoris* SSN6 sequence identified in this application. FIG. 9A shows only that part of the alignment with the highest similarity between all 40 sequences. FIG. 9B shows the consensus sequence corresponding to Pichia pastoris SSN6-like (CCA36593.1) amino acids 352 to 372. FIG. 9C shows the consensus sequence corresponding to Pichia pastoris SSN6-like (CCA36593.1) amino acids 394 to 417.

Amino acids which are identical in all 40 sequences are written in white with black background-labelling. The consensus sequence shows either individual amino acids which are identical in all 40 sequences or shows a group of amino acids in brackets "( )" and each of the amino acids in such a set of brackets can be chosen alternatively for that position in the consensus sequence. A "-" (dash) indicates that the amino acid at this position may also be omitted from the consensus sequence, which is for example one possibility for positions 406 and 407 of the consensus sequence depicted in FIG. 9C. For example the starting amino acid at position 352 of the consensus sequence in FIG. 9B is "W", meaning that the consensus sequence at this position contains a Tryptophan, position 353 of the consensus sequence in FIG. 9B is written as "(CGL)" meaning that at this position of the consensus sequence can either be located Cysteine, Glycine or Leucine, position 354 is labelled "(SLTA)" meaning that at this position there can either be located Serine, Leucine, Threonine or Alanine, etc. The same nomenclature is used for the second consensus sequence depicted in FIG. 9C. Consensus sequences can be shorter or longer as the two exemplary consensus sequences shown in FIGS. 9B and 9C. Consensus sequences can be deduced from the sequence alignment of FIG. 9A or can be deduced from other parts of the sequence alignment prepared from the 40 above mentioned sequences using the sequence alignment method as described above. Preferably the consensus sequence contains at least 24 amino acids, preferably 23, 22, 21, 20, 19, 18, 17 amino acids, more preferably at least 16, 15, 14, 13, 12, 11, or 10 amino acids, most preferably at least 9, 8, 7, 6, 5 or 4 amino acids. Preferably a SSN6-like protein contains at least one or two consensus sequences, more preferably both consensus sequences shown in FIG. 9B and FIG. 9C, more preferably at least one consensus sequence, most preferably a consensus sequence selected from the sequences shown in FIGS. 9B and 9C.

12. Characterizatin of the Functionality of the LLP-Promoter

The plasmid pLLPk containing DLX521 with MFalpha signal sequence was used as PCR-template in combination with the following PCR-primers to generate shortened/truncated versions of the LLP-promoter (Δ-fragment).

Used reverse primer:

| Primer name | Sequence (5' to 3' end) | Δ-fragment | SEQ ID NO.: |
|---|---|---|---|
| 2892 | TGTCGAACCACCAC TAC | used for all fragments see FIG. 13 A to FIG. 13 D | 122 |

Used forward primer:

| Primer name | Sequence (5' to 3' end) | Δ-fragment | Length of Promoter fragment | SEQ ID NO.: |
|---|---|---|---|---|
| Yo_218 | TATACCTAGGTGGTGGAACT TTATTATTCTTTC | Δ29 | 576 | 123 |
| Yo_219 | TATACCTAGGTATTAGCTGG TAATTGAGCG | Δ93 | 512 | 124 |
| Yo_220 | TATACCTAGGTTGGAGGGT ATGGTCAGAG | Δ133 | 472 | 125 |
| Yo_221 | TATACCTAGGTTTCATTCCA TCTTGCCATC | Δ201 | 404 | 126 |
| Yo_222 | TATACCTAGGCTTACATCAA TAATTAAAAC | Δ233 | 372 | 127 |
| Yo_223 | TATACCTAGGGCAAGCATAT GCTTAAAAGG | Δ300 | 305 | 128 |

The resulting PCR products were ligated in via SpeI and AvrII restriction enzyme sites into the vector pLLPk_containing DLX521. The correct sequences of the resulting plasmids were confirmed by DNA sequencing. The plasmids were linearized with AvrII and transformed in strain YJK_PVA_021. 11 clones per plasmid were randomly picked and subjected to cultivations in deep well plates using a synthetic medium. At harvest, 15 -30 μl supernatant samples were direclty loaded on SDS-PAGE gels (Novex NuPage 4-12% Bis-Tris Gels from Invitrogen with MES-running buffer) to analyze expression of scFv by staining the gels (Simply Blue Safe Stain). The OD600, meaning the yeast cell numbers per ml culture medium at harvest, was comparable for all clones analyzed.

M=Protein Marker VI.

Results are shown in FIG. 13A to FIG. 13D.

13. Examples of ssn6-Like Mutants

The yeast strain contains the modified ssn6-like gene coding for amino acids 1 to 367 and in addition seven amino acids (EWYLQLR; SEQ ID NO: 139) originating from the vector inserted into the ssn6-like gene in order to disrupt the ssn6-like gene. Alternatively, modified versions of ssn6-like might contain a modified ssn6-like gene coding for the following regions of amino acids of SSN6-like protein, to the effect that the modified SSN6-like protein is not able to exert its wildtype function and/or wildtype activity:

Modified versions of SSN6-like protein comprising amino acids 1 to 44, 1 to 77, 1 to 100, 1 to 122, 1 to 155, 1 to 189, 1 to 235, 1 to 275, 1 to 315, 1 to 348, 1 to 400, 1 to 450, 1 to 500, 1 to 550, 1 to 600, 1 to 650, 1 to 367, 1 to 400, 1 to 450, 1 to 500, 1 to 550, 1 to 600, 1 to 650, and/or 1 to 700 of SSN6-like protein according to SEQ ID NO. 9.

In another alternative version the modified versions of ssn6-like might contain the region of the ssn6-like gene coding for blocks of SSN6-like amino acids according to SEQ ID NO. 9, namely amino acids 1 to 44, 45 to 77, 78 to100, 101 to 122, 123 to 155, 156 to189, 190 to 235, 236 to 275, 276 to 315, 316 to 348, 348 to 367, 368 to 400, 401 to 450, 451 to 500, 501 to 550, 551 to 600, 601 to 650, 651 to 700, and/or 701 to 736. Each of these blocks of amino acids might be combined with one or more other blocks of amino acids, preferably in the same order as they occur in SEQ ID NO. 9, wherein none, one or more amino acid block(s) is/are lacking in between two amino acid blocks.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11203620B2). An electronic copy of the "Sequence Listing" will also be available from the USPTO upon request and payment of the fee set forth in 37 CFR 1.19(b)(3).

The invention claimed is:

1. A modified Pichia pastoris cell, which is modified compared to its wildtype cell at least in that it comprises
   a modified ssn6-like gene, and/or
   a modified expression level of SSN6-like protein, or
in that
   a ssn6-like gene is deleted, respectively to the effect that
   the modified Pichia pastoris cell is not able to provide an SSN6-like protein that exerts its wildtype function and/or wildtype activity,
   the amount of SSN6-like protein being present in the modified Pichia pastoris cell differs from the amount of SSN6-like protein being present in its wildtype form, and/or
   essentially no SSN6-like protein is present in the modified Pichia pastoris cell wherein the following definitions apply:
   the SSN6-like gene is defined as comprising SEQ ID NO: 1, and
   the modified Pichia pastoris cell, compared to its unmodified wildtype, is defined as exhibiting reduced or no SSN6-like protein activity and/or function in regulating the expression of genes which are under the control of an LLP promoter, with this LLP promoter comprising SEQ ID NO: 133.

2. The modified Pichia pastoris cell according to claim 1, wherein said modified Pichia pastoris cell exhibits reduced SSN6-like-protein activity and/or reduced function, or no SSN6-like-protein activity and/or function at all.

3. The modified Pichia pastoris cell according to claim 1, wherein said wildtype cell contains a SSN6-like protein, which protein comprises one or both of the consensus amino acid sequences depicted in SEQ ID NO: 63 and 64.

4. The modified Pichia pastoris cell according to claim 1, comprising an expression vector comprising a promoter, wherein said promoter is characterized in that it is repressed in the presence of SSN6-like protein if said expression vector is introduced into a suitable expression system, and wherein said promoter is an LLP promoter comprising SEQ ID NO: 133 or modified versions thereof, said modified versions being characterized in that they still exhibit the promoter function, wherein an LLP protein, which is encoded by the nucleotide sequence depicted in SEQ ID NO: 16, is not encoded by the polynucleotide sequence of this expression vector.

5. An expression system, comprising
   a) the modified Pichia pastoris cell as defined in claim 1;
   b) an expression vector comprising a promoter, wherein said promoter is characterized in that it is repressed in the presence of SSN6-like protein if said expression vector is introduced into a suitable expression system, wherein said expression vector can also be present in linearized form and/or at least parts of the vector being integrated into the genome of the modified eukaryotic cell, and wherein said promoter is an LLP promoter comprising SEQ ID NO: 133 or modified versions thereof, said modified versions being characterized in that they still exhibit the promoter function, wherein an LLP protein, which is encoded by the nucleotide sequence depicted in SEQ ID NO: 16, is not encoded by the polynucleotide sequence of this expression vector.

6. The modified Pichia pastoris cell according to claim 1, further comprising a promoter that it is repressed in the presence of SSN6-like protein if an expression vector comprising the promotor is introduced into a suitable expression system, and wherein said promoter is an LLP promoter comprising SEQ ID NO: 133 or modified versions thereof, said modified versions being characterized in that they still exhibit the promoter function, wherein an LLP protein, which is encoded by the nucleotide sequence depicted in SEQ ID NO: 16, is not encoded by the polynucleotide sequence of this expression vector, and/or
further comprising (a) gene(s) of interest being under control of the promoter, and/or wherein the gene(s) of interest is (are) selected from the group consisting of genes encoding enzymes, antibodies or fragments thereof, hormones, structural proteins, and protein-antigens being present in vaccines.

7. Method for determining the purity of a composition comprising the expression product of a gene of interest, i.e. a protein(s) of interest, comprising the following steps:
   (a) expressing gene(s) of interest by using the modified Pichia pastoris cell according to claim 1 and by using an expression vector comprising a the LLP promoter, wherein sad promoter is characterized in that it is repressed in the presence of SSN6-like protein if sad expression vector is introduced into a suitable expression system, and wherein LLP protein is not encoded by the polynucleotide sequence of the expression vector, wherein
   (a1) the modified Pichia pastoris cell comprises a gene encoding the LLP protein under control of the LLP promoter, and wherein
   (a2) the expression vector comprises one or more gene(s) of interest under control of the LLP promoter, wherein sad gene(s) of interest does (do) not encode the LLP protein,
   thereby obtaining a composition comprising the expression product of the gene(s) of interest, i.e. the protein(s) of interest, and the LLP protein, which is an expression product of the gene encoding the LLP protein which gene is comprised in the modified Pichia pastoris cell of (a1);
   (b) determining the amount of the expression product of the gene(s) of interest, i.e. the amount of the protein(s)

of interest, and the amount of LLP protein being present in the composition obtained in step (a), wherein the amount of LLP protein compared to the amount of expression product of the gene(s) of interest, i.e. of the protein(s) of interest, is indicative for the purity of the composition obtained in step (a); and, optionally, (c) subjecting the composition of step (a) to one or more downstream purification step(s), followed by step (b) for determining the amount of the expression product of the gene(s) of interest, i.e. the protein(s) of interest, and the amount of LLP protein being present in the composition obtained after having carried out sad downstream purification step, wherein sad LLP promoter being present in the Pichia pastoris cell and being present in the expression vector is the LLP promoter respectively comprising SEQ ID NO: 133 or modified versions thereof, sad modified versions being characterized in that they still exhibit the promoter function, wherein the LLP protein, which is encoded by the nucleotide sequence depicted in SEQ ID NO: 16, is not encoded by the polynucleotide sequence of the expression vector of (a).

8. The modified Pichia pastoris cell according to claim 1, wherein
A) the nucleotide sequence of the SSN6-like gene is modified by introduction of a point mutation, a partial or complete deletion, or a replacement by a different nucleotide sequence; and/or
B) the expression level of the SSN6-like protein is modified by impairing the transcription or translation of the gene encoding SSN6-like protein.

9. A method for expressing a gene of interest, comprising the steps of: expressing a gene of interest by using the modified Pichia pastoris cell according to claim 1, thus obtaining a recombinant protein expressed by the gene of interest; and
purifying the thus-obtained recombinant protein.

10. The method according to claim 9, wherein the modified Pichia pastoris cell exhibits reduced SSN6-like-protein activity and/or reduced function, or no SSN6-like-protein activity and/or function at all.

11. The method according to claim 9, wherein the wildtype cell, compared to which the modified Pichia pastoris cell is modified, contains a SSN6-like protein, which protein comprises one or both of the consensus amino acid sequences depicted in SEQ ID NO: 63 and 64.

12. The method according to claim 9, wherein the modified Pichia pastoris cell comprises
a modified ssn6-like gene, wherein said gene has inserted a foreign nucleotide sequence, to the effect that
(i) the Pichia pastoris cell is not able to provide an SSN6-like protein that exerts its wildtype function and/or wildtype activity,
(ii) the amount of SSN6-like protein being present in the eukaryotic cell differs from the amount of SSN6-like protein being present in its wildtype form, and/or
(iii) essentially no SSN6-like protein is present in the Pichia pastoris cell, and
a gene of interest that replaces a part or all of the coding region of the gene of the Pichia
pastoris cell encoding the LLP protein, and that is under control of the LLP promoter,
wherein
said promoter is an LLP promoter comprising SEQ ID NO: 133 or modified versions thereof, said modified versions being characterized in that they still exhibit the promoter function.

13. The method according to claim 9, wherein the modified Pichia pastoris cell comprises
a modified ssn6-like gene, wherein said gene has inserted a foreign nucleotide sequence, to the effect that
(i) the Pichia pastoris cell is not able to provide an SSN6-like protein that exerts its wildtype function and/or wildtype activity,
(ii) the amount of SSN6-like protein being present in the Pichia pastoris cell differs from the amount of SSN6-like protein being present in its wildtype form, and/or
(iii) essentially no SSN6-like protein is present in the Pichia pastoris cell,
a gene of interest under control of the LLP promoter, and an llp gene,
wherein
said promoter is an LLP promoter comprising SEQ ID NO: 133 or modified versions thereof, said modified versions being characterized in that they still exhibit the promoter function.

14. The method according to claim 9, wherein the modified Pichia pastoris cell comprises a SSN6-like gene, wherein the nucleotide sequence of said SSN6-like gene is modified by introduction of a point mutation, a partial or complete deletion, or a replacement by a different nucleotide sequence; and/or wherein the modified Pichia pastoris cell expresses a SSN6-like protein, wherein the expression level of said SSN6-like protein is modified by impairing the transcription or translation of the gene encoding SSN6-like protein.

15. A Pichia pastoris cell comprising
a modified ssn6-like gene, wherein said gene has inserted a foreign nucleotide sequence, to the effect that
(i) the Pichia pastoris cell is not able to provide an SSN6-like protein that exerts its wildtype function and/or wildtype activity,
(ii) the amount of SSN6-like protein being present in the eukaryotic cell differs from the amount of SSN6-like protein being present in its wildtype form, and/or
(iii) essentially no SSN6-like protein is present in the Pichia pastoris cell, and
a gene of interest that replaces a part or all of the coding region of the gene of the Pichia pastoris cell encoding a LLP protein, and that is under control of a LLP promoter,
wherein
said LLP promoter is an LLP promoter comprising SEQ ID NO: 133 or modified versions thereof, said modified versions being characterized in that they still exhibit the promoter function.

16. A Pichia pastoris cell comprising
a modified ssn6-like gene, wherein said gene has inserted a foreign nucleotide sequence, to the effect that
(i) the Pichia pastoris cell is not able to provide an SSN6-like protein that exerts its wildtype function and/or wildtype activity,
(ii) the amount of SSN6-like protein being present in the Pichia pastoris cell differs from the amount of SSN6-like protein being present in its wildtype form, and/or
(iii) essentially no SSN6-like protein is present in the Pichia pastoris cell,
a gene of interest under control of the LLP promoter, and an llp gene,
wherein
said promoter is an LLP promoter comprising SEQ ID NO: 133 or modified versions thereof,
said modified versions being characterized in that they still exhibit the promoter function.

* * * * *